(12) United States Patent
Terauchi et al.

(10) Patent No.: US 12,138,315 B2
(45) Date of Patent: Nov. 12, 2024

(54) ANTI-CD37 ANTIBODY-DRUG CONJUGATE

(71) Applicant: DAIICHI SANKYO COMPANY, LIMITED, Tokyo (JP)

(72) Inventors: Tomoko Terauchi, Tokyo (JP); Yuji Shinjo, Tokyo (JP); Hajime Sugawara, Tokyo (JP); Yusuke Shuchi, Tokyo (JP); Riki Goto, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 18/411,436

(22) Filed: Jan. 12, 2024

(65) Prior Publication Data

US 2024/0165254 A1 May 23, 2024

Related U.S. Application Data

(63) Continuation of application No. PCT/JP2022/038604, filed on Oct. 17, 2022.

(30) Foreign Application Priority Data

Oct. 18, 2021 (JP) .................................. 2021-170114

(51) Int. Cl.
*A61K 47/68* (2017.01)
*A61P 35/00* (2006.01)

(52) U.S. Cl.
CPC .... *A61K 47/6849* (2017.08); *A61K 47/68037* (2023.08); *A61K 47/6889* (2017.08); *A61P 35/00* (2018.01)

(58) Field of Classification Search
None
See application file for complete search history.

(56) References Cited

U.S. PATENT DOCUMENTS 10,307,481 B2 6/2019 Grosmaire et al.
10,646,583 B2 5/2020 Pereira et al.
(Continued)

FOREIGN PATENT DOCUMENTS

JP 2009-502171 A 1/2009
JP 2010-535483 A 11/2010
(Continued)

OTHER PUBLICATIONS

Arroyo-Olarte et al., "Genome Editing in Bacteria: CRISPR-Cas and Beyond," Microorganisms, vol. 9, No. 4, 2021, pp. 1-25.
(Continued)

*Primary Examiner* — Karl J Puttlitz
(74) *Attorney, Agent, or Firm* — Foley & Lardner LLP

(57) ABSTRACT

It is an object to provide an antibody specifically binding to CD37-positive tumor cells such as malignant B-cell lymphoma, an antibody-drug conjugate comprising the antibody, a pharmaceutical composition having therapeutic effects on a tumor using the antibody, a method for treating a tumor using the aforementioned pharmaceutical composition, a method for producing the antibody, and a method for producing the antibody-drug conjugate, and the like. The present invention provides an anti-CD37 antibody-drug conjugate in which an antibody is conjugated to a drug linker represented by the following formula (wherein A represents (Continued)

SEQ ID NO: 1: Nucleotide sequence encoding hmAb-L11 light chain

```
ATGGTGCTGCAGACCCAGGTGTTCATCTCCCTGCTGCTGTGGATCTCCGGCGCGTACGGCGAT
ATCCAGATGACACAGAGCCCTAGCAGCCTGTCTGCCAGCGTGGGAGACAGAGTGACCATCACA
TGCAAGGCCAGCCAGGATGTCTCCACCGCCGTGCATTGGTATCAGCAGAAGCCTGGCAAGGCC
CCTAAGCTGCTGATCAACTGGGCCAGCACAAGACACACAGGCGTGCCCAGCAGATTTTCTGGC
AGCGGCTCTGGCACCGACTTCACCCTGACCATATCTAGCCTGCAGCCTGAGGACTTCGCCACC
TACTACTGCAGACAGCACTACAGCACCCTTTCACCTTTGGCCAGGGCACCAAGGTGGAAATC
AAGCGTACGGTGGCCGCCCCTCCGTGTTCATCTTCCCCCCTCCGACGAGCAGCTGAAGTCC
GGCACCGCCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGACAGCAA
GGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACA
GGGGCGAGTGT
```
Signal sequence (1-60), Light chain variable region (61-384), Light chain constant region (385-702)

SEQ ID NO: 2: Amino acid sequence of hmAb-L11 light chain

```
MVLQTQVFISLLLWISGAYGDIQMTQSPSSLSASVGDRVTITCKASQDVSTAVDWYQQKPGKAPK
LLINWASTRHTGVPSRFSGSGSGTDFTLTISSLQPEDFATYYCRQHYSTPFTFGQGTKVEIKRTVA
APSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC
```
Signal sequence (1-20), Light chain variable region (21-128), Light chain constant region (129-234)

a connecting position to the antibody) by a thioether bond, specifically, a humanized anti-CD37 antibody having internalization ability and an antibody-drug conjugate containing the antibody.

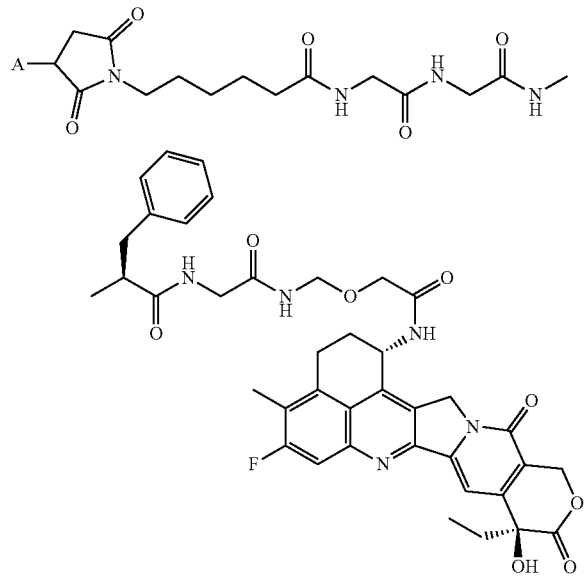

46 Claims, 11 Drawing Sheets

Specification includes a Sequence Listing.

(56) References Cited

U.S. PATENT DOCUMENTS

| 2014/0348745 | A1 | 11/2014 | Larsen et al. |
| 2016/0297890 | A1 | 10/2016 | Agatsuma et al. |
| 2020/0270361 | A1 | 8/2020 | Deckert et al. |
| 2021/0230271 | A1 | 7/2021 | Heider et al. |

FOREIGN PATENT DOCUMENTS

| JP | 2014-515742 A | 7/2014 |
| JP | 2015-501654 A | 1/2015 |
| JP | 2016-532688 A | 10/2016 |
| WO | WO-2011/112978 A1 | 9/2011 |
| WO | WO-2014/057687 A1 | 4/2014 |
| WO | WO-2017/002776 A1 | 1/2017 |
| WO | WO-2020/022363 A1 | 1/2020 |

OTHER PUBLICATIONS

Agatsuma, Toshinori, "Development of New ADC Technology with Topoisomerase I Inhibitor," The Pharmaceutical Society of Japan, vol. 137, No. 5, pp. 545-550.
Salles et al., "Rituximab in B-Cell Hematologic Malignancies: A Review of 20 Years of Clinical Experience," Advances in Therapy, vol. 34, 2017, pp. 2232-2273.
Rezvani et al., "Rituximab resistance," Best Practice & Research Clinical Haematology, vol. 24, Issue 2, Jun. 2011, pp. 203-216.
Polakis, Paul, "Antibody Drug Conjugates for Cancer Therapy," Pharmacological Reviews, vol. 68, No. 1, Jan. 2016, pp. 3-19.
Peters et al., "Antibody—drug conjugates as novel anti-cancer chemotherapeutics," Bioscience Reports, vol. 35, Issue 4, Aug. 2015, e00225, pp. 1-20.
Charrin et al., "Tetraspanins at a glance," Journal of Cell Science, vol. 127, 2014, pp. 3641-3648.
Witkowska et al., "Investigational therapies targeting CD37 for the treatment of B-cell lymphoid malignancies," Expert Opinion on Investigational Drugs, vol. 27, Issue 2, 2018, pp. 171-177.
Knobeloch et al., "Targeted Inactivation of the Tetraspanin CD37 Impairs T-Cell-Dependent B-Cell Response under Suboptimal Costimulatory Conditions," Molecular and Cellular Biology, vol. 20, Issue 15, 2000, pp. 5363-5369.
Payandeh et al., "Anti-CD37 targeted immunotherapy of B-Cell malignancies," Biotechnology Letters, vol. 40, 2018, pp. 1459-1466.
Deckert et al., "A novel anti-CD37 antibody-drug conjugate with multiple anti-tumor mechanisms for the treatment of B-cell malignancies," Blood, vol. 122, No. 20, 2013, pp. 3500-3510.
Stathis et al., "Safety, tolerability, and preliminary activity of IMGN529, a CD37-targeted antibody-drug conjugate, in patients with relapsed or refractory B-cell non-Hodgkin lymphoma: a dose-escalation, phase I study," Invest New Drugs, vol. 36, No. 5, Oct. 2018, pp. 869-876.
Pichard et al., "The therapeutic effectiveness of $^{177}$Lu-lilotomab in B-cell non-Hodgkin lymphoma involves modulation of G2/M cell cycle arrest," Leukemia, vol. 34, No. 5, 2020, pp. 1315-1328.
Oostindie et al., "DuoHexaBody-CD37®, a novel biparatopic CD37 antibody with enhanced Fc-mediated hexamerization as a potential therapy for B-cell malignancies," Blood Cancer Journal, vol. 10, No. 30, 2020, pp. 1-13.
Scarfò et al., "Anti-CD37 chimeric antigen receptor T cells are active against B-and T-cell lymphomas," Blood, vol. 132, No. 4, Oct. 2018, pp. 1495-1506.
Keam et al., "Trastuzumab Deruxtecan: First Approval," Drugs, vol. 80, No. 5, Apr. 2020, pp. 501-508.
Yonesaka et al., "An HER3-targeting antibody-drug conjugate incorporating a DNA topoisomerase I inhibitor U3-1402 conquers EGFR tyrosine kinase inhibitor-resistant NSCLC," Oncogene, vol. 38, Issue 9, Feb. 2019, pp. 1398-1409.
Okajima et al., "Datopotamab Deruxtecan, a Novel TROP2-directed Antibody—drug Conjugate, Demonstrates Potent Antitumor Activity by Efficient Drug Delivery to Tumor Cells," Molecular Cancer Therapeutics, vol. 20, No. 12, 2021, pp. 2329-2340.
International Searching Authority, "International Search Report," issued in connection with International Patent Application No. PCT/JP2022/038604, dated Jan. 10, 2023.
International Searching Authority, "Written Opinion," issued in connection with International Patent Application No. PCT/JP2022/038604, dated Jan. 10, 2023.

[Figure 1]

SEQ ID NO: 1: Nucleotide sequence encoding hmAb-L11 light chain
ATGGTGCTGCAGACCCAGGTGTTCATCTCCCTGCTGCTGTGGATCTCCGGCGCGTACGGCGAT
ATCCAGATGACACAGAGCCCTAGCAGCCTGTCTGCCAGCGTGGGAGACAGAGTGACCATCACA
TGCAAGGCCAGCCAGGATGTGTCCACCGCCGTGGATTGGTATCAGCAGAAGCCTGGCAAGGCC
CCTAAGCTGCTGATCAACTGGGCCAGCACAAGACACACAGGCGTGCCCAGCAGATTTTCTGGC
AGCGGCTCTGGCACCGACTTCACCCTGACCATATCTAGCCTGCAGCCTGAGGACTTCGCCACC
TACTACTGCAGACAGCACTACAGCACCCCTTTCACCTTTGGCCAGGGCACCAAGGTGGAAATC
AAGCGTACGGTGGCCGCCCCTCCGTGTTCATCTTCCCCCCTCCGACGAGCAGCTGAAGTCC
GGCACCGCCTCCGTGGTGTGCCTGCTGAATAACTTCTACCCCAGAGAGGCCAAGGTGCAGTGG
AAGGTGGACAACGCCCTGCAGTCCGGGAACTCCCAGGAGAGCGTGACCGAGCAGGACAGCAA
GGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACA
GGGGGGAGTGT
Signal sequence (1-60), Light chain variable region (61-384), Light chain constant region (385-702)

SEQ ID NO: 2: Amino acid sequence of hmAb-L11 light chain
MVLQTQVFISLLLWISGAYGDIQMTQSPSSLSASVGDRVTITCKASQDVSTAVDWYQQKPGKAPK
LLINWASTRHTGVPSRFSGSGSGTDFTLTISSLQPEDFATYYCRQHYSTPFTFGQGTKVEIKRTVA
APSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC
Signal sequence (1-20), Light chain variable region (21-128), Light chain constant region (129-234)

[Figure 2]

SEQ ID NO: 3: Nucleotide sequence encoding hmAb-H11 heavy chain
ATGAAACACCTGTGGTTCTTCCTCCTGCTGGTGGCAGCTCCCAGATGGGTGCTGAGCGAAGTT
CAGCTGGTTCAGTCTGGCGCCGAAGTGAAGAAACCTGGCGCCTCTGTGAAGGTGTCCTGCAA
GGCCAGCGGCTACAGCTTCACCGACTACAACATGTACTGGGTCCGACAGGCCCCTGGCCAGTC
TCTTGAGTGGATGGGCTACATCGACCCCTACAACGGCGACACCACCTACAACCAGAAATTCCA
GGGCAGAGTGACCATCACCGCCGACACCTCTACAAGCACCGCCTACATGGAACTGAGCAGCCT
GAGAAGCGAGGACACCGCCGTGTACTACTGCGCCAGATCTCCTTACGGCCACTACGCCATGGA
TTACTGGGGCCAGGGAACCCTGGTCACAGTTAGCTCAGCCTCCACCAAGGGCCCAAGCGTCTT
CCCCCTGGCACCCTCCTCCAAGAGCACCTCTGGCGGCACAGCCGCCCTGGGCTGCCTGGTCAA
GGACTACTTCCCCGAACCCGTGACCGTGAGCTGGAACTCAGGCGCCCTGACCAGCGGCGTGC
ACACCTTCCCGCTGTCCTGCAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACCA
AGGTGGACAAGAAGGTTGAGCCCAAATCTTGTGACAAAACTCACACATGCCCACCCTGCCCAG
CACCTGAACTCCTGGGGGGACCCTCAGTCTTCCTCTTCCCCCCAAAACCCAAGGACACCCTCA
TGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGA
GGAGCAGTACAACAGCACGTACCGGGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGAAAAC
CATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACAT
CGCCGTGGAGTGGGAGAGCAATGGCCAGCCGGAGAACAACTACAAGACCACCCCTCCCGTGC
TGGACTCCGACGGCTCCTTCTTCCTCTACAGCAAGCTCACCGTGGACAAGAGCAGGTGGCAGC
AGGGCAACGTCTTCTCATGCTCCGTGATGCATGAGGCTCTGCACAACCACTACACCCAGAAGA
GCCTCTCCCTGTCTCCGGGCAAA
Signal sequence (1-57), Heavy chain variable region (58-414), Heavy chain constant region (415-1404)

SEQ ID NO: 4: Amino acid sequence of hmAb-H11 heavy chain
MKHLWFFLLLVAAPRWVLSEVQLVQSGAEVKKPGASVKVSCKASGYSFTDYNMYWVRQAPGQS
LEWMGYIDPYNGDTTYNQKFQGRVTITADTSTSTAYMELSSLRSEDTAVYYCARSPYGHYAMDY
WGQGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSV
MHEALHNHYTQKSLSLSPGK
Signal sequence (1-19), Heavy chain variable region (20-138), Heavy chain constant region (139-468)

[Figure 3]

SEQ ID NO: 5: Nucleotide sequence encoding hmAb-H541 heavy chain
ATGAAACACCTGTGGTTCTTCCTCCTGCTGGTGGCAGCTCCCAGATGGGTGCTGAGCGAAGTG
CAGCTGGTTCAGTCTGGCGCCGAAGTGAAAAAGCCTGGCGCCTCTGTGAAGGTGTCCTGCAA
GGCCAGCGGCTACAGCTTCACCGACTACAACATGTACTGGGTCCGACAGGCCCCTGGCCAGTC
TCTTGAGTGGATGGGCTACATCGACCCCTACAACGGCGACACCACCTACAACCAGAAATTCCA
GGGCAGAGTGACCATGACCAGAGACACCAGCATCAGCACCGCCTACATGGAACTGAGCCGGCT
GAGATCCGATGACACCGCCGTGTACTACTGCGCCAGATCTCCTTACGGCCACTACGCCATGGAT
TACTGGGGCCAGGGCACCACAGTGACAGTTAGCTCAGCCTCCACCAAGGGCCCAAGCGTCTTC
CCCCTGGCACCCTCCTCCAAGAGCACCTCTGGCGGCACAGCCGCCCTGGGCTGCCTGGTCAA
GGACTACTTCCCCGAACCCGTGACCGTGAGCTGGAACTCAGGCGCCCTGACCAGCGGCGTGC
ACACCTTCCCGGCTGTCCTGCAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACCA
AGGTGGACAAGAAGGTTGAGCCCAAATCTTGTGACAAAACTCACACATGCCCACCCTGCCCAG
CACCTGAACTCCTGGGGGGACCCTCAGTCTTCCTCTTCCCCCCAAAACCCAAGGACACCCTCA
TGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGA
GGAGCAGTACAACAGCACGTACCGGGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGAAAAC
CATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACAT
CGCCGTGGAGTGGGAGAGCAATGGCCAGCCCGAGAACAACTACAAGACCACCCCTCCCGTGC
TGGACTCCGACGGCTCCTTCTTCCTCTACAGCAAGCTCACCGTGGACAAGAGCAGGTGGCAGC
AGGGCAACGTCTTCTCATGCTCCGTGATGCATGAGGCTCTGCACAACCACTACACCCAGAAGA
GCCTCTCCCTGTCTCCGGCAAA
Signal sequence (1-57), Heavy chain variable region (58-414), Heavy chain constant region (415-1404)

SEQ ID NO: 6: Amino acid sequence of hmAb-H541 heavy chain
MKHLWFFLLLVAAPRWVLSEVQLVQSGAEVKKPGASVKVSCKASGYSFTDYNMYWVRQAPGQS
LEWMGYIDPYNGDTTYNQKFQGRVTMTRDTSISTAYMELSRLRSDDTAVYYCARSPYGHYAMD
YWGQGTTVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK
Signal sequence (1-19), Heavy chain variable region (20-138), Heavy chain constant region (139-468)

[Figure 4]

SEQ ID NO: 7: Nucleotide sequence encoding hmAb-H551 heavy chain
ATGAAACACCTGTGGTTCTTCCTCCTGCTGGTGGCAGCTCCCAGATGGGTGCTGAGCGAAGTG
CAGCTGGTTCAGTCTGGCGCCGAAGTGAAAAAGCCTGGCGCCTCTGTGAAGGTGTCCTGCAA
GGCCAGCGGCTACAGCTTCACCGACTACAACATGTACTGGGTCCGACAGGCCCCTGGCCAGTC
TCTTGAGTGGATGGGCTACATCGACCCCTACAACGGCGACACCACCTACAACCAGAAATTCCA
GGGCAGAGTGACCATGACCAGAGACACCAGCAGCAGCACCGCCTACATGGAACTGAGCAGAC
TGAGAAGCGACGACACCGCCGTGTACTACTGCGCCAGATCTCCTTACGGCCACTACGCCATGG
ATTACTGGGGCCAGGGCACCACAGTGACAGTTAGCTCAGCCTCCACCAAGGGCCCAAGCGTCT
TCCCCCTGGCACCCTCCTCCAAGAGCACCTCTGGCGGCACAGCCGCCCTGGGCTGCCTGGTCA
AGGACTACTTCCCCGAACCCGTGACCGTGAGCTGGAACTCAGGCGCCCTGACCAGCGGCGTG
CACACCTTCCCCGCTGTCCTGCAGTCCTCAGGACTCTACTCCCTCAGCAGCGTGGTGACCGTG
CCCTCCAGCAGCTTGGGCACCCAGACCTACATCTGCAACGTGAATCACAAGCCCAGCAACACC
AAGGTGGACAAGAAGGTTGAGCCCAAATCTTGTGACAAAACTCACACATGCCCACCGTGCCCA
GCACCTGAACTCCTGGGGGGACCCTCAGTCTTCCTCTTCCCCCCAAAACCCAAGGACACCCTC
ATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGA
GGAGCAGTACAACAGCACGTACCGGGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGAAAAC
CATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACAT
CGCCGTGGAGTGGGAGAGCAATGGCCAGCCCGAGAACAACTACAAGACCACCCCTCCCGTGC
TGGACTCCGACGGCTCCTTCTTCCTCTACAGCAAGCTCACCGTGGACAAGAGCAGGTGGCAGC
AGGGCAACGTCTTCTCATGCTCCGTGATGCATGAGGCTCTGCACAACCACTACACCCAGAAGA
GCCTCTCCCTGTCTCCGGGCAAA Signal sequence (1-57), Heavy chain variable region (58-414), Heavy chain constant region (415-1404)

SEQ ID NO: 8: Amino acid sequence of hmAb-H551 heavy chain
MKHLWFFLLLVAAPRWVLSEVQLVQSGAEVKKPGASVKVSCKASGYSFTDYNMYWVRQAPGQS
LEWMGYIDPYNGDTTYNQKFQGRVTMTRDTSSSTAYMELSRLRSDDTAVYYCARSPYGHYAMD
YWGQGTTVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal sequence (1-19), Heavy chain variable region (20-138), Heavy chain constant region (139-468)

[Figure 5]

SEQ ID NO: 9: Nucleotide sequence encoding hmAb-H11a heavy chain
ATGAAACACCTGTGGTTCTTCCTCCTGCTGGTGGCAGCTCCCAGATGGGTGCTGAGCGAAGTG
CAGCTGGTTCAGTCTGGCGCCGAAGTGAAAAAGCCTGGCGCCTCTGTGAAGGTGTCCTGCAA
GGCCAGCGGCTACAGCTTCACCGACTACAACATGTACTGGGTCCGACAGGCCCCTGGCCAGTC
TCTTGAGTGGATGGGCTACATCGACCCCTACAACGGCGACACCACCTACAACCAGAAATTCCA
GGGCAGAGTGACCATCACCGCCGACAAGAGCAAGAGCACCGCCTACATGGAACTGAGCAGCC
TGAGAAGCGAGGACACCGCCGTGTACTACTGCGCCAGATCTCCTTACGGCCACTACGCCATGG
ATTACTGGGGCCAGGGCACACTGGTTACCGTTAGCTCAGCCTCCACCAAGGGCCCAAGCGTCT
TCCCCCTGGCACCCTCCTCCAAGAGCACCTCTGGCGGCACAGCCGCCCTGGGCTGCCTGGTCA
AGGACTACTTCCCCGAACCCGTGACCGTGAGCTGGAACTCAGGCGCCCTGACCAGCGGCGTG
CACACCTTCCCCGCTGTCCTGCAGTCCTCAGGACTCTACTCCCTCAGCAGCGTGGTGACCGTG
CCCTCCAGCAGCTTGGGCACCCAGACCTACATCTGCAACGTGAATCACAAGCCCAGCAACACC
AAGGTGGACAAGAAGGTTGAGCCCAAATCTTGTGACAAAACTCACACATGCCCACCCTGCCCA
GCACCTGAACTCCTGGGGGGACCCTCAGTCTTCCTCTTCCCCCCAAAACCCAAGGACACCCTC
ATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGA
GGAGCAGTACAACAGCACGTACCGGGTGGTCAGCGTCCTCACCGTCCTGCACCAGGACTGGCT
GAATGGCAAGGAGTACAAGTGCAAGGTCTCCAACAAAGCCCTCCCAGCCCCCATCGAGAAAAC
CATCTCCAAAGCCAAAGGCCAGCCCCGGGAACCACAGGTGTACACCCTGCCCCCATCCCGGGA
GGAGATGACCAAGAACCAGGTCAGCCTGACCTGCCTGGTCAAAGGCTTCTATCCCAGCGACAT
CGCCGTGGAGTGGGAGAGCAATGGCCAGCCCGAGAACAACTACAAGACCACCCCTCCCGTGC
TGGACTCCGACGGCTCCTTCTTCCTCTACAGCAAGCTCACCGTGGACAAGAGCAGGTGGCAGC
AGGGCAACGTCTTCTCATGCTCCGTGATGCATGAGGCTCTGCACAACCACTACACCCAGAAGA
GCCTCTCCCTGTCTCCGGCAAA
Signal sequence (1-57), Heavy chain variable region (58-414), Heavy chain constant region (415-1404)

SEQ ID NO: 10: Amino acid sequence of hmAb-H11a heavy chain
MKHLWFFLLLVAAPRWVLSEVQLVQSGAEVKKPGASVKVSCKASGYSFTDYNMYWVRQAPGQS
LEWMGYIDPYNGDTTYNQKFQGRVTITADKSKSTAYMELSSLRSEDTAVYYCARSPYGHYAMDY
WGQGTLVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSV
MHEALHNHYTQKSLSLSPGK
Signal sequence (1-19), Heavy chain variable region (20-138), Heavy chain constant region (139-468)

[Figure 6]
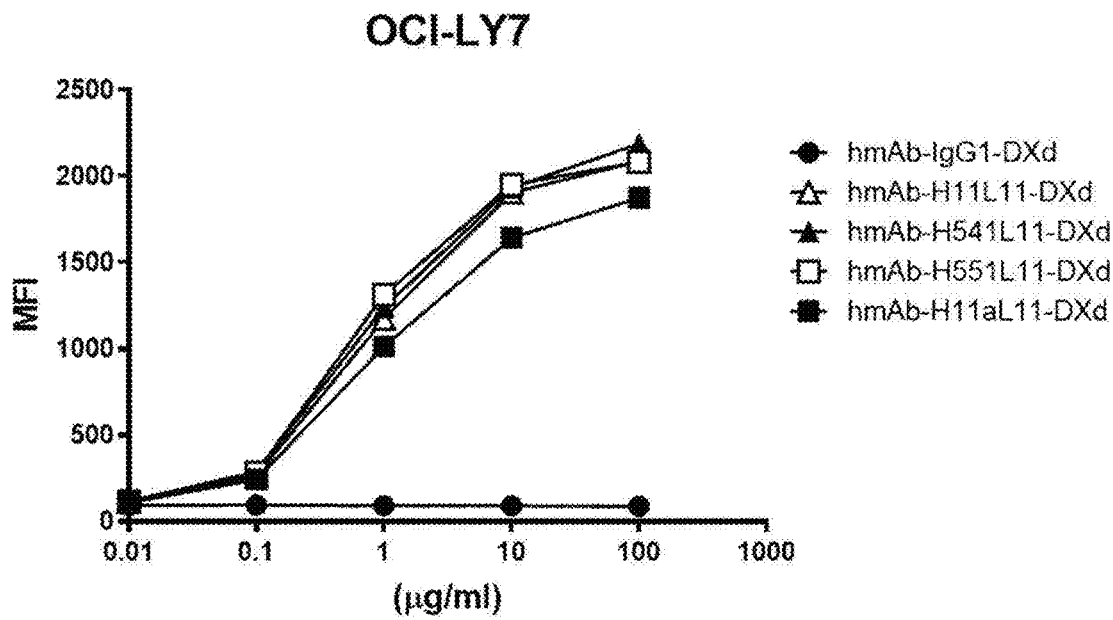
[Figure 7]
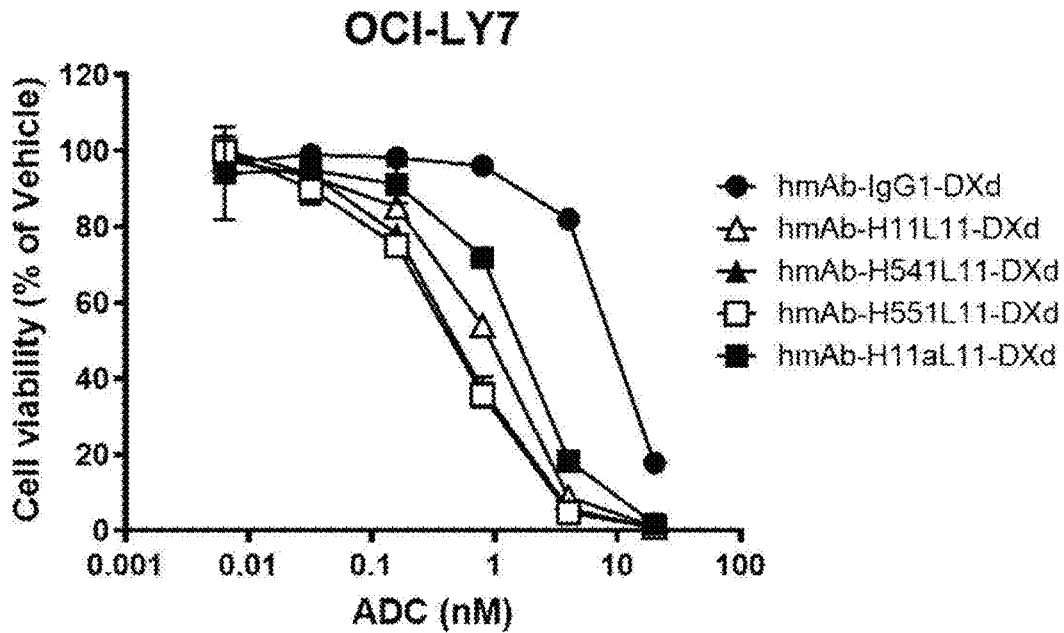

[Figure 8]
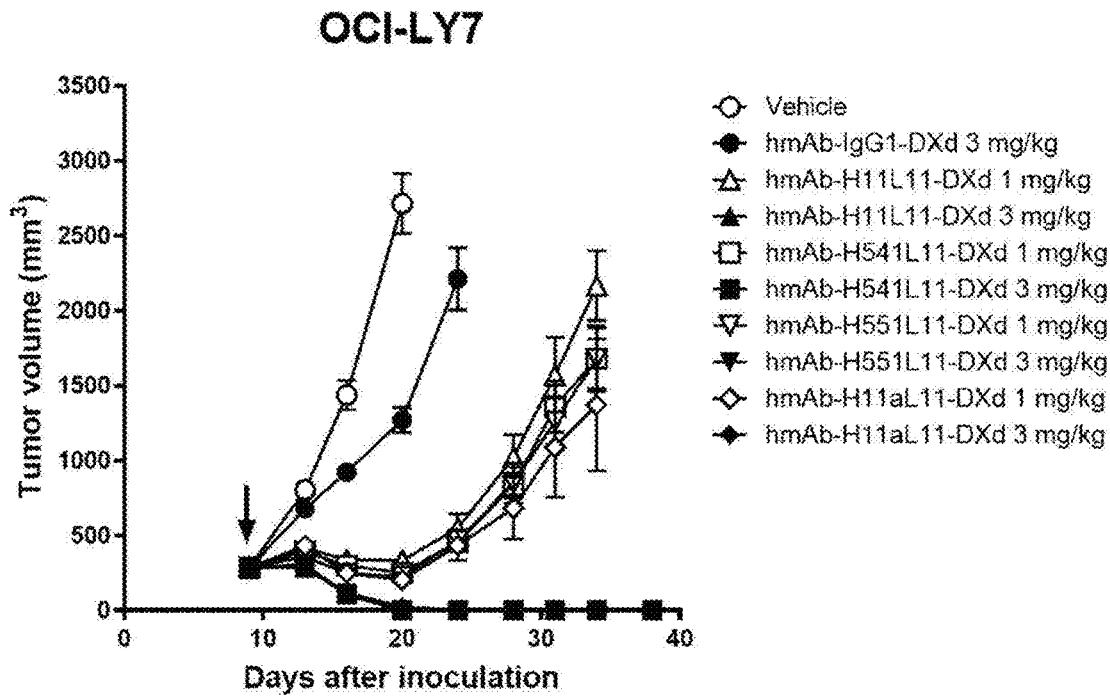
[Figure 9]
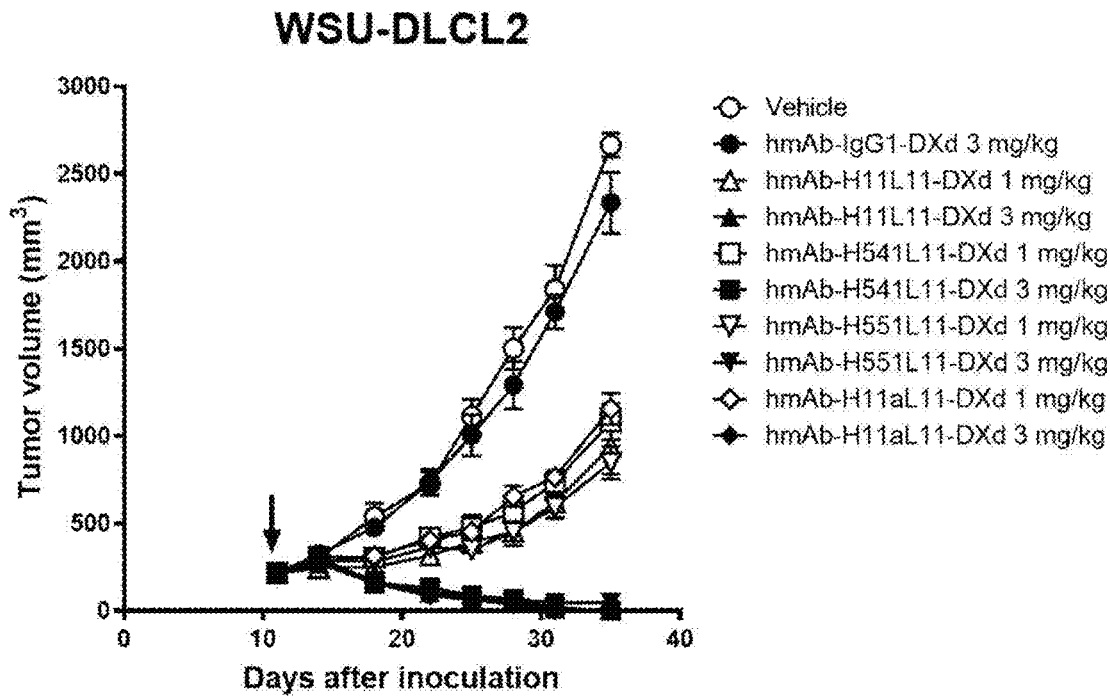

[Figure 10]
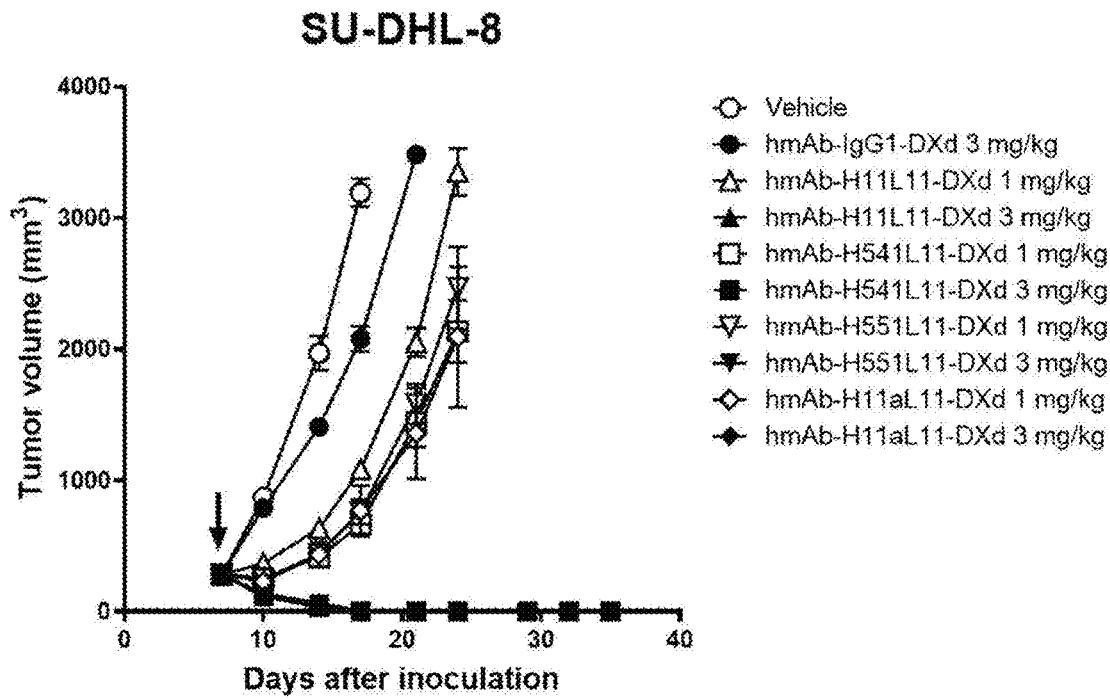
[Figure 11]
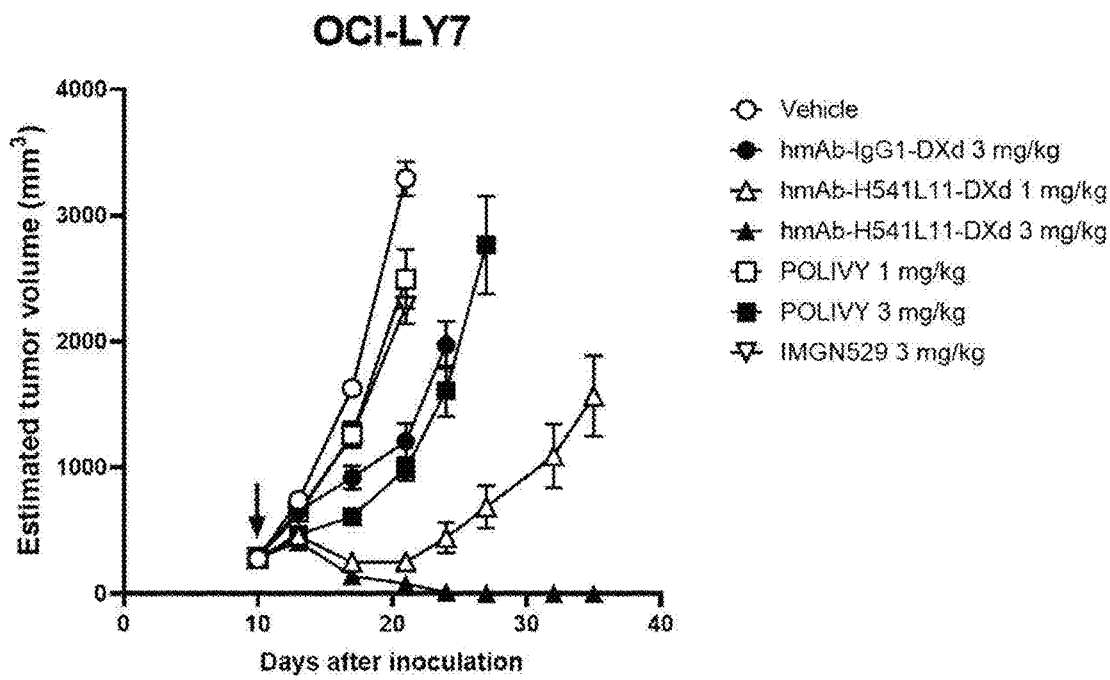

[Figure 12]
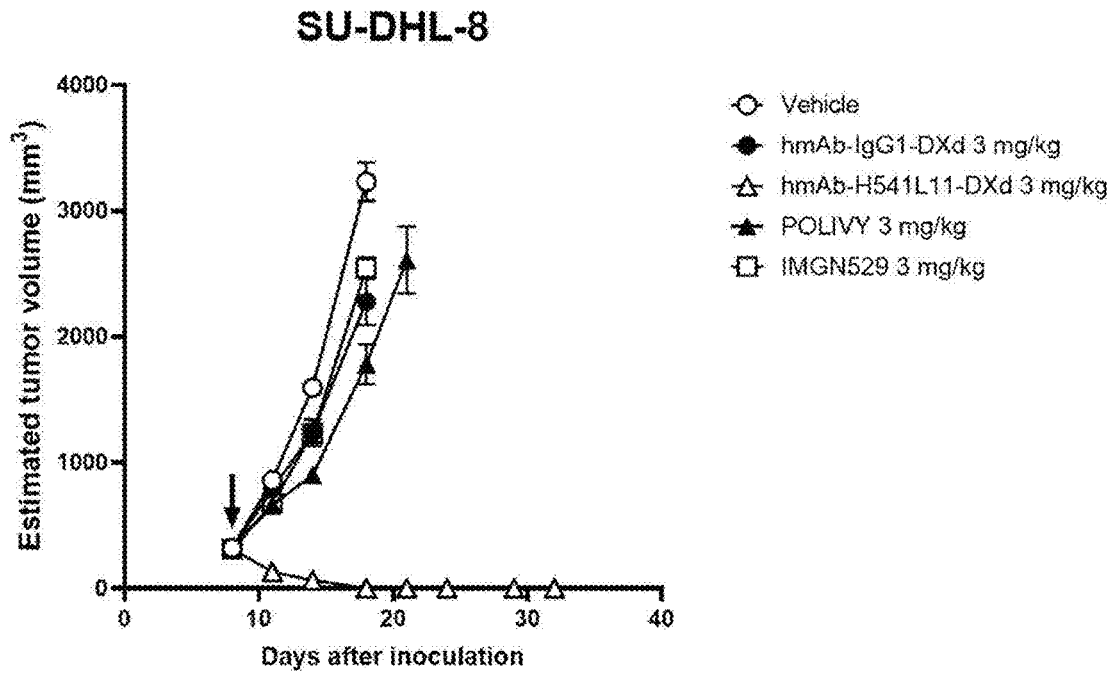
[Figure 13]
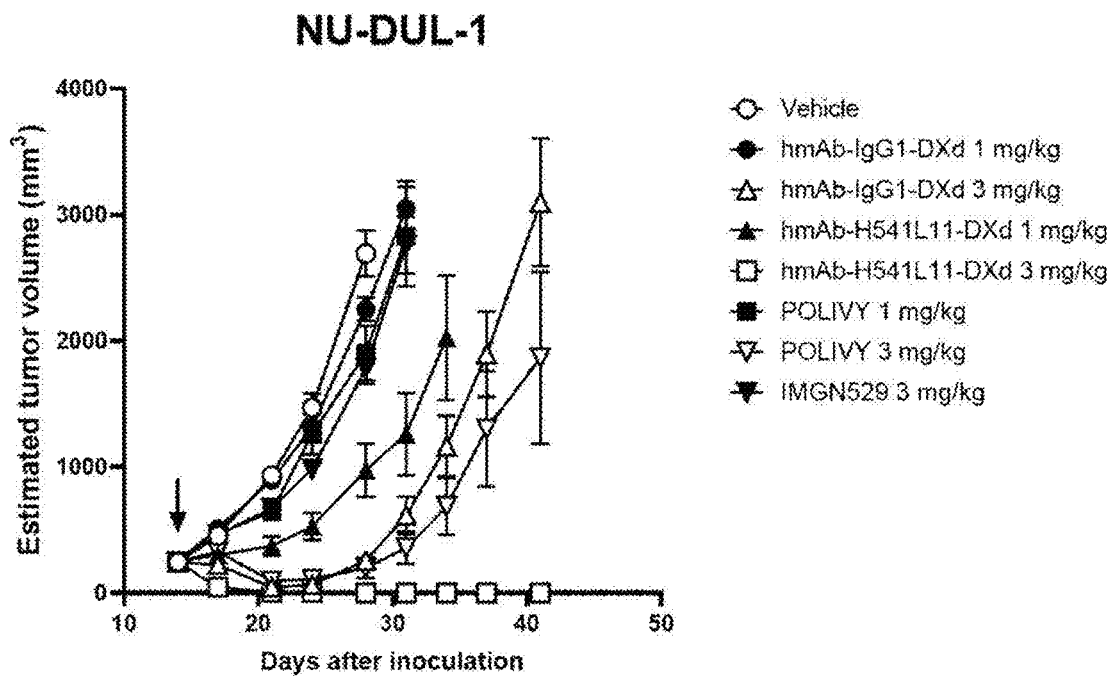

[Figure 14]
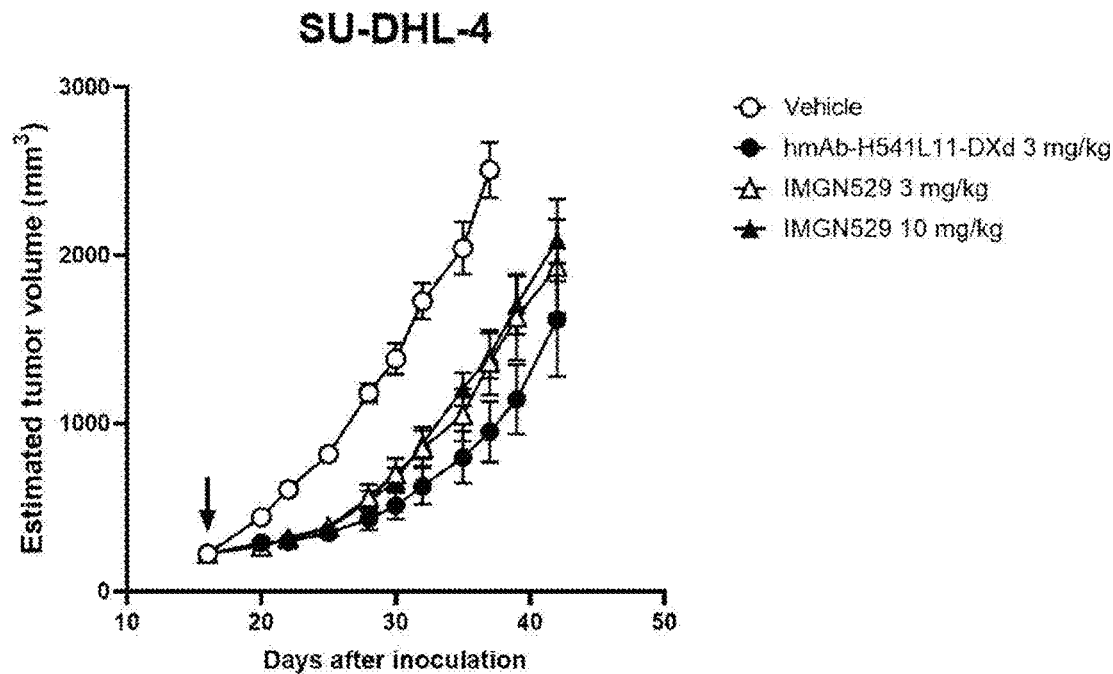
[Figure 15]
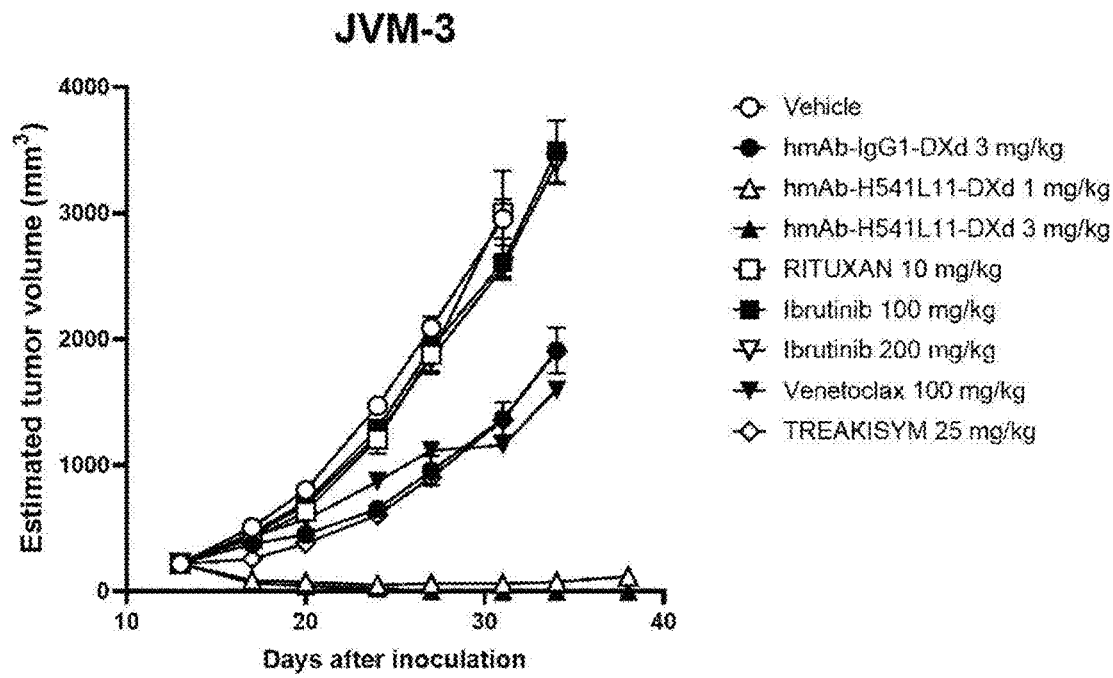

[Figure 16]
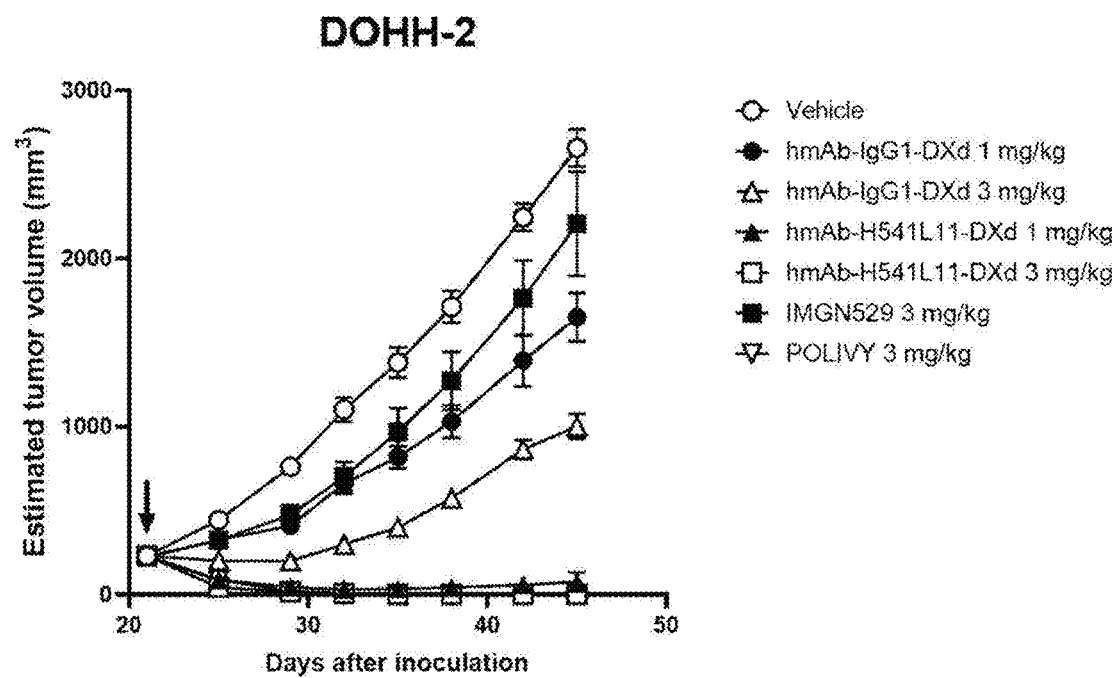

SEQUENCE LISTING

```
Sequence total quantity: 24
SEQ ID NO: 1              moltype = DNA  length = 702
FEATURE                   Location/Qualifiers
misc_feature              1..702
                          note = nucleotide sequence coding hmAb-L11 light chain
source                    1..702
                          mol_type = other DNA
                          organism = synthetic construct
CDS                       1..702
                          protein_id = 2
                          translation = MVLQTQVFISLLLWISGAYGDIQMTQSPSSLSASVGDRVTITCKAS
                          QDVSTAVDWYQQKPGKAPKLLINWASTRHTGVPSRFSGSGSGTDFTLTISSLQPEDFAT
                          YYCRQHYSTPFTFGQGTKVEIKRTVAAPSVFIFPPSDEQLKSGTASVVCLLNNFYPREA
                          KVQWKVDNALQSGNSQESVTEQDSKDSTYSLSSTLTLSKADYEKHKVYACEVTHQGLSS
                          PVTKSFNRGEC
SEQUENCE: 1
atggtgctgc agacccaggt gttcatctcc ctgctgctgt ggatctccgg cgcgtacggc  60
gatatccaga tgacacagag ccctagcagc ctgtctgcca gcgtgggaga cagagtgacc  120
atcacatgca aggccagcca ggatgtgtcc accgccgtgg attggtatca gcagaagcct  180
ggcaaggccc ctaagctgct gatcaactgg gccagcacaa gacacacagg cgtgcccagc  240
agattttctg gcagcggctc tggcaccgac ttcaccctga ccatatctag cctgcagcct  300
gaggacttcg ccacctacta ctgcagacag cactacagca ccccttttca ctttggccag  360
ggcaccaagg tggaaatcaa gcgtacggtg gccgccccct ccgtgttcat cttcccccca  420
tccgacgagc agctgaagtc cggcaccgcc tccgtggtgt gcctgctgaa taacttctac  480
cccagagagg ccaaggtgca gtggaaggtg gacaacgccc tgcagtccgg gaactcccag  540
gagagcgtga ccgagcagga cagcaaggac agcacctaca gcctgagcag caccctgacc  600
ctgagcaaag ccgactacga gaagcacaag gtgtacgcct gcgaggtgac ccaccagggc  660
ctgagctccc ccgtcaccaa gagcttcaac aggggggagt gt                    702

SEQ ID NO: 2              moltype = AA  length = 234
FEATURE                   Location/Qualifiers
REGION                    1..234
                          note = Synthetic Construct
source                    1..234
                          mol_type = protein
                          organism = synthetic construct
SEQUENCE: 2
MVLQTQVFIS LLLWISGAYG DIQMTQSPSS LSASVGDRVT ITCKASQDVS TAVDWYQQKP  60
GKAPKLLINW ASTRHTGVPS RFSGSGSGTD FTLTISSLQP EDFATYYCRQ HYSTPFTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234
```

```
SEQ ID NO: 3              moltype = DNA  length = 1404
FEATURE                   Location/Qualifiers
misc_feature              1..1404
                          note = nucleotide sequence coding hmAb-H11 heavy chain
source                    1..1404
                          mol_type = other DNA
                          organism = synthetic construct
CDS                       1..1404
                          protein_id = 4
                          translation = MKHLWFFLLLVAAPRWVLSEVQLVQSGAEVKKPGASVKVSCKASGY
                          SFTDYNMYWVRQAPGQSLEWMGYIDPYNGDTTYNQKFQGRVTITADTSTSTAYMELSSL
                          RSEDTAVYYCARSPYGHYAMDYWGQGTLVTVSSASTKGPSVFPLAPSSKSTSGGTAALG
                          CLVKDYFPEPVTVSWNSGALTSGVHTFPAVLQSSGLYSLSSVVTVPSSSLGTQTYICNV
                          NHKPSNTKVDKKVEPKSCDKTHTCPPCPAPELLGGPSVFLFPPKPKDTLMISRTPEVTC
                          VVVDVSHEDPEVKFNWYVDGVEVHNAKTKPREEQYNSTYRVVSVLTVLHQDWLNGKEYK
                          CKVSNKALPAPIEKTISKAKGQPREPQVYTLPPSREEMTKNQVSLTCLVKGFYPSDIAV
                          EWESNGQPENNYKTTPPVLDSDGSFFLYSKLTVDKSRWQQGNVFSCSVMHEALHNHYTQ
                          KSLSLSPGK
SEQUENCE: 3
atgaaacacc tgtggttctt cctcctgctg gtggcagctc ccagatgggt gctgagcgaa   60
gttcagctgg ttcagtctgg cgccgaagtg aagaaacctg gcgcctctgt gaaggtgtcc  120
tgcaaggcca gcggctacag cttcaccgac tacaacatgt actgggtccg acaggccct  180
ggccagtctc ttgagtggat gggctacatc gaccctaca acggcgacac cacctacaac  240
cagaaattcc agggcagagt gaccatcacc gccgacacct acaagcac gcctacatg    300
gaactgagca gcctgagaag cgaggacacc gccgtgtact actgcgccag atctccttac  360
ggccactacg ccatggatta ctggggccag ggaaccctgg tcacagttag ctcagcctcc  420
accaagggcc caagcgtctt cccccttggca ccctcctcca agagcacctc tggcggcaca  480
gccgccctgg gctgcctggt caaggactac ttccccgaac ccgtgaccgt gagctggaac  540
tcaggcgccc tgaccagcgg cgtgcacacc ttccccgctg tcctgcagtc ctcaggactg  600
tactccctca gcagcgtggt gaccgtgccc tccagcagct tgggcaccca gacctacatc  660
tgcaacgtga atcacaagcc cagcaacacc aaggtggaca gaaaggttga gcccaaatct  720
tgtgacaaaa ctcacacatg cccaccctgc ccagcacctg aactcctggg gggaccctca  780
gtcttcctct tccccccaaa acccaaggac accctcatga tctcccggac ccctgaggtc  840
acatgcgtgg tggtggacgt gagccacgaa gaccctgagg tcaagttcaa ctggtacgtg  900
gacggcgtgg aggtgcataa tgccaagaca aagcccgg aggagcagta caacagcacg  960
taccgggtgg tcagcgtcct caccgtcctg caccaggact ggctgaatgg caaggagtac 1020
aagtgcaagg tctccaacaa agccctccca gcccccatcg agaaaaccat ctccaaagcc 1080
aaagggcagc ccccgggaacc acaggtgtac accctgcccc catcccggga ggagatgacc 1140
aagaaccagg tcagcctgac ctgcctggtc aaaggcttct atcccagcga catcgccgtg 1200
gagtgggaga gcaatggcca gcccgagaac aactacaaga ccaccctcc cgtgctggac 1260
tccgacggct ccttcttcct ctacagcaag ctcaccgtgg acaagagcag gtggcagcag 1320
ggcaacgtct tctcatgctc cgtgatgcat gaggctctgc acaaccacta cacccagaag 1380
agcctctccc tgtctcccgg caaa                                        1404

SEQ ID NO: 4              moltype = AA  length = 468
FEATURE                   Location/Qualifiers
REGION                    1..468
                          note = Synthetic Construct
source                    1..468
                          mol_type = protein
                          organism = synthetic construct
SEQUENCE: 4
MKHLWFFLLL VAAPRWVLSE VQLVQSGAEV KKPGASVKVS CKASGYSFTD YNMYWVRQAP   60
GQSLEWMGYI DPYNGDTTYN QKFQGRVTIT ADTSTSTAYM ELSSLRSEDT AVYYCARSPY  120
GHYAMDYWGQ GTLVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
CDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSREEMT KNQVSLTCLV KGFYPSDIAV EWESNGQPEN NYKTTPPVLD  420
SDGSFFLYSK LTVDKSRWQQ GNVFSCSVMH EALHNHYTQK SLSLSPGK               468

SEQ ID NO: 5              moltype = DNA  length = 1404
FEATURE                   Location/Qualifiers
misc_feature              1..1404
                          note = nucleotide sequence coding hmAb-H541 heavy chain
source                    1..1404
                          mol_type = other DNA
                          organism = synthetic construct
CDS                       1..1404
                          protein_id = 6
                          translation = MKHLWFFLLLVAAPRWVLSEVQLVQSGAEVKKPGASVKVSCKASGY
                          SFTDYNMYWVRQAPGQSLEWMGYIDPYNGDTTYNQKFQGRVTMTRDTSISTAYMELSRL
                          RSDDTAVYYCARSPYGHYAMDYWGQGTTVTVSSASTKGPSVFPLAPSSKSTSGGTAALG
                          CLVKDYFPEPVTVSWNSGALTSGVHTFPAVLQSSGLYSLSSVVTVPSSSLGTQTYICNV
                          NHKPSNTKVDKKVEPKSCDKTHTCPPCPAPELLGGPSVFLFPPKPKDTLMISRTPEVTC
                          VVVDVSHEDPEVKFNWYVDGVEVHNAKTKPREEQYNSTYRVVSVLTVLHQDWLNGKEYK
                          CKVSNKALPAPIEKTISKAKGQPREPQVYTLPPSREEMTKNQVSLTCLVKGFYPSDIAV
                          EWESNGQPENNYKTTPPVLDSDGSFFLYSKLTVDKSRWQQGNVFSCSVMHEALHNHYTQ
```

```
                    KSLSLSPGK
SEQUENCE: 5
atgaaacacc tgtggttctt cctcctgctg gtggcagctc ccagatgggt gctgagcgaa    60
gtgcagctgg ttcagtctgg cgccgaagtg aaaaagcctg gcgcctctgt gaaggtgtcc   120
tgcaaggcca gcggctacag cttcaccgac tacaacatgt actgggtccg acaggcccct   180
ggccagtctc ttgagtggat gggctacatc gaccccctaca acggcgacac cacctacaac   240
cagaaattcc agggcagagt gaccatgacc agagacacca gcatcagcac cgcctacatg   300
gaactgagcc ggctgagatc cgatgacacc gccgtgtact actgcgccag atctccttac   360
ggccactacg ccatggatta ctggggccag ggcaccacag tgacagttag ctcagcctca   420
accaagggcc caagcgtctt ccccctggca ccctcctcca agagcacctc tggcggcaca   480
gccgccctgg gctgcctggt caaggactac ttccccgaac cgtgaccgt gagctggaac   540
tcaggcgccc tgaccagcgg cgtgcacacc ttccccgctg cctgcagtc ctcaggactc   600
tactccctca gcagcgtggt gaccgtgccc tccagcagct gggcaccca gacctacatc   660
tgcaacgtga atcacaagcc cagcaacacc aaggtggaca agaaggttga gcccaaatct   720
tgtgacaaaa ctcacacatg cccaccctgc ccagcacctg aactcctggg gggaccctca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccccggg aggagcagta caacagcacg   960
taccgggtgg tcagcgtcct caccgtcctg caccaggact ggctgaatgg caaggagtac  1020
aagtgcaagg tctccaacaa agccctccca gcccccatcg agaaaaccat ctccaaagcc  1080
aaaggccagc ccgggaacc acaggtgtac accctgcccc catcccggga ggagatgacc  1140
aagaaccagg tcagcctgac ctgcctggtc aaaggcttct atcccagcga catcgccgtg  1200
gagtgggaga gcaatggcca gcccgagaac aactacaaga ccaccctcc cgtgctggac  1260
tccgacggct ccttcttcct ctacagcaag ctcaccgtgg acaagagcag gtggcagcag  1320
ggcaacgtct tctcatgctc cgtgatgcat gaggctctgc acaaccacta cacccagaag  1380
agcctctccc tgtctcccgg caaa                                         1404

SEQ ID NO: 6            moltype = AA  length = 468
FEATURE                 Location/Qualifiers
REGION                  1..468
                        note = Synthetic Construct
source                  1..468
                        mol_type = protein
                        organism = synthetic construct
SEQUENCE: 6
MKHLWFFLLL VAAPRWVLSE VQLVQSGAEV KKPGASVKVS CKASGYSFTD YNMYWVRQAP    60
GQSLEWMGYI DPYNGDTTYN QKFQGRVTMT RDTSISTAYM ELSRLRSDDT AVYYCARSPY   120
GHYAMDYWGQ GTTVTVSSAS TKGPSVFPLA PSSKSTSGGT AALGCLVKDY FPEPVTVSWN   180
SGALTSGVHT FPAVLQSSGL YSLSSVVTVP SSSLGTQTYI CNVNHKPSNT KVDKKVEPKS   240
CDKTHTCPPC PAPELLGGPS VFLFPPKPKD TLMISRTPEV TCVVVDVSHE DPEVKFNWYV   300
DGVEVHNAKT KPREEQYNST YRVVSVLTVL HQDWLNGKEY KCKVSNKALP APIEKTISKA   360
KGQPREPQVY TLPPSREEMT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGK                468

SEQ ID NO: 7            moltype = DNA  length = 1404
FEATURE                 Location/Qualifiers
misc_feature            1..1404
                        note = nucleotide sequence coding hmAb-H551 heavy chain
source                  1..1404
                        mol_type = other DNA
                        organism = synthetic construct
CDS                     1..1404
                        protein_id = 8
                        translation = MKHLWFFLLLVAAPRWVLSEVQLVQSGAEVKKPGASVKVSCKASGY
                        SFTDYNMYWVRQAPGQSLEWMGYIDPYNGDTTYNQKFQGRVTMTRDTSSSTAYMELSRL
                        RSDDTAVYYCARSPYGHYAMDYWGQGTTVTVSSASTKGPSVFPLAPSSKSTSGGTAALG
                        CLVKDYFPEPVTVSWNSGALTSGVHTFPAVLQSSGLYSLSSVVTVPSSSLGTQTYICNV
                        NHKPSNTKVDKKVEPKSCDKTHTCPPCPAPELLGGPSVFLFPPKPKDTLMISRTPEVTC
                        VVVDVSHEDPEVKFNWYVDGVEVHNAKTKPREEQYNSTYRVVSVLTVLHQDWLNGKEYK
                        CKVSNKALPAPIEKTISKAKGQPREPQVYTLPPSREEMTKNQVSLTCLVKGFYPSDIAV
                        EWESNGQPENNYKTTPPVLDSDGSFFLYSKLTVDKSRWQQGNVFSCSVMHEALHNHYTQ
                        KSLSLSPGK
SEQUENCE: 7
atgaaacacc tgtggttctt cctcctgctg gtggcagctc ccagatgggt gctgagcgaa    60
gtgcagctgg ttcagtctgg cgccgaagtg aaaaagcctg gcgcctctgt gaaggtgtcc   120
tgcaaggcca gcggctacag cttcaccgac tacaacatgt actgggtccg acaggcccct   180
ggccagtctc ttgagtggat gggctacatc gaccccctaca acggcgacac cacctacaac   240
cagaaattcc agggcagagt gaccatgacc agagacacca gcagcagcac cgcctacatg   300
gaactgagca ggctgagaag cgacgacacc gccgtgtact actgcgcgag atctccttac   360
ggccactacg ccatggatta ctggggccag ggcaccacag tgacagttag ctcagcctcc   420
accaagggcc caagcgtctt ccccctggca ccctcctcca agagcacctc tggcggcaca   480
gccgccctgg gctgcctggt caaggactac ttccccgaac cgtgaccgt gagctggaac   540
tcaggcgccc tgaccagcgg cgtgcacacc ttccccgctg cctgcagtc ctcaggactc   600
tactccctca gcagcgtggt gaccgtgccc tccagcagct gggcaccca gacctacatc   660
tgcaacgtga atcacaagcc cagcaacacc aaggtggaca agaaggttga gcccaaatct   720
tgtgacaaaa ctcacacatg cccaccctgc ccagcacctg aactcctggg gggaccctca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccccggg aggagcagta caacagcacg   960
```

-continued

```
taccgggtgg tcagcgtcct caccgtcctg caccaggact ggctgaatgg caaggagtac    1020
aagtgcaagg tctccaacaa agccctccca gcccccatcg agaaaaccat ctccaaagcc    1080
aaaggccagc ccgggaacc acaggtgtac accctgcccc catcccggga ggagatgacc    1140
aagaaccagg tcagcctgac ctgcctggtc aaaggcttct atcccagcga catcgccgtg    1200
gagtgggaga gcaatggcca gcccgagaac aactacaacc caccccctcc cgtgctggac    1260
tccgacggct ccttcttcct ctacagcaag ctcaccgtgg acaagagcag gtggcagcag    1320
ggcaacgtct tctcatgctc cgtgatgcat gaggctctgc acaaccacta cacccagaag    1380
agcctctccc tgtctcccgg caaa                                           1404
```

| SEQ ID NO: 8 | moltype = AA length = 468 |
|---|---|
| FEATURE | Location/Qualifiers |
| REGION | 1..468 |
| | note = Synthetic Construct |
| source | 1..468 |
| | mol_type = protein |
| | organism = synthetic construct |

SEQUENCE: 8
```
MKHLWFFLLL VAAPRWVLSE VQLVQSGAEV KKPGASVKVS CKASGYSFTD YNMYWVRQAP     60
GQSLEWMGYI DPYNGDTTYN QKFQGRVTMT RDTSSSTAYM ELSRLRSDDT AVYYCARSPY    120
GHYAMDYWGQ GTTVTVSSAS TKGPSVFPLA PSSKSTSGGT AALGCLVKDY FPEPVTVSWN    180
SGALTSGVHT FPAVLQSSGL YSLSSVVTVP SSSLGTQTYI CNVNHKPSNT KVDKKVEPKS    240
CDKTHTCPPC PAPELLGGPS VFLFPPKPKD TLMISRTPEV TCVVVDVSHE DPEVKFNWYV    300
DGVEVHNAKT KPREEQYNST YRVVSVLTVL HQDWLNGKEY KCKVSNKALP APIEKTISKA    360
KGQPREPQVY TLPPSREEMT KNQVSLTCLV KGFYPSDIAV EWESNGQPEN NYKTTPPVLD    420
SDGSFFLYSK LTVDKSRWQQ GNVFSCSVMH EALHNHYTQK SLSLSPGK                 468
```

| SEQ ID NO: 9 | moltype = DNA length = 1404 |
|---|---|
| FEATURE | Location/Qualifiers |
| misc_feature | 1..1404 |
| | note = nucleotide sequence coding hmAb-H11a heavy chain |
| source | 1..1404 |
| | mol_type = other DNA |
| | organism = synthetic construct |
| CDS | 1..1404 |
| | protein_id = 10 |
| | translation = MKHLWFFLLLVAAPRWVLSEVQLVQSGAEVKKPGASVKVSCKASGY |
| | SFTDYNMYWVRQAPGQSLEWMGYIDPYNGDTTYNQKFQGRVTITADKSKSTAYMELSSL |
| | RSEDTAVYYCARSPYGHYAMDYWGQGTLVTVSSASTKGPSVFPLAPSSKSTSGGTAALG |
| | CLVKDYFPEPVTVSWNSGALTSGVHTFPAVLQSSGLYSLSSVVTVPSSSLGTQTYICNV |
| | NHKPSNTKVDKKVEPKSCDKTHTCPPCPAPELLGGPSVFLFPPKPKDTLMISRTPEVTC |
| | VVVDVSHEDPEVKFNWYVDGVEVHNAKTKPREEQYNSTYRVVSVLTVLHQDWLNGKEYK |
| | CKVSNKALPAPIEKTISKAKGQPREPQVYTLPPSREEMTKNQVSLTCLVKGFYPSDIAV |
| | EWESNGQPENNYKTTPPVLDSDGSFFLYSKLTVDKSRWQQGNVFSCSVMHEALHNHYTQ |
| | KSLSLSPGK |

SEQUENCE: 9
```
atgaaacacc tgtggttctt cctcctgctg gtggcagctc ccagatgggt gctgagcgaa     60
gtgcagctgg tccagtctgg cgccgaagtg aaaaagcctg gcgcctctgt gaaggtgtcc    120
tgcaaggcca gcggctacag cttcaccgac tacaacatgt actgggtccg acaggcccct    180
ggccagtctc ttgagtggat gggctacatc gaccgctaca acggcgacac cacctacaac    240
cagaaattcc agggcagagt gaccatcacc gccgacaaga gcaagagcac cgcctacatg    300
gaactgagca gcctgagaag cgaggacacc gccgtgtact actgcgccag atctccttac    360
ggccactacg ccatggatta ctggggccag ggcacactgg ttaccgttag ctcagcctcc    420
accaagggcc caagcgtctt ccccctggca ccctcctcca agagcacctc tggcggcaca    480
gccgccctgg gctgcctggt caaggactac ttccccgaac ccgtgaccgt gagctggaac    540
tcaggcgccc tgaccagcgg cgtgcacacc ttccccgctg tcctgcagtc ctcaggactc    600
tactccctca gcagcgtggt gaccgtgccc tccagcagct tgggcaccca gacctacatc    660
tgcaacgtga atcacaagcc cagcaacacc aaggtggaca gaaaggttga gcccaaatct    720
tgtgacaaaa ctcacacatg cccaccctgc ccagcacctg aactcctggg gggacccta    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagcccggg aggagcagta caacagcacg    960
taccgggtgg tcagcgtcct caccgtcctg caccaggact ggctgaatgg caaggagtac    1020
aagtgcaagg tctccaacaa agccctccca gcccccatcg agaaaaccat ctccaaagcc    1080
aaaggccagc ccgggaacc acaggtgtac accctgcccc catcccggga ggagatgacc    1140
aagaaccagg tcagcctgac ctgcctggtc aaaggcttct atcccagcga catcgccgtg    1200
gagtgggaga gcaatggcca gcccgagaac aactacaaga ccccctcc cgtgctggac     1260
tccgacggct ccttcttcct ctacagcaag ctcaccgtgg acaagagcag gtggcagcag    1320
ggcaacgtct tctcatgctc cgtgatgcat gaggctctgc acaaccacta cacccagaag    1380
agcctctccc tgtctcccgg caaa                                           1404
```

| SEQ ID NO: 10 | moltype = AA length = 468 |
|---|---|
| FEATURE | Location/Qualifiers |
| REGION | 1..468 |
| | note = Synthetic Construct |
| source | 1..468 |
| | mol_type = protein |
| | organism = synthetic construct |

SEQUENCE: 10
```
MKHLWFFLLL VAAPRWVLSE VQLVQSGAEV KKPGASVKVS CKASGYSFTD YNMYWVRQAP     60
```

```
GQSLEWMGYI DPYNGDTTYN QKFQGRVTIT ADKSKSTAYM ELSSLRSEDT AVYYCARSPY      120
GHYAMDYWGQ GTLVTVSSAS TKGPSVFPLA PSSKSTSGGT AALGCLVKDY FPEPVTVSWN      180
SGALTSGVHT FPAVLQSSGL YSLSSVVTVP SSSLGTQTYI CNVNHKPSNT KVDKKVEPKS      240
CDKTHTCPPC PAPELLGGPS VFLFPPKPKD TLMISRTPEV TCVVVDVSHE DPEVKFNWYV      300
DGVEVHNAKT KPREEQYNST YRVVSVLTVL HQDWLNGKEY KCKVSNKALP APIEKTISKA      360
KGQPREPQVY TLPPSREEMT KNQVSLTCLV KGFYPSDIAV EWESNGQPEN NYKTTPPVLD      420
SDGSFFLYSK LTVDKSRWQQ GNVFSCSVMH EALHNHYTQK SLSLSPGK                   468

SEQ ID NO: 11              moltype = DNA   length = 449
FEATURE                    Location/Qualifiers
misc_feature               1..449
                           note = nucleotide fragment comprising nucleotide sequences
                             coding humanlight chain signal sequence and human kappa
                             light chain constantregion
source                     1..449
                           mol_type = other DNA
                           organism = synthetic construct
SEQUENCE: 11
gcctccggac tctagagcca ccatggtgct gcagacccag gtgttcatct ccctgctgct      60
gtggatctcc ggcgcgtacg gcgatatcgt gatgattaaa cgtacggtgg ccgcccctc     120
cgtgttcatc ttccccccct ccgacgagca gctgaagtcc ggcaccgcct ccgtggtgtg    180
cctgctgaat aacttctacc ccagagaggc caaggtgcag tggaaggtgg acaacgccct    240
gcagtccggg aactcccagg agagcgtgac cgagcaggac agcaaggaca gcacctacag    300
cctgagcagc accctgaccc tgagcaaagc cgactacgag aagcacaagg tgtacgcctg    360
cgaggtgacc caccagggcc tgagctcccc cgtcaccaag agcttcaaca gggggagtg     420
ttaggggccc gtttaaacgg gggaggcta                                       449

SEQ ID NO: 12              moltype = DNA   length = 366
FEATURE                    Location/Qualifiers
misc_feature               1..366
                           note = nucleotide sequence coding variable region of
                             hmAb-L11 lightchain
source                     1..366
                           mol_type = other DNA
                           organism = synthetic construct
SEQUENCE: 12
ctgtggatct ccggcgcgta cggcgatatc cagatgacac agagccctag cagcctgtct     60
gccagcgtgg gagacagagt gaccatcaca tgcaaggcca gcaggatgt gtccaccagc    120
gtggattggt atcagcagaa gcctggcaag gcccctaagc tgctgatcaa ctgggccagc    180
acaagacaca caggcgtgcc cagcagattt tctggcagcg gctctggcac cgacttcacc    240
ctgaccatat ctagcctgca gcctgaggac ttcgccacct actactgcag acagcactac    300
agcacccctt tcacctttgg ccagggcacc aaggtggaaa tcaagcgtac ggtggccgcc    360
ccctcc                                                                366

SEQ ID NO: 13              moltype = DNA   length = 1117
FEATURE                    Location/Qualifiers
misc_feature               1..1117
                           note = nucleotide fragment comprising nucleotide sequences
                             coding humanheavy chain signal sequence and human G1 heavy
                             chain constantregion
source                     1..1117
                           mol_type = other DNA
                           organism = synthetic construct
SEQUENCE: 13
gggtctagag ccaccatgaa acacctgtgg ttcttcctcc tgctggtggc agctcccaga      60
tgggtgctga gccaggtgca attgtgcagg cggttagctc agcctccacc aagggcccaa    120
gcgtcttccc cctggcaccc tcctccaaga gcacctctgg cggcacagcc gccctgggct    180
gcctggtcaa ggactacttc cccgaacccg tgaccgtgag ctggaactca ggcgccctga    240
ccagcggcgt gcacaccttc ccggctgtcc tgcagtcctc aggactctac tccctcagca    300
gcgtggtgac cgtgccctcc agcagcttgg gcacccagac ctacatctgc aacgtgaatc    360
acaagcccag caacaccaag gtggacaaga aggttgagcc caaatcttgt gacaaaactc    420
acacatgccc accctgccca gcacctgaac tcctgggggg accctcagtc ttcctcttcc    480
ccccaaaacc caaggacacc ctcatgatct cccggacccc tgaggtcaca tgcgtggtgg    540
tggacgtgag ccacgaagac cctgaggtca agttcaactg gtacgtggac ggcgtggagg    600
tgcataatgc caagacaaag ccgcgggagg agcagtacaa cagcacgtac cgggtggtca    660
gcgtcctcac cgtcctgcac caggactggc tgaatggcaa ggagtacaag tgcaaggtct    720
ccaacaaagc cctcccagcc cccatcgaga aaaccatctc caaagccaaa ggccagcccc    780
gggaaccaca ggtgtacacc ctgccccat cccgggagga tgagctgacc aaccaggtca    840
gcctgacctg cctggtcaaa ggcttctatc ccagcgacat cgccgtggag tgggagagca    900
atggccagcc cgagaacaac tacaagacca cccctcccgt gctggactcc gacggctcct    960
tcttcctcta cagcaagctc accgtggaca gagcaggtg gcagcaggc aacgtcttct    1020
catgctccgt gatgcatgag gctctgcaca accactacac ccagaagagc ctctccctgt   1080
ctcccggcaa atgagatatc gggcccgttt aaacggg                            1117

SEQ ID NO: 14              moltype = DNA   length = 396
FEATURE                    Location/Qualifiers
misc_feature               1..396
                           note = nucleotide sequence coding variable region of
                             hmAb-H11 heavychain
```

|  |  |  |
|---|---|---|
| source | 1..396 | |
| | mol_type = other DNA | |
| | organism = synthetic construct | |

SEQUENCE: 14
```
agctcccaga tgggtgctga gcgaagttca gctggttcag tctggcgccg aagtgaagaa   60
acctggcgcc tctgtgaagg tgtcctgcaa ggccagcggc tacagcttca ccgactacaa  120
catgtactgg gtccgacagg cccctggcca gtctcttgag tggatgggct acatcgaccc  180
ctacaacggc gacaccacct acaaccagaa attccagggc agagtgacca tcaccgcgga  240
cacctctaca agcaccgcct acatggaact gagcagcctg agaagcgagg acaccgccgt  300
gtactactgc gccagatctc cttacggcca ctacgccatg gattactggg gccagggaac  360
cctggtcaca gttagctcag cctccaccaa gggccc                             396
```

| | | |
|---|---|---|
| SEQ ID NO: 15 | moltype = DNA length = 396 | |
| FEATURE | Location/Qualifiers | |
| misc_feature | 1..396 | |
| | note = nucleotide sequence coding variable region of hmAb-H541 heavychain | |
| source | 1..396 | |
| | mol_type = other DNA | |
| | organism = synthetic construct | |

SEQUENCE: 15
```
agctcccaga tgggtgctga gcgaagtgca gctggttcag tctggcgccg aagtgaaaaa   60
gcctggcgcc tctgtgaagg tgtcctgcaa ggccagcggc tacagcttca ccgactacaa  120
catgtactgg gtccgacagg cccctggcca gtctcttgag tggatgggct acatcgaccc  180
ctacaacggc gacaccacct acaaccagaa attccagggc agagtgacca tgaccagaga  240
caccagcatc agcaccgcct acatggaact gagccggctg agatccgatg acaccgccgt  300
gtactactgc gccagatctc cttacggcca ctacgccatg gattactggg gccagggcac  360
cacagtgaca gttagctcag cctccaccaa gggccc                             396
```

| | | |
|---|---|---|
| SEQ ID NO: 16 | moltype = DNA length = 396 | |
| FEATURE | Location/Qualifiers | |
| misc_feature | 1..396 | |
| | note = nucleotide sequence coding variable region of hmAb-H551 heavychain | |
| source | 1..396 | |
| | mol_type = other DNA | |
| | organism = synthetic construct | |

SEQUENCE: 16
```
agctcccaga tgggtgctga gcgaagtgca gctggttcag tctggcgccg aagtgaaaaa   60
gcctggcgcc tctgtgaagg tgtcctgcaa ggccagcggc tacagcttca ccgactacaa  120
catgtactgg gtccgacagg cccctggcca gtctcttgag tggatgggct acatcgaccc  180
ctacaacggc gacaccacct acaaccagaa attccagggc agagtgacca tgaccagaga  240
caccagcagc agcaccgcct acatggaact gagcagactg agaagcgacg acaccgccgt  300
gtactactgc gccagatctc cttacggcca ctacgccatg gattactggg gccagggcac  360
cacagtgaca gttagctcag cctccaccaa gggccc                             396
```

| | | |
|---|---|---|
| SEQ ID NO: 17 | moltype = DNA length = 396 | |
| FEATURE | Location/Qualifiers | |
| misc_feature | 1..396 | |
| | note = nucleotide sequence coding variable region of hmAb-H11a heavychain | |
| source | 1..396 | |
| | mol_type = other DNA | |
| | organism = synthetic construct | |

SEQUENCE: 17
```
agctcccaga tgggtgctga gcgaagtgca gctggttcag tctggcgccg aagtgaaaaa   60
gcctggcgcc tctgtgaagg tgtcctgcaa ggccagcggc tacagcttca ccgactacaa  120
catgtactgg gtccgacagg cccctggcca gtctcttgag tggatgggct acatcgaccc  180
ctacaacggc gacaccacct acaaccagaa attccagggc agagtgacca tcaccgcgga  240
caagagcaag agcaccgcct acatggaact gagcagcctg agaagcgagg acaccgccgt  300
gtactactgc gccagatctc cttacggcca ctacgccatg gattactggg gccagggcac  360
actggttacc gttagctcag cctccaccaa gggccc                             396
```

| | | |
|---|---|---|
| SEQ ID NO: 18 | moltype = AA length = 281 | |
| FEATURE | Location/Qualifiers | |
| source | 1..281 | |
| | mol_type = protein | |
| | organism = Homo sapiens | |

SEQUENCE: 18
```
MSAQESCLSL IKYFLFVFNL FFFVLGSLIF CFGIWILIDK TSFVSFVGLA FVPLQIWSKV   60
LAISGIFTMG IALLGCVGAL KELRCLLGLY FGMLLLLFAT QITLGILIST QRAQLERSLR  120
DVVEKTIQKY GTNPEETAAE ESWDYVQFQL RCCGWHYPQD WFQVLILRGN GSEAHRVPCS  180
CYNLSATNDS TILDKVILPQ LSRLGHLARS RHSADICAVP AESHIYREGC AQGLQKWLHN  240
NLISIVGICL GVGLLELGFM TLSIFLCRNL DHVYNRLARY R                      281
```

| | | |
|---|---|---|
| SEQ ID NO: 19 | moltype = AA length = 11 | |
| FEATURE | Location/Qualifiers | |
| REGION | 1..11 | |
| | note = CDRL1 sequence of humanized anti-CD37 antibody | |

| | | |
|---|---|---|
| source | 1..11<br>mol_type = protein<br>organism = synthetic construct | |
| SEQUENCE: 19<br>KASQDVSTAV D | | 11 |

| | | |
|---|---|---|
| SEQ ID NO: 20<br>FEATURE<br>REGION | moltype = AA   length = 7<br>Location/Qualifiers<br>1..7<br>note = CDRL2 sequence of humanized anti-CD37 antibody | |
| source | 1..7<br>mol_type = protein<br>organism = synthetic construct | |
| SEQUENCE: 20<br>WASTRHT | | 7 |

| | | |
|---|---|---|
| SEQ ID NO: 21<br>FEATURE<br>REGION | moltype = AA   length = 9<br>Location/Qualifiers<br>1..9<br>note = CDRL3 sequence of humanized anti-CD37 antibody | |
| source | 1..9<br>mol_type = protein<br>organism = synthetic construct | |
| SEQUENCE: 21<br>RQHYSTPFT | | 9 |

| | | |
|---|---|---|
| SEQ ID NO: 22<br>FEATURE<br>REGION | moltype = AA   length = 10<br>Location/Qualifiers<br>1..10<br>note = CDRH1 sequence of humanized anti-CD37 antibody | |
| source | 1..10<br>mol_type = protein<br>organism = synthetic construct | |
| SEQUENCE: 22<br>GYSFTDYNMY | | 10 |

| | | |
|---|---|---|
| SEQ ID NO: 23<br>FEATURE<br>REGION | moltype = AA   length = 10<br>Location/Qualifiers<br>1..10<br>note = CDRH2 sequence of humanized anti-CD37 antibody | |
| source | 1..10<br>mol_type = protein<br>organism = synthetic construct | |
| SEQUENCE: 23<br>YIDPYNGDTT | | 10 |

| | | |
|---|---|---|
| SEQ ID NO: 24<br>FEATURE<br>REGION | moltype = AA   length = 10<br>Location/Qualifiers<br>1..10<br>note = CDRH3 sequence of humanized anti-CD37 antibody | |
| source | 1..10<br>mol_type = protein<br>organism = synthetic construct | |
| SEQUENCE: 24<br>SPYGHYAMDY | | 10 |

ANTI-CD37 ANTIBODY-DRUG CONJUGATE

CROSS-REFERENCE TO RELATED APPLICATIONS

The present application is a U.S. Bypass Continuation Application of International Patent Application No. PCT/JP2022/038604, filed Oct. 17, 2022, which claims priority to and the benefit of Japanese Patent Application No. 2021-170114, filed Oct. 18, 2021. The contents of these applications are hereby incorporated by reference in their entireties.

SEQUENCE LISTING

The instant application contains a Sequence Listing which has been submitted in XML format via Patent Center and is hereby incorporated by reference in its entirety. Said XML copy, is named 098065-0384_SL.xml and is 48 kb in size.

TECHNICAL FIELD

The present invention relates to an anti-CD37 antibody binding to CD37, a method for producing the antibody, an antibody-drug conjugate comprising the antibody, an antitumor agent comprising the antibody-drug conjugate, and the like.

BACKGROUND ART

Cancers rank high in causes of death. Although the number of cancer patients is expected to increase with aging of the population, treatment needs have not yet been sufficiently satisfied. The problems of conventional chemotherapeutics are that: due to their low selectivity, these chemotherapeutics are toxic not only to tumor cells but also to normal cells and thereby have adverse reactions; and the chemotherapeutics cannot be administered in sufficient amounts and thus cannot produce their effects sufficiently. Hence, in recent years, more highly selective molecular targeting drugs and antibody drugs have been developed, which target mutations characteristic of cancer cells, molecules that are highly expressed, or specific molecules involved in malignant transformation of cells.

Rituximab is an antibody drug targeting CD20 and was approved as a therapeutic drug for B-cell non-Hodgkin's lymphoma (NHL) by the FDA in 1997 (Non Patent Literature 1). Typical mechanisms of action of rituximab are direct induction of apoptosis, ADCC (antibody-dependent cellular cytotoxicity), and CDC (complement-dependent cytotoxicity). Rituximab exhibits drastic therapeutic effects on B-cell NHL, including diffuse large B-cell lymphoma (DLBCL), expressing the target CD20, and as such, is still used widely. However, a given number of patients are unresponsive to rituximab. In addition, even patients responsive to rituximab have decreased expression of the target CD20 or acquire resistance mechanisms to each mechanism of action, ending up in recurrence in many patients, which is a challenge in treating B-cell NHL (Non Patent Literature 2). Against this backdrop, antibody drugs targeting a molecule other than CD20 or antibody drugs having a mechanism of action different from that of rituximab are under clinical development.

Antibodies are highly stable in blood, and specifically bind to their target antigens. For these reasons, a reduction in adverse reactions is expected, and a large number of antibody drugs have been developed for molecules highly expressed on the surface of cancer cells. One of the techniques that relies on the antigen-specific binding ability of antibodies can be to use an antibody-drug conjugate (ADC). An ADC is a conjugate in which an antibody that binds to an antigen expressed on the surface of cancer cells and can internalize the antigen into the cell through such binding is conjugated to a drug having cytotoxic activity. An ADC can efficiently deliver the drug to cancer cells, and can thereby be expected to kill the cancer cells by accumulating the drug in the cancer cells (Non Patent Literature 3 and Patent Literature 1 and 2). As for ADCs, for example, Mylotarg (registered trademark) (gemtuzumab ozogamicin) comprising a monoclonal antibody conjugated to a calicheamicin derivative and targeting CD33 has been approved as a therapeutic drug for acute myeloid leukemia, and Besponsa (registered trademark) (inotuzumab ozogamicin) targeting CD22 has been approved as a therapeutic drug for relapsed or refractory precursor B-cell acute lymphocytic leukemia. Adcetris (registered trademark) (brentuximab vedotin) comprising a monoclonal antibody conjugated to monomethyl auristatin E and targeting CD30 has been approved as a therapeutic drug for Hodgkin's lymphoma and anaplastic large cell lymphoma; Polivy (registered trademark) (polatuzumab vedotin) targeting CD79b has been approved as a therapeutic drug for diffuse large B-cell lymphoma; PADCEV (registered trademark) (enfortumab vedotin) targeting nectin-4 has been approved as a therapeutic drug for locally advanced or metastatic urothelial cancer; and BLENREP (registered trademark) (belantamab mafodotin) comprising an anti-B cell maturation antigen monoclonal antibody conjugated to monomethyl auristatin F has been approved as a therapeutic drug for relapsed or refractory multiple myeloma. KADCYLA (registered trademark) (trastuzumab emtansine) comprising an anti-HER2 monoclonal antibody conjugated to emtansine is used in the treatment of HER2-positive advanced or recurrent breast cancer, and Trodelvy (registered trademark) (sacituzumab govitecan) comprising an anti-TROP2 monoclonal antibody conjugated to SN-38, an active metabolite of irinotecan, is used in the treatment of advanced triple negative breast cancer.

The features of a target antigen suitable for an ADC as an antitumor drug can be that: the antigen is specifically highly expressed on the surface of cancer cells but has low expression or is not expressed in normal cells; the antigen can be internalized into cells; the antigen is not secreted from the cell surface; etc. Important features of the antibody suitable for an ADC are that the antibody specifically binds to the target antigen as well as has high internalization ability. The internalization ability of the antibody depends on the properties of both the target antigen and the antibody. It is difficult to predict an antigen-binding site suitable for internalization from the molecular structure of a target or to predict an antibody having high internalization ability from binding strength, physical properties, and the like of the antibody. Hence, an important challenge in developing an ADC having high efficacy is obtaining an antibody having high internalization ability against the target antigen (Non Patent Literature 4).

CD37 is a four-pass transmembrane protein of the tetraspanin superfamily (Non Patent Literature 5). According to previous studies, for example, the control of cell survival via the activation of the PI3K/Akt pathway or reduced production of IgG1 in the analysis of CD37-deficient mice has been reported, though strict physiological functions are unknown (Non Patent Literatures 6 and 7). CD37 is widely expressed at stages of differentiation from precursor B cells to mature B cells, but is not expressed in plasma cells.

Although its expression is also found in T cells, NK cells, and monocytes, the expression level is low and CD37 is not expressed in blood cells such as erythrocytes or platelets. CD37 is highly expressed in tumor cells of B-cell non-Hodgkin's lymphoma (NHL) and chronic lymphocytic leukemia (CLL). Such an expression profile suggests that CD37 serves as a promising therapeutic target for malignant B-cell lymphoma, and some antibody drugs targeting CD37 have progressed to clinical trials so far (Non Patent Literature 8). Among others, CD37 has high internalization activity and is therefore considered also promising as a target of an ADC. IMGN529 comprising an anti-CD37 antibody conjugated to DM1 is currently under clinical trial (Non Patent Literature 9 and Patent Literature 3). However, IMGN529 has exhibited efficacy only for specific patients with an overall response rate of 12.8% in a phase I trial targeting relapsed or refractory B-cell non-Hodgkin's lymphoma (NHL) patients (Non Patent Literature 10). Betalutin (lutetium-177-labeled anti-CD37 antibody), GEN3009 (anti-CD37 biparatopic antibody), and CAR37 T cells (CD37-targeting CAR T cells) are currently under clinical trials as drugs targeting CD37 (Non Patent Literatures 11, 12, and 13).

ENHERTU (registered trademark) (trastuzumab deruxtecan) comprising an anti-HER2 monoclonal antibody conjugated to deruxtecan, a camptothecin derivative, is used in the treatment of HER2-positive advanced or recurrent breast cancer (Non Patent Literature 14). HER3-DXd (Non Patent Literature 15), Trop2-DXd (Non Patent Literature 16), and the like are currently under clinical trial as an ADC containing deruxtecan. Nonetheless, neither an ADC comprising an anti-CD37 antibody conjugated to deruxtecan nor an ADC containing deruxtecan and targeting B-cell non-Hodgkin's lymphoma as a disease has yet been reported.

CITATION LIST

Patent Literature

Patent Literature 1: International Publication No. WO2014/057687
Patent Literature 2: U.S. patent application publication No. 2016/0297890 specification
Patent Literature 3: International Publication No. WO2011/112978
Non Patent Literature 1: Gilles S., et al., Adv Ther, 2232-2273, 34, 2017
Non Patent Literature 2: Andrew R., et al., Best Pract Res Clin Haematol, 203-216, 24, 2011
Non Patent Literature 3: Polakis P., Pharmacological Reviews, 3-19, 68, 2016
Non Patent Literature 4: Peters C., et al., Bioscience Reports, 1-20, 35, 2015
Non Patent Literature 5: Charrin S., et al., J Cell Sci. 3641-3648, 127, 2014
Non Patent Literature 6: Magdalena., et al., Expert Opin Investig Drug. 171-177, 27, 2018
Non Patent Literature 7: Knobeloch K P, et al., Moll Cell Biol, 5363-5369, 20, 2000
Non Patent Literature 8: Zahra P et al., Biotechnology letters, 1459-1466, 40, 2018
Non Patent Literature 9: Jutta D et al., Blood, 3500-3510, 122, 2013
Non Patent Literature 10: Anastasios S et al., Invest New Drugs, 869-876, 36, 2018
Non Patent Literature 11: Alexandre P et al., Leukemia, 1315-1328, 34, 2020
Non Patent Literature 12: Simone C et al., Blood Cancer Journal, 10, 30, 2020
Non Patent Literature 13: Irene S et al., Blood, 1495-1506, 132, 2018
Non Patent Literature 14: Susan J et al., Drugs, 501-508, 80, 2020
Non Patent Literature 15: Kimio Y et al., Oncogene, 1398-1409, 38, 2019
Non Patent Literature 16: https://mct.aacrjournals.org/content/early/2021/08/19/1535-7163.MCT-21-0206.abstract

SUMMARY OF INVENTION

Technical Problem

It is an object of the present invention to provide an antibody specifically binding to CD37-positive tumor cells such as malignant B-cell lymphoma, an antibody-drug conjugate comprising the antibody, a pharmaceutical composition having therapeutic effects on a tumor using the antibody-drug conjugate, a method for treating a tumor using the aforementioned pharmaceutical composition, a method for producing the antibody, and a method for producing the antibody-drug conjugate, and the like.

Solution to Problem

The present inventors have conducted intensive studies directed towards achieving the above-described object, and completed the present invention by finding that an anti-CD37 antibody-drug conjugate comprising an anti-CD37 antibody conjugated to a drug exerting toxicity in cells via a linker having a specific structure exhibits an antitumor effect on a CD37-positive malignant tumor such as malignant B-cell lymphoma. Specifically, the present invention includes the following aspects of the invention.

[1] An antibody-drug conjugate wherein an anti-CD37 antibody is conjugated to a drug-linker structure represented by any one formula selected from the group consisting of the following formulas (a) to (f):

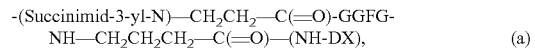
-(Succinimid-3-yl-N)—CH$_2$CH$_2$—C(=O)-GGFG-NH—CH$_2$CH$_2$CH$_2$—C(=O)—(NH-DX),    (a)

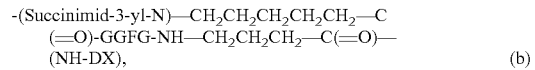
-(Succinimid-3-yl-N)—CH$_2$CH$_2$CH$_2$CH$_2$—C(=O)-GGFG-NH—CH$_2$CH$_2$CH$_2$—C(=O)—(NH-DX),    (b)

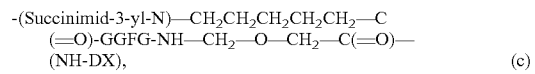
-(Succinimid-3-yl-N)—CH$_2$CH$_2$CH$_2$CH$_2$—C(=O)-GGFG-NH—CH$_2$—O—CH$_2$—C(=O)—(NH-DX),    (c)

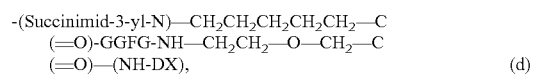
-(Succinimid-3-yl-N)—CH$_2$CH$_2$CH$_2$CH$_2$—C(=O)-GGFG-NH—CH$_2$CH$_2$—O—CH$_2$—C(=O)—(NH-DX),    (d)

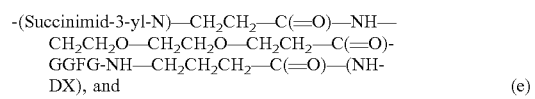
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX), and    (e)

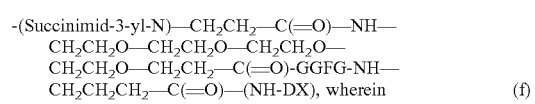
-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX), wherein    (f)

-(Succinimid-3-yl-N)— has a structure represented by the following formula:

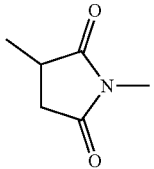

[Formula 1]

which is connected to the antibody at position 3 thereof and is connected to a methylene group in the linker structure containing this structure on the nitrogen atom at position 1, GGFG represents an amino acid sequence consisting of glycine-glycine-phenylalanine-glycine linked through peptide bonds, —(NH-DX) is a group represented by the following formula:

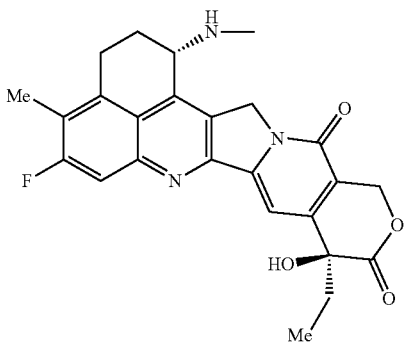

[Formula 2]

with the nitrogen atom of the amino group at position 1 as a connecting position, and the anti-CD37 antibody is an antibody comprising a light chain variable region having the amino acid sequence at positions 21 to 128 in the light chain full-length amino acid sequence shown in SEQ ID NO: 2 or an amino acid sequence having a homology of 90% or more to the amino acid sequence at positions 21 to 128 in the light chain full-length amino acid sequence shown in SEQ ID NO: 2, and a heavy chain variable region having the amino acid sequence at positions 20 to 138 in the heavy chain full-length amino acid sequence shown in SEQ ID NO: 4 or an amino acid sequence having a homology of 90% or more to the amino acid sequence at positions 20 to 138 in the heavy chain full-length amino acid sequence shown in SEQ ID NO: 4.

[2] The antibody-drug conjugate according to [1], wherein the anti-CD37 antibody is an antibody comprising a heavy chain variable region and a light chain variable region in any one combination selected from the group consisting of the following combinations (g) to (j):

(g) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 4;

(h) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6;

(i) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8; and (j) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

[3] The antibody-drug conjugate according to [1] or [2], wherein the anti-CD37 antibody is an antibody comprising a heavy chain variable region and a light chain variable region in any one combination selected from the group consisting of the following combinations (h) to (j):

(h) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6;

(i) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8; and (j) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

[4] The antibody-drug conjugate according to any one of [1] to [3], wherein the anti-CD37 antibody is an antibody comprising a heavy chain and a light chain in any one combination selected from the group consisting of the following combinations (k) to (n):

(k) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 4;

(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;

(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and (n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

[5] The antibody-drug conjugate according to any one of [1] to [4], wherein the anti-CD37 antibody is an antibody comprising a heavy chain and a light chain in any one combination selected from the group consisting of the following combinations (l) to (n):

(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;

(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and (n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

[6] The antibody-drug conjugate according to any one of [1] to [5], wherein the drug-linker structure is represented by any one formula selected from the group consisting of the following formulas (c), (d), and (e):

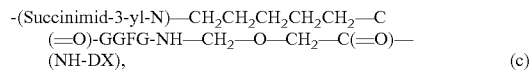

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),   (c)

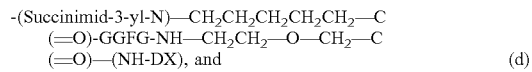

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX), and   (d)

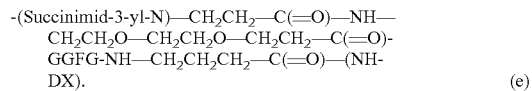

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).   (e)

[7] The antibody-drug conjugate according to any one of [1] to [6], wherein the drug-linker structure is represented by the following formula (c) or (e):

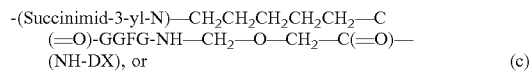

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX), or   (c)

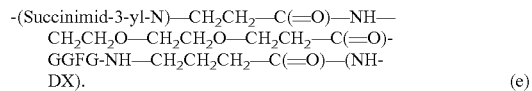

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).   (e)

[8] The antibody-drug conjugate according to any one of [1] to [7], which is represented by the following formula (wherein A represents a connecting position to the antibody):

[Formula 3]

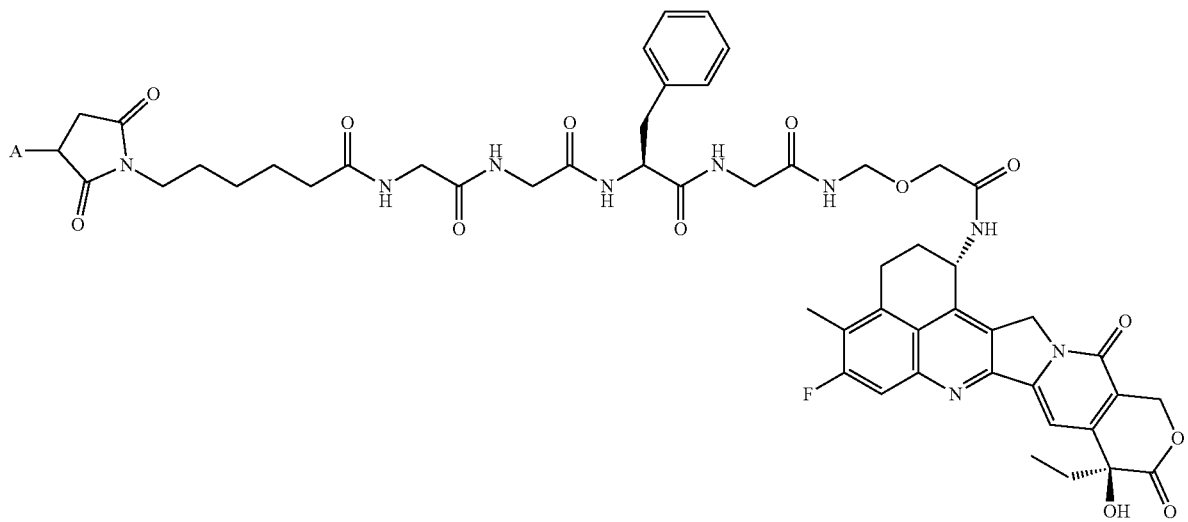

wherein the antibody is conjugated to a drug linker by a thioether bond.

[9] The antibody-drug conjugate according to any one of [1] to [8], which is represented by the following formula:

[Formula 4]

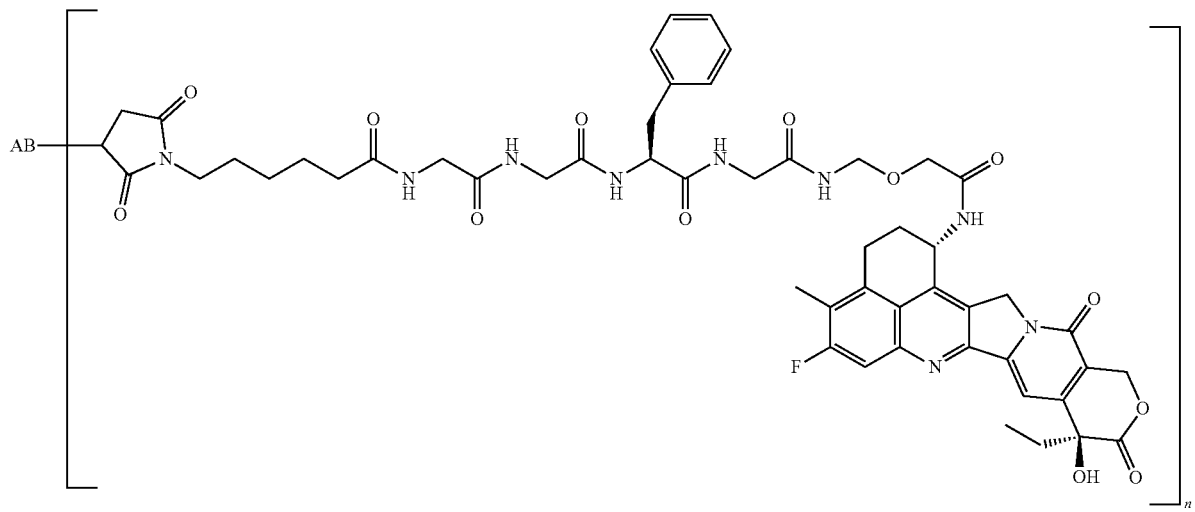

wherein AB represents the antibody, n represents the average number of units of the drug-linker structure conjugated to the antibody per antibody, and the antibody is connected to the linker via a sulfhydryl group derived from the antibody.

[10] The antibody-drug conjugate according to any one of [1] to [9], wherein the antibody heavy chain has undergone one or two or more modifications selected from the group consisting of N-linked glycosylation, O-linked glycosylation, amino-terminal processing, carboxyl-terminal processing, deamidation, isomerization of aspartic acid, oxidation of methionine, oxidation of tryptophan, addition of a methionine residue to the amino terminus, amidation of a proline residue, and a deletion of one or two amino acids from the carboxyl terminus.

[11] The antibody-drug conjugate according to [10], wherein one or two amino acids are deleted from the carboxyl terminus of the antibody heavy chain.

[12] The antibody-drug conjugate according to [10] or [11], wherein one amino acid is deleted from each of the carboxyl termini of both of the antibody heavy chains.

[13] The antibody-drug conjugate according to any one of [10] to [12], wherein a proline residue at the carboxyl terminus of the antibody heavy chain is further amidated.

[14] The antibody-drug conjugate according to any one of [1] to [13], wherein the average number of units of the drug-linker structure conjugated per antibody is in the range of from 1 to 10.

[15] The antibody-drug conjugate according to any one of [1] to [14], wherein the average number of units of the drug-linker structure conjugated per antibody is in the range of from 2 to 8.

[16] The antibody-drug conjugate according to any one of [1] to [15], wherein the average number of units of the drug-linker structure conjugated per antibody is in the range of from 3 to 8.

[17] The antibody-drug conjugate according to any one of [1] to [16], wherein the average number of units of the drug-linker structure conjugated per antibody is in the range of from 7 to 8.

[18] The antibody-drug conjugate according to any one of [1] to [17], wherein the average number of units of the drug-linker structure conjugated per antibody is 8.

[19] A pharmaceutical composition comprising the antibody-drug conjugate according to any one of [1] to [18], a

[20] pharmacologically acceptable salt thereof, or a hydrate of the conjugate or the salt.

[21] The pharmaceutical composition according to [19], which is an antitumor drug.

[22] The pharmaceutical composition according to [20], wherein the tumor is a tumor expressing CD37.

[22] The pharmaceutical composition according to [20] or [21], wherein the tumor is any one tumor selected from the group consisting of diffuse large B-cell lymphoma, follicular lymphoma, mantle cell lymphoma, marginal zone lymphoma, Burkitt's lymphoma and chronic lymphocytic leukemia.

[23] The pharmaceutical composition according to [20] or [21], wherein the tumor is any one tumor selected from the group consisting of T-cell lymphoma such as peripheral T-cell lymphoma or cutaneous T-cell lymphoma, myelodysplastic syndrome and acute myeloid leukemia.

[24] A method for treating a tumor, which comprises the step of administering the antibody-drug conjugate according to any one of [1] to [18], a pharmacologically acceptable salt thereof, or a hydrate of the conjugate or the salt to an individual.

[25] The treatment method according to [24], wherein the tumor is a tumor expressing CD37.

[26] The treatment method according to [24] or [25], wherein the tumor is any one tumor selected from the group consisting of diffuse large B-cell lymphoma, follicular lymphoma, mantle cell lymphoma, marginal zone lymphoma, Burkitt's lymphoma and chronic lymphocytic leukemia.

[27] The treatment method according to [24] or [25], wherein the tumor is any one tumor selected from the group consisting of T-cell lymphoma such as peripheral T-cell lymphoma or cutaneous T-cell lymphoma, myelodysplastic syndrome and acute myeloid leukemia.

[28] A therapeutic agent for a tumor comprising the antibody-drug conjugate according to any one of [1] to [18], a pharmacologically acceptable salt thereof, or a hydrate of the conjugate or the salt.

[29] Use of the antibody-drug conjugate according to any one of [1] to [18], a pharmacologically acceptable salt thereof, or a hydrate of the conjugate or the salt for the treatment of a tumor.

[30] Use of the antibody-drug conjugate according to any one of [1] to [18], a pharmacologically acceptable salt thereof, or a hydrate of the conjugate or the salt for the preparation of a medicament for the treatment of a tumor.

[31] A physiological saline solution formulation comprising 0.001 to 100 mg/kg of the antibody-drug conjugate according to any one of [1] to [18], a pharmacologically acceptable salt thereof, or a hydrate of the conjugate or the salt.

Further, the present invention also includes the following aspects of the invention.

(i) An antibody or a functional fragment of the antibody specifically binding to CD37 and comprising a heavy chain variable region and a light chain variable region in any one combination selected from the group consisting of the following combinations (a) to (d):
(a) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 4;
(b) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6;
(c) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8; and
(d) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

(ii) The antibody or the functional fragment of the antibody according to (i), specifically binding to CD37 and comprising a heavy chain and a light chain in any one combination selected from the group consisting of the following combinations (e) to (h):
(e) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 4;
(f) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;
(g) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and
(h) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

(iii) A polynucleotide encoding the antibody or the functional fragment of the antibody according to (i) or (ii).

(iv) An expression vector comprising the polynucleotide according to (iii).

(v) Host cells transformed with the expression vector according to (iv).

(vi) The host cells according to (v), wherein the host cells are eukaryotic cells.

(vii) A method for producing an antibody or a functional fragment of the antibody, which comprises the step of culturing the host cells according to (v) or (vi), and the step of collecting an antibody of interest from the culture obtained by the aforementioned step.

(viii) An antibody or a functional fragment of the antibody obtained by the method for production according to (vii).

(ix) The antibody or the functional fragment of the antibody according to (viii), which comprises one or two or more modifications selected from the group consisting of N-linked glycosylation, O-linked glycosylation, amino-terminal processing, carboxyl-terminal processing, deamidation, isomerization of aspartic acid, oxidation of methionine, oxidation of tryptophan, addition of a methionine residue to the amino terminus, amidation of a proline residue, and a deletion of one or two amino acids from the carboxyl terminus.

(x) The antibody or the functional fragment of the antibody according to (ix), wherein one or two amino acids are deleted from the carboxyl terminus of the heavy chain thereof.

(xi) The antibody or the functional fragment of the antibody according to (ix) or (x), wherein one amino acid is deleted from each of the carboxyl termini of both of the heavy chains thereof.

(xii) The antibody or the functional fragment of the antibody according to any one of (ix) to (xi), wherein a proline residue at the carboxyl terminus of the heavy chain is further amidated.

(xiii) An antibody-drug conjugate, wherein a drug is conjugated to the antibody or the functional fragment of the antibody according to any one of (viii) to (xii).

(xiv) A method for producing an antibody-drug conjugate, which comprises the step of culturing the host cells according to (v) or (vi), the step of collecting an antibody of interest or a functional fragment of the antibody from the culture obtained by the aforementioned step, and the step of reacting the antibody or the functional fragment of the antibody obtained by the aforementioned step with a drug-linker intermediate compound.

Advantageous Effects of Invention

A feature of the anti-CD37 antibody of the present invention is to specifically bind to CD37-positive tumor cells such as malignant B-cell lymphoma. An anti-CD37 antibody-drug conjugate comprising the antibody conjugated to a drug exerting toxicity in cells via a linker having a specific structure can be expected to achieve excellent antitumor effects and safety by administration to patients having cancer cells expressing CD37. Specifically, the anti-CD37 antibody-drug conjugate of the present invention is useful as an antitumor agent for malignant B-cell lymphoma and the like. Also, the anti-CD37 antibody-drug conjugate of the present invention has a favorable recovery rate in physiological saline and is capable of being handled in physiological saline.

BRIEF DESCRIPTION OF DRAWINGS

FIG. 1 is a diagram showing a nucleotide sequence encoding a hmAb-L11 light chain and the amino acid sequence of the hmAb-L11 light chain.

FIG. 2 is a diagram showing a nucleotide sequence encoding a hmAb-H11 heavy chain and the amino acid sequence of the hmAb-H11 heavy chain.

FIG. 3 is a diagram showing a nucleotide sequence encoding a hmAb-H541 heavy chain and the amino acid sequence of the hmAb-H541 heavy chain.

FIG. 4 is a diagram showing a nucleotide sequence encoding a hmAb-H551 heavy chain and the amino acid sequence of the hmAb-H551 heavy chain.

FIG. 5 is a diagram showing a nucleotide sequence encoding a hmAb-H11a heavy chain and the amino acid sequence of the hmAb-H11a heavy chain.

FIG. 6 is a diagram showing results of evaluating the binding activity of a humanized anti-CD37 antibody-drug conjugate against CD37-positive human diffuse large B-cell lymphoma cell line OCI-LY7.

FIG. 7 is a diagram showing results of evaluating the in vitro cell growth inhibition activity of a humanized anti-CD37 antibody-drug conjugate against CD37-positive human diffuse large B-cell lymphoma cell line OCI-LY7.

FIG. 8 is a diagram showing the in vivo antitumor effect of a humanized anti-CD37 antibody-drug conjugate against SCID mice into which CD37-positive human diffuse large B-cell lymphoma cell line OCI-LY7 was inoculated.

FIG. 9 is a diagram showing the in vivo antitumor effect of a humanized anti-CD37 antibody-drug conjugate against SCID mice into which CD37-positive human diffuse large B-cell lymphoma cell line WSU-DLCL2 was inoculated.

FIG. 10 is a diagram showing the in vivo antitumor effect of a humanized anti-CD37 antibody-drug conjugate against SCID mice into which CD37-positive human diffuse large B-cell lymphoma cell line SU-DHL-8 was inoculated.

FIG. 11 is a diagram showing the in vivo antitumor effects of a humanized anti-CD37 antibody-drug conjugate, POLIVY (registered trademark), and IMGN529 against SCID mice into which CD37-positive human diffuse large B-cell lymphoma cell line OCI-LY7 was inoculated.

FIG. 12 is a diagram showing the in vivo antitumor effects of a humanized anti-CD37 antibody-drug conjugate, POLIVY, and IMGN529 against SCID mice into which CD37-positive human diffuse large B-cell lymphoma cell line SU-DHL-8 was inoculated.

FIG. 13 is a diagram showing the in vivo antitumor effects of a humanized anti-CD37 antibody-drug conjugate, POLIVY, and IMGN529 against SCID mice into which CD37-positive human diffuse large B-cell lymphoma cell line NU-DUL-1 was inoculated.

FIG. 14 is a diagram showing the in vivo antitumor effect of a humanized anti-CD37 antibody-drug conjugate against SCID mice into which CD37-positive human diffuse large B-cell lymphoma cell line SU-DHL-4 was inoculated.

FIG. 15 is a diagram showing the in vivo antitumor effects of a humanized anti-CD37 antibody-drug conjugate, RITUXAN (registered trademark), ibrutinib, venetoclax, and TREAKISYM (registered trademark) against SCID mice into which CD37-positive human chronic lymphocytic leukemia cell line JVM-3 was inoculated.

FIG. 16 is a diagram showing the in vivo antitumor effects of a humanized anti-CD37 antibody-drug conjugate, POLIVY, and IMGN529 against SCID mice into which CD37-positive human follicular lymphoma cell line DOHH-2 was inoculated.

DESCRIPTION OF EMBODIMENTS

Definition

In the present invention, the term "gene" means a nucleic acid molecule comprising a nucleotide sequence encoding the amino acids of a protein, or its complementary strand. The term "gene" is meant to include, for example, a polynucleotide, an oligonucleotide, DNA, mRNA, CDNA, and CRNA comprising a nucleotide sequence encoding the amino acids of a protein or a nucleotide sequence complementary thereto. Such a gene is a single-stranded, double-stranded, or triple or more stranded nucleotide. The term "gene" is also meant to include an association of DNA and RNA strands, a mixture of ribonucleotides (RNAs) and deoxyribonucleotides (DNAs) on one nucleotide strand, and a double-stranded or triple or more stranded nucleotide comprising such a nucleotide strand. Examples of the "CD37 gene" of the present invention can include DNA, mRNA, CDNA, and CRNA comprising a nucleotide sequence encoding the amino acid sequence of the CD37 protein.

In the present invention, the term "nucleotide" has the same meaning as "nucleic acid" and "nucleic acid molecule", and is also meant to include, for example, DNA, RNA, a probe, an oligonucleotide, a polynucleotide, and a primer. Such a nucleotide is a single-stranded, double-stranded, or triple or more stranded nucleotide. The term "nucleotide" is also meant to include an association of DNA and RNA strands, a mixture of ribonucleotides (RNAs) and deoxyribonucleotides (DNAs) on one nucleotide strand, and an association of two strands or three or more strands comprising such a nucleotide strand.

In the present invention, the terms "polypeptide", "peptide", and "protein" have the same meaning.

In the present invention, the term "protein" refers to a "protein" from any given vertebrate source including mammals such as primates (e.g., humans and monkeys) and rodents (e.g., mice and rats) unless otherwise specified.

In the present invention, the term "antigen" has the same meaning as "immunogen".

In the present invention, the term "cell" also includes, for example, various cells derived from individual animals, subcultured cells, primary cultured cells, cell lines, recombinant cells, and microbial cells.

In the present invention, the "site" to which an antibody binds, i.e., the "site" recognized by an antibody, means a partial peptide or a partial conformation on an antigen that is bound or recognized by the antibody. In the present invention, such a site is also referred to as an epitope or an antibody binding site. Examples of the site on the CD37 protein that is bound or recognized by the anti-CD37 antibody of the present invention can include a partial peptide or a partial conformation on the CD37 protein.

In the present invention, the term "CDR" means a complementarity determining region, and the term "FR" means a framework region. The heavy and light chains of an antibody molecule are known to each have three CDRs. The CDRs are also called hypervariable domains. These regions are located in the variable regions of the antibody heavy and light chains. These sites have a particularly highly variable primary structure and are usually separated into three positions on the respective primary structures of the heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the three-dimensional structure and determine the specificity for the antigen to be bound. The portions other than CDRH1 to CDRH3 in the heavy chain variable region amino acid sequence are called FRs, and the portions from the amino terminus up to but not including CDRH1, from just after CDRH1 up to but not including CDRH2, from just after CDRH2 up to but not including CDRH3, and from just after CDRH3 to the carboxyl terminus are respectively called FRH1 to FRH4. Likewise, the portions other than CDRL1 to CDRL3 in the light chain variable region amino acid sequence are also FRs, and the portions from the amino terminus up to but not including CDRL1, from just after CDRL1 up to but not including CDRL2, from just after CDRL2 up to but not including CDRL3, and from just after CDRL3 to the carboxyl terminus are respectively called FRL1 to FRL4. That is, in (the amino acid sequence(s) of) the heavy chain and light chain variable regions, FRH1-CDRH1-FRH2-CDRH2-FRH3-CDRH3-FRH4 and FRL1-CDRL1-FRL2-CDRL2-FRL3-CDRL3-FRL4 are continuously aligned from the amino terminal side toward the carboxyl terminus in this order.

In the present invention, the term "functional fragment of an antibody" means an antibody fragment that exerts at least a part of the functions exerted by the original antibody. Examples of the "functional fragment of the antibody" can include, but are not limited to, Fab, F(ab')2, scFv, Fab', and single chain immunoglobulin. Such a functional fragment of the antibody may be obtained by treating a full-length molecule of the antibody protein with an enzyme such as papain or pepsin or may be a recombinant protein produced in an appropriate host cell using a recombinant gene. The "functional fragment of an antibody" having binding activity against the antigen, i.e., human CD37, is referred to as a "binding fragment of an antibody".

1. CD37

CD37 is a four-pass transmembrane protein of the tetraspanin superfamily (Charrin S., et al., J Cell Sci. 3641-3648, 127, 2014). CD37 is a membrane protein composed of 281 amino acids and has both amino-terminal and carboxy-terminal intracellular domains, and its sequence can be referred to under, for example, accession Nos. NM_001774 and NP_001765 (NCBI).

The CD37 protein used in the present invention can be directly purified from the CD37-expressing cells of a human or a non-human mammal (e.g., a rat, a mouse or a monkey) and can then be used, or a cell membrane fraction of the aforementioned cells can be prepared and can be used as the CD37 protein. Alternatively, CD37 can also be obtained by synthesizing it in vitro, or by allowing host cells to produce CD37 by genetic manipulation. According to such genetic manipulation, the CD37 protein can be obtained, specifically, by incorporating CD37 cDNA into a vector capable of expressing the CD37 cDNA, and then synthesizing CD37 in a solution containing enzymes, substrate and energy substances necessary for transcription and translation, or by transforming the host cells of other prokaryotes or eukaryotes, so as to allow them to express CD37. Also, CD37-expressing cells based on the above-described genetic manipulation, or a cell line expressing CD37 may be used as the CD37 protein. Alternatively, the expression vector into which CD37 cDNA has been incorporated can be directly administered to an animal to be immunized, and CD37 can be expressed in the body of the animal thus immunized.

Moreover, a protein which consists of an amino acid sequence comprising a substitution, deletion and/or addition of one or several amino acids in the above-described amino acid sequence of CD37, and has a biological activity equivalent to that of the CD37 protein, is also included within the term "CD37". It is to be noted that the term "several" is used in the present description to mean 1 to 10, 1 to 9, 1 to 8, 1 to 7, 1 to 6, 1 to 5, 1 to 4, 1 to 3, or 1 or 2.

The human CD37 protein has the amino acid sequence shown in SEQ ID NO: 18. The extracellular region of the human CD37 protein is composed of extracellular domain 1 (in the present description, also referred to as EC1) having the amino acid sequence at positions 39 to 59 in the amino acid sequence shown in SEQ ID NO: 18, and extracellular domain 2 (in the present description, also referred to as EC2) having the amino acid sequence at positions 112 to 241 in the amino acid sequence shown in SEQ ID NO: 18.

```
                                          SEQ ID NO: 18
MSAQESCLSL IKYFLFVFNL FFFVLGSLIF CFGIWILIDK

TSFVSFVGLA FVPLQIWSKV LAISGIFTMG IALLGCVGAL

KELRCLLGLY FGMLLLLFAT QITLGILIST QRAQLERSLR

DVVEKTIQKY GTNPEETAAE ESWDYVQFQL RCCGWHYPQD

WFQVLILRGN GSEAHRVPCS CYNLSATNDS TILDKVILPQ

LSRLGHLARS RHSADICAVP AESHIYREGC AQGLQKWLHN

NLISIVGICL GVGLLELGFM TLSIFLCRNL DHVYNRLARY R
```

For the sequence of the human CD37 protein, also see the following description:
https://www.uniprot.org/uniprot/P11049

2. Production of Anti-CD37 Antibody (2-1) Antibody

In the present invention, both the antibody binding to CD37 and the antibody recognizing CD37 are also referred to as an "anti-CD37 antibody" or also abbreviated to a "CD37 antibody".

The anti-CD37 antibody of the present invention may be derived from any species. Preferred examples of the species can include humans, rats, mice and rabbits. When the anti-CD37 antibody of the present invention is derived from a species other than humans, it is desirable to chimerize or humanize the anti-CD37 antibody by a known technique. The antibody of the present invention may be a polyclonal antibody or may be a monoclonal antibody, and a monoclonal antibody is preferred.

The anti-CD37 antibody of the present invention is an antibody that can target tumor cells. Specifically, the anti- CD37 antibody of the present invention possesses the property of being able to recognize tumor cells, the property of being able to bind to tumor cells, and the property of being internalized into tumor cells by cellular uptake, and the like. Accordingly, the anti-CD37 antibody of the present invention can be conjugated to a compound having antitumor activity via a linker to prepare an antibody-drug conjugate.

The binding activity of an antibody against tumor cells can be confirmed by flow cytometry. The uptake of an antibody into tumor cells can be confirmed by (1) an assay of visualizing a cellularly taken-up antibody under a fluorescent microscope using a secondary antibody (fluorescently labeled) binding to the antibody (Cell Death and Differentiation (2008) 15, 751-761), (2) an assay of measuring the amount of cellularly taken-up fluorescence using a secondary antibody (fluorescently labeled) binding to the antibody (Molecular Biology of the Cell Vol. 15, 5268-5282 December 2004) or (3) a Mab-ZAP assay using an immunotoxin binding to the antibody, wherein the toxin is released upon cellular uptake, so as to suppress cell growth (Bio Techniques 28:162-165, January 2000). A recombinant conjugated protein of a catalytic region of diphtheria toxin and protein G may be used as the immunotoxin.

In the present description, the term "high internalization ability" is used to mean that the survival rate (which is indicated by a ratio relative to a cell survival rate without antibody addition defined as 100%) of CD37-expressing cells to which the aforementioned antibody and a saporin-labeled anti-rat IgG antibody have been administered is preferably 70% or less, and more preferably 60% or less.

The antitumor antibody-drug conjugate of the present invention comprises a conjugated compound exerting an antitumor effect. Therefore, it is preferred, but not essential, that the antibody itself should have an antitumor effect. For the purpose of specifically and selectively exerting the cytotoxicity of the antitumor compound in tumor cells, it is important and preferred that the antibody should have a property of being internalized and transferred into tumor cells.

The anti-CD37 antibody can be obtained by immunizing an animal with a polypeptide serving as an antigen by a method performed in this field, and then collecting and purifying an antibody produced in a living body thereof. It is preferred to use CD37 retaining its three-dimensional structure as an antigen because CD37 is a four-pass transmembrane protein. Examples of such a method can include DNA immunization.

The origin of the antigen is not limited to a human, and thus, an animal can also be immunized with an antigen derived from a non-human animal such as a mouse or a rat. In this case, an antibody applicable to the disease of a human can be selected by examining the cross-reactivity of the obtained antibody binding to the heterologous antigen with the human antigen.

Furthermore, antibody-producing cells that produce an antibody against the antigen can be fused with myeloma cells according to a known method (e.g., Kohler and Milstein, Nature (1975) 256, p. 495-497; and Kennet, R. ed., Monoclonal Antibodies, p. 365-367, Plenum Press, N. Y. (1980)) to establish hybridomas, so as to obtain a monoclonal antibody.

Hereinafter, the method for obtaining an antibody against CD37 will be specifically described.

(1) Preparation of Antigen

The antigen can be obtained by allowing host cells to produce a gene encoding the antigen protein according to genetic manipulation. Specifically, a vector capable of expressing the antigen gene is produced, and the vector is then introduced into host cells, so that the gene is expressed therein, and thereafter, the expressed antigen may be purified. The antibody can also be obtained by a method of immunizing an animal with the antigen-expressing cells based on the above-described genetic manipulation, or a cell line expressing the antigen.

Alternatively, the antibody can also be obtained, without the use of the antigen protein, by incorporating cDNA of the antigen protein into an expression vector, then administering the expression vector to an animal to be immunized, and expressing the antigen protein in the body of the animal thus immunized, so that an antibody against the antigen protein is produced therein.

(2) Production of Anti-CD37 Monoclonal Antibody

The anti-CD37 antibody used in the present invention is not particularly limited. For example, an antibody specified by an amino acid sequence shown in the sequence listing of the present application can be suitably used. The anti-CD37 antibody used in the present invention is desirably an antibody having the following properties:

(1) an antibody having the following properties:
(a) specifically binding to CD37, and
(b) having the activity of being internalized into CD37-expressing cells by binding to CD37;
(2) the antibody according to the above (1), wherein the CD37 is human CD37; or
(3) the antibody according to the above (1) or (2) which recognizes the conformation of CD37.

The method for obtaining the antibody against CD37 of the present invention is not particularly limited as long as an anti-CD37 antibody can be obtained. It is preferred to use CD37 retaining its conformation as an antigen because CD37 is a transmembrane protein.

One preferred example of the method for obtaining the antibody can include a DNA immunization method. The DNA immunization method is an approach which involves transfecting an individual animal (e.g., mouse or rat) with an expression plasmid of an antigen, and then expressing the antigen in the animal to induce immunity against the antigen. The transfection approach includes a method of directly injecting the plasmid into a muscle, a method of injecting a transfection reagent such as a liposome or polyethylenimine into a vein, an approach using a viral vector, an approach of injecting gold particles attached to the plasmid using a gene gun, a hydrodynamic method of rapidly injecting a plasmid solution in a large amount into a vein, and the like. With regard to the transfection method of injecting the expression plasmid into a muscle, a technique called in vivo electroporation, which involves applying electroporation to the intramuscular injection site of the plasmid, is known as an approach for improving expression levels (Aihara H, Miyazaki J. Nat Biotechnol. 1998 September; 16 (9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96 (8): 4262-7). This approach further improves the expression level by treating the muscle with hyaluronidase before the intramuscular injection of the plasmid (McMahon J M1, Signori E, Wells K E, Fazio V M, Wells D J., Gene Ther. 2001 August; 8 (16): 1264-70). Furthermore, hybridoma production can be performed by a known method, and can also be performed using, for example, a Hybrimune Hybridoma Production System (Cyto Pulse Sciences, Inc.).

Specific examples of obtaining a monoclonal antibody can also include the following procedures:

(a) immune response can be induced by incorporating CD37 cDNA into an expression vector, and directly administering the vector to an animal to be immunized by a method such as electroporation or a gene gun, so as to express CD37 in the body of the animal. The administration of the vector by electroporation or the like may be performed one or more times, preferably a plurality of times, if necessary for enhancing antibody titer;

(b) collection of tissue (e.g., a lymph node) containing antibody-producing cells from the aforementioned animal in which the immune response has been induced;

(c) preparation of myeloma cells (hereinafter, referred to as "myelomas");

(d) cell fusion between the antibody-producing cells and the myelomas;

(e) selection of a hybridoma group producing an antibody of interest;

(f) division into single cell clones (cloning); and (g) the culture of hybridomas for the mass production of monoclonal antibodies, or the breeding of animals into which the hybridomas are inoculated.

The resulting monoclonal antibody has high antigen specificity for CD37. Examples of the aforementioned monoclonal antibody can include, but are not particularly limited to, anti-CD37 mouse monoclonal antibody HH1 (Smeland E, et al., Scand J Immunol, 21 (3), 205-214 (1985)). (h) study of the physiological activity (internalization activity) and binding specificity of the monoclonal antibody thus produced, or examination of the properties of the antibody as a labeling reagent.

Examples of the method for measuring the antibody titer used herein can include, but are not limited to, flow cytometry and Cell-ELISA.

Furthermore, in the case where the steps (a) to (h) in the specific examples of obtaining a monoclonal antibody described in the above "2. Production of anti-CD37 antibody" are carried out again to obtain independently a monoclonal antibody separately and also in the case where a monoclonal antibody is obtained separately by other methods, an antibody having cytotoxic activity equivalent to that of the anti-CD37 antibody obtained in the step (g) can be obtained. One example of such an antibody can include an antibody binding to the same epitope to which the anti-CD37 antibody obtained in the step (g) binds. If a newly prepared monoclonal antibody binds to a partial peptide or a partial three-dimensional structure to which the anti-CD37 antibody binds, it can be determined that the monoclonal antibody binds to the same epitope to which the anti-CD37 antibody binds. Moreover, by confirming that the monoclonal antibody competes with the anti-CD37 antibody in the binding of the antibody to CD37 (i.e., the monoclonal antibody interferes with the binding of the anti-CD37 antibody to CD37), it can be determined that the monoclonal antibody binds to the same epitope to which the anti-CD37 antibody binds, even if the specific sequence or structure of the epitope has not been determined. When it is confirmed that the monoclonal antibody binds to the same epitope to which the anti-CD37 antibody binds, then it is strongly expected that the monoclonal antibody should have antigen-binding ability or biological activity equivalent to that of the anti-CD37 antibody.

(3) Other Antibodies

The antibody of the present invention also includes genetically recombinant antibodies that have been artificially modified for the purpose of, for example, reducing heterogenetic antigenicity to humans or improving the physical properties of the antibody-drug conjugate, such as a chimeric antibody, a humanized antibody and a human antibody, as well as the above-described monoclonal antibody against CD37. These antibodies can be produced by known methods.

Examples of the chimeric antibody can include antibodies in which a variable region and a constant region are heterologous to each other, such as a chimeric antibody formed by conjugating the variable region of a mouse- or rat-derived antibody to a human-derived constant region (see Proc. Natl. Acad. Sci. U.S.A., 81, 6851-6855, (1984)).

Examples of the humanized antibody can include an antibody formed by incorporating only CDRs into a human-derived antibody (see Nature (1986) 321, p. 522-525), an antibody formed by incorporating the amino acid residues from some frameworks, as well as CDR sequences, into a human antibody according to a CDR grafting method (International Publication No. WO90/07861), and an antibody formed by modifying the amino acid sequences of some CDRs while maintaining antigen-binding ability.

Concrete examples of the humanized antibody of the anti-CD37 mouse monoclonal antibody HH1 include an antibody comprising the light chain variable region of hmAb-L11 and the heavy chain variable region of hmAb-H11, hmAb-H541, hmAb-H551, or hmAb-H11a. The amino acid sequence of hmAb-L11 is shown in SEQ ID NO: 2, and the amino acid sequences of hmAb-H11, hmAb-H541, hmAb-H551, and hmAb-H11a are shown in SEQ ID NOs: 4, 6, 8, and 10, respectively. In hmAb, the light chain variable region consists of the sequence represented by amino acid positions 21 to 128 in the amino acid sequence shown in SEQ ID NO: 2, and the heavy chain variable region consists of the sequence represented by amino acid positions 20 to 138 in the amino acid sequence shown in the corresponding SEQ ID NO. The antibody of the present invention further includes an antibody comprising the full-length light chain of hmAb-L11 and the full-length heavy chain of hmAb-H11, hmAb-H541, hmAb-H551, or hmAb-H11a. The light chain full-length amino acid sequence of hmAb-L11 comprises the sequence represented by amino acid positions 21 to 234 in the amino acid sequence shown in SEQ ID NO: 2, and the heavy chain full-length amino acid sequences of hmAb-H11, hmAb-H541, hmAb-H551, and hmAb-H11a comprise the sequence represented by amino acid positions 20 to 468 in the amino acid sequences shown in SEQ ID NOs: 4, 6, 8, and 10, respectively. Specific examples thereof can include hmAb-H11L11, hmAb-H541L11, hmAb-H551L11, and hmAb-H11aL11.

In SEQ ID NO: 2, the sequence consisting of the amino acid residues at positions 44 to 54 (KASQDVSTAVD: SEQ ID NO: 19) corresponds to CDRL1, the sequence consisting of the amino acid residues at positions 70 to 76 (WASTRHT: SEQ ID NO: 20) corresponds to CDRL2, and the sequence consisting of the amino acid residues at positions 109 to 117 (RQHYSTPFT: SEQ ID NO: 21) corresponds to CDRL3. In SEQ ID NOs: 4, 6, 8, and 10, the sequence consisting of the amino acid residues at positions 45 to 54 (GYSFTDYNMY: SEQ ID NO: 22) corresponds to CDRH1, the sequence consisting of the amino acid residues at positions 69 to 78 (YIDPYNGDTT: SEQ ID NO: 23) corresponds to CDRH2, and the sequence consisting of the amino acid residues at positions 118 to 127 (SPYGHYAMDY: SEQ ID NO: 24) corresponds to CDRH3. These CDR sequences are described in accordance with the AbM definition (Handbook of Therapeutic Antibodies, Chapter 5, Bioinformatics Tools for Antibody Engineering, Andrew C. R. Martin, James Allen, 2007).

The amino acid substitution in the present description is preferably a conservative amino acid substitution. The conservative amino acid substitution is a substitution occurring within an amino acid group associated with certain amino acid side chains. Preferred amino acid groups are the following: acidic group=aspartic acid and glutamic acid; basic group=lysine, arginine, and histidine; non-polar group=alanine, valine, leucine, isoleucine, proline, phenylalanine, methionine, and tryptophan; and uncharged polar family=glycine, asparagine, glutamine, cysteine, serine, threonine, and tyrosine. Other preferred amino acid groups are the following: aliphatic hydroxy group=serine and threonine; amide-containing group=asparagine and glutamine; aliphatic group=alanine, valine, leucine and isoleucine; and aromatic group=phenylalanine, tryptophan and tyrosine. Such amino acid substitution is preferably carried out without impairing the properties of a substance having the original amino acid sequence.

By combining together sequences showing a high homology to the above-described heavy chain amino acid sequences and light chain amino acid sequences, it is possible to select an antibody having a biological activity equivalent to that of each of the above-described antibodies. Such a homology is a homology of generally 80% or more, preferably 85% or more, more preferably 90% or more, further preferably 95% or more, and most preferably 99% or more. Moreover, also by combining amino acid sequences of a heavy chain and a light chain comprising a substitution, deletion or addition of one or several amino acid residues thereof with respect to the amino acid sequence of a heavy chain or a light chain, it is possible to select an antibody having a biological activity equivalent to that of each of the above-described antibodies.

The homology between two types of amino acid sequences can be determined using default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). The Blast algorithm can also be used by accessing www.ncbi.nlm.nih.gov/blast through the internet.

In the light chain amino acid sequence shown in SEQ ID NO: 2 in the sequence listing, the amino acid sequence consisting of the amino acid residues at positions 1 to 20 corresponds to a signal sequence, the amino acid sequence consisting of the amino acid residues at positions 21 to 128 corresponds to a variable region, and the amino acid sequence consisting of the amino acid residues at positions 129 to 234 corresponds to a constant region. The sequence of SEQ ID NO: 2 is described in FIG. 1.

In the heavy chain amino acid sequence shown in SEQ ID NO: 4, 6, 8, or 10, the amino acid sequence consisting of the amino acid residues at positions 1 to 19 corresponds to a signal sequence, the amino acid sequence consisting of the amino acid residues at positions 20 to 138 corresponds to a variable region, and the amino acid sequence consisting of the amino acid residues at positions 139 to 468 corresponds to a constant region. The sequence of SEQ ID NO: 3, 5, 7, or 9 is described in FIG. 2, 3, 4, or 5.

Further examples of the antibody of the present invention can include a human antibody binding to CD37. The anti-CD37 human antibody means a human antibody having only the gene sequence of an antibody derived from human chromosomes. The anti-CD37 human antibody can be obtained by a method using a human antibody-producing mouse having a human chromosomal fragment comprising the heavy chain and light chain genes of a human antibody (see Tomizuka, K. et al., Nature Genetics (1997) 16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, p. 722-727; etc.).

Such a human antibody-producing mouse can be specifically produced by using a genetically modified animal, the gene loci of endogenous immunoglobulin heavy chain and light chain of which have been disrupted and instead the gene loci of the human immunoglobulin heavy chain and light chain have been then introduced using a yeast artificial chromosome (YAC) vector or the like, then producing a knock-out animal and a transgenic animal from such a genetically modified animal, and then breeding such animals with one another.

Otherwise, the anti-CD37 human antibody can also be obtained by transforming eukaryotic cells with cDNA encoding each of the heavy chain and light chain of such a human antibody, or preferably with a vector comprising such cDNA, according to genetic recombination techniques, and then culturing the transformed cells and producing a genetically modified human monoclonal antibody, so that the antibody can be obtained from the culture supernatant.

In this context, eukaryotic cells, and preferably, mammalian cells such as CHO cells, lymphocytes or myelomas can, for example, be used as a host.

Furthermore, a method of obtaining a phage display-derived human antibody that has been selected from a human antibody library (see Wormstone, I. M. et al., Investigative Ophthalmology & Visual Science. (2002) 43 (7), p. 2301-2308; Carmen, S. et al., Briefings in Functional Genomics and Proteomics (2002), 1 (2), p. 189-203; Siriwardena, D. et al., Ophthalmology (2002) 109 (3), p. 427-431; etc.) is also known.

For example, a phage display method, which comprises allowing the variable regions of a human antibody to express as a single chain antibody (scFv) on the surface of phages, and then selecting a phage binding to an antigen, can be applied (Nature Biotechnology (2005), 23, (9), p. 1105-1116).

By analyzing the phage gene that has been selected because of its binding ability to the antigen, DNA sequences encoding the variable regions of a human antibody binding to the antigen can be determined.

Once the DNA sequence of scFv binding to the antigen is determined, an expression vector having the aforementioned sequence is produced, and the produced expression vector is then introduced into an appropriate host and can be allowed to express therein, thereby obtaining a human antibody (International Publication Nos. WO92/01047, WO92/20791, WO93/06213, WO93/11236, WO93/19172, WO95/01438, and WO95/15388, Annu. Rev. Immunol (1994) 12, p. 433-455, Nature Biotechnology (2005) 23 (9), p. 1105-1116).

If a newly produced human antibody binds to a partial peptide or a partial three-dimensional structure to which the CD37 antibody described in the present description binds, it can be determined that the human antibody binds to the same epitope. Moreover, by confirming that the human antibody competes with the CD37 antibody described in the present description in the binding of the antibody to CD37 (i.e., the human antibody interferes with the binding of the CD37 antibody described in the present description to CD37), it can be determined that the human antibody binds to the same epitope to which the CD37 antibody described in the present description binds, even if the specific sequence or structure of the epitope has not been determined. When it is confirmed that the human antibody binds to the same epitope to which the CD37 antibody described in the present description binds, then it is strongly expected that the human antibody should have antigen-binding ability or biological activity equivalent to that of the CD37 antibody described in the present description.

The chimeric antibodies, the humanized antibodies, or the human antibodies obtained by the above-described methods are evaluated for their binding activity against the antigen according to a known method, etc., so that a preferred antibody can be selected.

One example of another indicator for comparison of the properties of antibodies can include the stability of an antibody. A differential scanning calorimeter (DSC) is an apparatus capable of promptly and exactly measuring a thermal denaturation midpoint (Tm) serving as a good indicator for the relative structural stability of a protein. By using DSC to measure Tm values and making a comparison regarding the obtained values, differences in thermal stability can be compared. It is known that the preservation stability of an antibody has a certain correlation with the thermal stability of the antibody (Lori Burton, et al., Pharmaceutical Development and Technology (2007) 12, p. 265-273), and thus, a preferred antibody can be selected using thermal stability as an indicator. Other examples of an indicator for selection of an antibody can include high yield in suitable host cells and low agglutination in an aqueous solution. For example, since an antibody with the highest yield does not always exhibit the highest thermal stability, it is necessary to select an antibody most suitable for administration to a human by comprehensively determining it based on the aforementioned indicators.

The antibody of the present invention also includes a modification of an antibody. A modification is used to mean an antibody of the present invention, which is chemically or biologically modified. Examples of such a chemical modification include the binding of a chemical moiety to an amino acid skeleton, and the chemical modification of an N-linked or O-linked carbohydrate chain. Examples of such a biological modification include antibodies which have undergone a post-translational modification (e.g., N-linked or O-linked glycosylation, amino-terminal or carboxyl-terminal processing, deamidation, isomerization of aspartic acid, oxidation of methionine, and oxidation of tryptophan), and antibodies, to the amino terminus of which a methionine residue is added as a result of having been allowed to be expressed using prokaryote host cells. In addition, such a modification is also meant to include labeled antibodies for enabling detection or isolation of the antibody of the present invention or an antigen, for example, an enzymatically labeled antibody, a fluorescently labeled antibody, and an affinity-labeled antibody. Such a modification of the antibody of the present invention is useful for the improvement of the stability and retention in blood of an antibody; a reduction in antigenicity; detection or isolation of an antibody or an antigen; etc.

Moreover, by regulating a sugar chain modification (glycosylation, de-fucosylation, etc.) that binds to the antibody of the present invention, antibody-dependent cellular cytotoxic activity can be enhanced. As techniques of regulating the sugar chain modification of an antibody, those described in International Publication Nos. WO1999/54342, WO2000/61739, WO2002/31140, WO2007/133855, and WO2013/120066, etc. are known, though the techniques are not limited thereto. The antibody of the present invention also includes antibodies in respect of which the aforementioned sugar chain modification has been regulated.

(2-2) Method for Producing Antibody

Once an antibody gene is isolated, the gene can be introduced into an appropriate host to produce an antibody, using an appropriate combination of a host and an expression vector. A specific example of the antibody gene can be a combination of a gene encoding the heavy chain sequence of the antibody described in the present description and a gene encoding the light chain sequence of the antibody described therein. Upon transformation of host cells, such a heavy chain sequence gene and a light chain sequence gene may be inserted into a single expression vector, or these genes may instead each be inserted into different expression vectors.

When eukaryotic cells are used as hosts, animal cells, plant cells or eukaryotic microorganisms can be used. In particular, examples of the animal cells can include mammalian cells such as COS cells which are monkey cells (Gluzman, Y., Cell (1981) 23, p. 175-182, ATCC CRL-1650), mouse fibroblasts NIH3T3 (ATCC No. CRL-1658), a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220), and FreeStyle 293F cells (Invitrogen Corp.).

When prokaryotic cells are used as hosts, *Escherichia coli* or *Bacillus subtilis* can be used, for example.

An antibody gene of interest is introduced into these cells for transformation, and the transformed cells are then cultured in vitro to obtain an antibody. In the aforementioned culture, there are cases where yield is different depending on the sequence of the antibody, and thus, it is possible to select an antibody, which is easily produced as a medicament, from antibodies having equivalent binding activity, using the yield as an indicator. Accordingly, the antibody of the present invention also includes an antibody obtained by the above-described method for producing an antibody, which comprises a step of culturing the transformed host cells and a step of collecting an antibody of interest or a functional fragment of the antibody from the culture obtained in the aforementioned step.

It is known that the lysine residue at the carboxyl terminus of the heavy chain of an antibody produced by cultured mammalian cells is deleted (Journal of Chromatography A, 705:129-134 (1995)), and also, it is known that the two amino acid residues at the heavy chain carboxyl terminus, glycine and lysine, are deleted, and that the proline residue newly positioned at the carboxyl terminus is amidated (Analytical Biochemistry, 360:75-83 (2007)). However, such deletion and modification of these heavy chain sequences does not have an influence on the antigen-binding activity and effector function (activation of complement, antibody-dependent cellular cytotoxicity, etc.) of an antibody. Accordingly, the antibody according to the present invention also includes an antibody that has undergone the aforementioned modification, and a functional fragment of the antibody, and specific examples of such an antibody include a deletion mutant comprising a deletion of 1 or 2 amino acids at the heavy chain carboxyl terminus, and a deletion mutant formed by amidating the aforementioned deletion mutant (e.g., a heavy chain in which the proline residue at the carboxyl-terminal site is amidated). However, deletion mutants involving a deletion at the carboxyl terminus of the heavy chain of the antibody according to the present invention are not limited to the above-described deletion mutants, as long as they retain antigen-binding activity and/or effector function. Two heavy chains constituting the antibody according to the present invention may be any one type of heavy chain selected from the group consisting of a full-length antibody and the above-described deletion mutants, or may be a combination of any two types selected from the aforementioned group. The ratio of individual deletion mutants can be influenced by the types of cultured mammalian cells that produce the antibody according to the present invention, and the culture conditions. Examples of the main ingredient of the antibody according to the present invention can include antibodies where one amino acid residue is deleted at each of the carboxyl termini of the two heavy chains.

Examples of the isotype of the antibody of the present invention can include IgG (IgG1, IgG2, IgG3, and IgG4). Among others, IgG1 and IgG2 are preferable.

Examples of the biological activity of an antibody can generally include antigen-binding activity, activity of being internalized into cells expressing an antigen by binding to the antigen, activity of neutralizing the activity of an antigen, activity of enhancing the activity of an antigen, antibody-dependent cellular cytotoxic (ADCC) activity, complement-dependent cytotoxic (CDC) activity, and antibody-dependent cellular phagocytosis (ADCP). The function of the antibody according to the present invention is binding activity against CD37 and is preferably the activity of being internalized into CD37-expressing cells by binding to CD37. Moreover, the antibody of the present invention may have ADCC activity, CDC activity and/or ADCP activity, as well as cellular internalization activity.

The obtained antibody can be purified to a homogenous state. For separation and purification of the antibody, separation and purification methods used for ordinary proteins may be used. For example, column chromatography, filtration, ultrafiltration, salting-out, dialysis, preparative polyacrylamide gel electrophoresis, and isoelectric focusing are appropriately selected and combined with one another, so that the antibody can be separated and purified (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though examples of the separation and purification methods are not limited thereto.

Examples of the chromatography can include affinity chromatography, ion exchange chromatography, hydrophobic chromatography, gel filtration chromatography, reverse phase chromatography, and absorption chromatography.

These chromatographic techniques can be carried out using liquid chromatography such as HPLC or FPLC.

Examples of the column used in the affinity chromatography can include a Protein A column and a Protein G column. Examples of columns that can be used as a Protein A column can include Hyper D, POROS, and Sepharose F. F. (Pharmacia).

Also, using an antigen-immobilized carrier, the antibody can be purified by utilizing the binding activity of the antibody to the antigen.

3. Anti-CD37 Antibody-Drug Conjugate (1) Drug

The anti-CD37 antibody obtained in the above "2. Production of anti-CD37 antibody" can be conjugated to a drug via a linker structure moiety to prepare an anti-CD37 antibody-drug conjugate. The drug is not particularly limited as long as it has a substituent or a partial structure that can be connected to a linker structure. The anti-CD37 antibody-drug conjugate can be used for various purposes according to the conjugated drug. Examples of such a drug can include substances having antitumor activity, substances effective for blood diseases, substances effective for autoimmune diseases, anti-inflammatory substances, antimicrobial substances, antifungal substances, antiparasitic substances, antiviral substances, and anti-anesthetic substances.

(1)-1 Antitumor Compound

An example using an antitumor compound as a compound to be conjugated in the anti-CD37 antibody-drug conjugate of the present invention will be described below. The antitumor compound is not particularly limited as long as the compound has an antitumor effect and has a substituent or a partial structure that can be connected to a linker structure. Upon cleavage of a part or the whole of the linker in tumor cells, the antitumor compound moiety is released so that the antitumor compound exhibits an antitumor effect. As the linker is cleaved at a connecting position with the drug, the antitumor compound is released in its original structure to exert its original antitumor effect.

As one example of the antitumor compound used in the present invention, exatecan, a camptothecin derivative ((1S, 9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione represented by the following formula) can preferably be used.

[Formula 5]

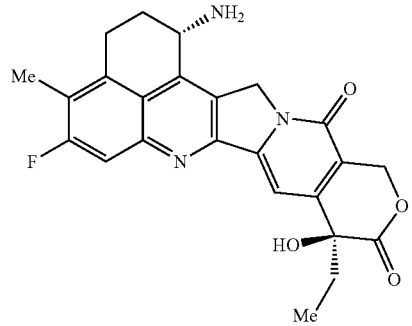

The compound can be easily obtained by, for example, a method described in U.S. Patent Publication No. 2016/0297890 or other known methods, and the amino group at position 1 can be preferably used as a connecting position to the linker structure. Further, exatecan may be released into tumor cells while a part of the linker is still attached thereto. However, the compound exerts an excellent antitumor effect even in such a state.

Since exatecan has a camptothecin structure, it is known that the equilibrium shifts to a structure with a formed lactone ring (closed ring) in an acidic aqueous medium (e.g., of the order of pH 3) whereas the equilibrium shifts to a structure with an opened lactone ring (open ring) in a basic aqueous medium (e.g., of the order of pH 10). A drug conjugate into which exatecan residues corresponding to such a closed ring structure and an open ring structure have been introduced is also expected to have an equivalent antitumor effect, and it is needless to say that any of such drug conjugate is included within the scope of the present invention.

Other examples of the antitumor compound can include antitumor compounds described in the literature (Pharmacological Reviews, 68, p. 3-19, 2016). Specific examples thereof can include doxorubicin, calicheamicin, dolastatin 10, auristatins such as monomethyl auristatin E (MMAE)

and monomethyl auristatin F (MMAF), maytansinoids such as DM1 and DM4, a pyrrolobenzodiazepine dimer SG2000 (SJG-136), a camptothecin derivative SN-38, duocarmycins such as CC-1065, amanitin, daunorubicin, mitomycin C, bleomycin, cyclocytidine, vincristine, vinblastine, methotrexate, platinum-based antitumor agents (cisplatin and derivatives thereof), and Taxol and derivatives thereof.

In the antibody-drug conjugate, the number of conjugated drug molecules per antibody molecule is a key factor having an influence on the efficacy and safety thereof. The production of the antibody-drug conjugate is carried out by specifying reaction conditions such as the amounts of starting materials and reagents used for reaction, so as to attain a constant number of conjugated drug molecules. Unlike the chemical reaction of a low-molecular-weight compound, a mixture containing different numbers of conjugated drug molecules is usually obtained. The number of conjugated drug molecules per antibody molecule is defined and indicated as an average value, i.e., the average number of conjugated drug molecules. Unless otherwise specified, i.e., except in the case of representing an antibody-drug conjugate having a specific number of conjugated drug molecules that is included in an antibody-drug conjugate mixture having different numbers of conjugated drug molecules, the number of conjugated drug molecules according to the present invention also means an average value as a rule. The number of exatecan molecules conjugated to an antibody molecule is controllable, and as an average number of conjugated drug molecules per antibody, approximately 1 to 10 exatecan molecules can be conjugated. The number of exatecan molecules is preferably 2 to 8, 3 to 8, 4 to 8, 5 to 8, 6 to 8, or 7 to 8, more preferably 5 to 8, further preferably 7 to 8, still further preferably about 8 or 8. It is to be noted that a person skilled in the art can design a reaction for conjugating a required number of drug molecules to an antibody molecule based on the description of Examples of the present application, and can obtain an antibody-drug conjugate with a controlled number of conjugated exatecan molecules.

(2) Linker Structure

The linker structure which conjugates the drug to the anti-CD37 antibody in the anti-CD37 antibody-drug conjugate of the present invention will be described.

In the antibody-drug conjugate of the present application, the linker structure which conjugates the anti-CD37 antibody to the drug is not particularly limited as long as the resulting antibody-drug conjugate can be used. The linker structure may be appropriately selected and used according to the purpose of use. One example of the linker structure can include a linker described in known literature (Pharmacol Rev 68:3-19, January 2016, Protein Cell DOI 10.1007/s13238-016-0323-0, etc.). Further specific examples thereof can include VC (valine-citrulline), MC (maleimidocaproyl), SMCC (succinimidyl 4-(N-maleimidomethyl) cyclohexane-1-carboxylate), SPP (N-succinimidyl 4-(2-pyridyldithio) pentanoate, SS (disulfide), SPDB (N-succinimidyl 4-(2-pyridyldithio) butyrate, SS/hydrazone, hydrazone and carbonate.

Another example thereof can include a linker structure described in U.S. Patent Publication No. 2016/0297890 (as one example, those described in the paragraphs [0260] to [0289] in the aforementioned patent publication literature). Any linker structure given below can be preferably used. It is to be noted that the left terminus of the structure is a connecting position to the antibody, and the right terminus thereof is a connecting position to the drug. Furthermore, GGFG in the linker structures given below represents an amino acid sequence consisting of glycine-glycine-phenylalanine-glycine (GGFG) linked through peptide bonds.

-(Succinimid-3-yl-N)—$CH_2CH_2$—C(=O)-GGFG-NH—$CH_2CH_2CH_2$—C(=O)—,

-(Succinimid-3-yl-N)—$CH_2CH_2CH_2CH_2CH_2$—C(=O)-GGFG-NH—$CH_2CH_2CH_2$—C(=O)—, -(Succinimid-3-yl-N)—$CH_2CH_2CH_2CH_2CH_2$—C(=O)-GGFG-NH—$CH_2$—O—$CH_2$—C(=O)—, -(Succinimid-3-yl-N)—$CH_2CH_2CH_2CH_2CH_2$—C(=O)-GGFG-NH—$CH_2CH_2$—O—$CH_2$—C(=O)—, -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, and -(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—.

More preferred are the following:

-(Succinimid-3-yl-N)—$CH_2CH_2CH_2CH_2CH_2$—C(=O)-GGFG-NH—$CH_2$—O—$CH_2$—C(=O)—, -(Succinimid-3-yl-N)—$CH_2CH_2CH_2CH_2CH_2$—C(=O)-GGFG-NH—$CH_2CH_2$—O—$CH_2$—C(=O)—, and -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

Still more preferred are the following:

-(Succinimid-3-yl-N)—$CH_2CH_2CH_2CH_2CH_2$—C(=O)-GGFG-NH—$CH_2$—O—$CH_2$—C(=O)—, and -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

The antibody is connected to the terminus of -(Succinimid-3-yl-N) (e.g., a terminus opposite (left terminus) to the terminus to which-$CH_2CH_2CH_2CH_2CH_2$— is connected in "-(Succinimid-3-yl-N)—$CH_2CH_2CH_2CH_2CH_2$—C(=O)-GGFG-NH—$CH_2$—O—$CH_2$—C(=O)—"), and the antitumor compound is connected to a terminus (the carbonyl group of $CH_2$—O—$CH_2$—C(=O)— at the right terminus in the above-described example) opposite to the terminus to which the antibody is connected to -(Succinimid-3-yl-N). "-(Succinimid-3-yl-N)—" has a structure represented by the following formula:

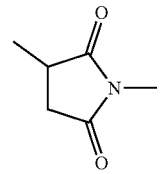

[Formula 6]

Position 3 of this partial structure is the connecting position to the anti-CD37 antibody. This connection to the antibody at position 3 is characterized by forming a thioether bond. The nitrogen atom at position 1 of this structural moiety is connected to the carbon atom of methylene which is present within the linker including this structure.

In the antibody-drug conjugate of the present invention having exatecan as the drug, a drug-linker structural moiety having any structure given below is preferred for conjugation to the antibody. For these drug-linker structural moieties, the average number conjugated per antibody may be 1 to 10 and is preferably 2 to 8, more preferably 5 to 8, further preferably 7 to 8, and still further preferably 8.

-(Succinimid-3-yl-N)—CH₂CH₂—C(=O)-GGFG-NH—CH₂CH₂CH₂—C(=O)—(NH-DX),
-(Succinimid-3-yl-N)—CH₂CH₂CH₂CH₂CH₂—C(=O)-GGFG-NH—CH₂CH₂CH₂—C(=O)—(NH-DX),
-(Succinimid-3-yl-N)—CH₂CH₂CH₂CH₂CH₂—C(=O)-GGFG-NH—CH₂—O—CH₂—C(=O)—(NH-DX),
-(Succinimid-3-yl-N)—CH₂CH₂CH₂CH₂CH₂—C(=O)-GGFG-NH—CH₂CH₂—O—CH₂—C(=O)—(NH-DX),
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX), and
-(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—(NH-DX).

More preferred are the following:
-(Succinimid-3-yl-N)—CH₂CH₂CH₂CH₂CH₂—C(=O)-GGFG-NH—CH₂—O—CH₂—C(=O)—(NH-DX),
-(Succinimid-3-yl-N)—CH₂CH₂CH₂CH₂CH₂—C(=O)-GGFG-NH—CH₂CH₂—O—CH₂—C(=O)—(NH-DX), and
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX).

Still more preferred are the following:
-(Succinimid-3-yl-N)—CH₂CH₂CH₂CH₂CH₂—C(=O)-GGFG-NH—CH₂—O—CH₂—C(=O)—(NH-DX), and
-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—(NH-DX).

—(NH-DX) has a structure represented by the following formula:

[Formula 7]

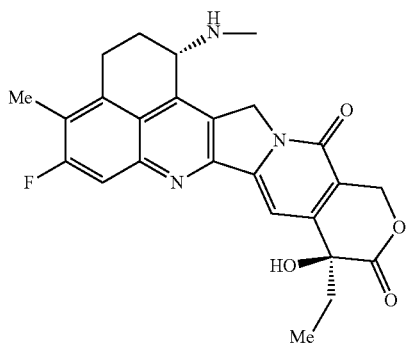

and it represents a group that is derived by removing one hydrogen atom from the amino group at position 1 of exatecan.

(3) Method for Producing Antibody-Drug Conjugate

The antibody that can be used in the antibody-drug conjugate of the present invention is not particularly limited as long as it is an anti-CD37 antibody having internalization activity or a functional fragment of the antibody, as described in the above section "2. Production of anti-CD37 antibody" and the Examples.

Next, a typical method for producing the antibody-drug conjugate of the present invention will be described. It is to be noted that, in the description below, "compound No." shown in each reaction scheme is used to represent a compound. Specifically, each compound is referred to as a "compound of formula (1)", "compound (1)", or the like. The same holds true for the other compound Nos.

(3)-1 Production Method 1

The antibody-drug conjugate represented by formula (1) given below in which the anti-CD37 antibody is connected to the linker structure via a thioether can be produced by reacting antibody AB having a sulfhydryl group converted from a disulfide bond by the reduction of the anti-CD37 antibody, with the compound (2) obtainable by a known method (e.g., obtainable by a method described in U.S. Patent Publication No. 2016/297890 (e.g., a method described in the paragraphs [0336] to [0374] in the aforementioned patent publication literature)). This antibody-drug conjugate can be produced by the following method, for example.

[Expression 1]

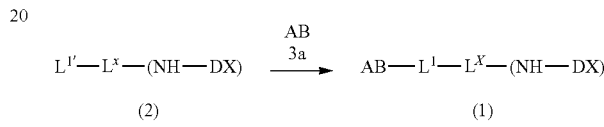

wherein AB represents an antibody with a sulfhydryl group, wherein

L¹ has a structure represented by -(Succinimid-3-yl-N)—, and

L¹' represents a maleimidyl group represented by the following formula.

[Formula 8]

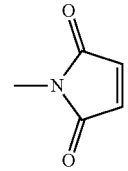

-L¹-L^X has a structure represented by any of the following formulas:

-(Succinimid-3-yl-N)—CH₂CH₂—C(=O)-GGFG-NH—CH₂CH₂CH₂—C(=O)—,

-(Succinimid-3-yl-N)—CH₂CH₂CH₂CH₂CH₂—C(=O)-GGFG-NH—CH₂CH₂CH₂—C(=O)—,

-(Succinimid-3-yl-N)—CH₂CH₂CH₂CH₂CH₂—C(=O)-GGFG-NH—CH₂—O—CH₂—C(=O)—,

-(Succinimid-3-yl-N)—CH₂CH₂CH₂CH₂CH₂—C(=O)-GGFG-NH—CH₂CH₂—O—CH₂—C(=O)—,

-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—, and -(Succinimid-3-yl-N)—CH₂CH₂—C(=O)—NH—CH₂CH₂O—CH₂CH₂O—CH₂CH₂O—CH₂CH₂O—CH₂CH₂—C(=O)-GGFG-NH—CH₂CH₂CH₂—C(=O)—.

Among them, more preferred are the following:

-(Succinimid-3-yl-N)—CH₂CH₂CH₂CH₂CH₂—C(=O)-GGFG-NH—CH₂—O—CH₂—C(=O)—,

-(Succinimid-3-yl-N)—CH₂CH₂CH₂CH₂CH₂—C(=O)-GGFG-NH—CH₂CH₂—O—CH₂—C(=O)—, and

-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—.

Further preferred are the following:

-(Succinimid-3-yl-N)—CH₂CH₂CH₂CH₂CH₂—C(=O)-GGFG-NH—CH₂—O—CH₂—C(=O)—, and

-(Succinimid-3-yl-N)—CH₂CH₂—C(=O)—NH—CH₂CH₂O—CH₂CH₂O—CH₂CH₂—C(=O)-GGFG-NH—CH₂CH₂CH₂—C(=O)—.

In the above-described reaction scheme, the antibody-drug conjugate (1) can be understood as having a structure in which one structure moiety from the drug to the linker terminus is connected to one antibody. However, this description is given for the sake of convenience, and there are actually many cases in which a plurality of the aforementioned structural moieties is connected to one antibody molecule. The same holds true for the explanation of the production method described below.

Specifically, the antibody-drug conjugate (1) can be produced by reacting the compound (2) obtainable by a known method (e.g., obtainable by a method described in U.S. Patent Publication No. 2016/297890 (e.g., a method described in the paragraphs [0336] to [0374] in the aforementioned patent publication literature)), with the antibody having a sulfhydryl group.

The antibody having a sulfhydryl group can be obtained by a method well known to a person skilled in the art (Hermanson, G. T, Bioconjugate Techniques, pp. 56-136, pp. 456-493, Academic Press (1996)). Examples of the method can include, but are not limited to: Traut's reagent being reacted with the amino group of the antibody; N-succinimidyl S-acetylthioalkanoates being reacted with the amino group of the antibody followed by reaction with hydroxylamine; N-succinimidyl 3-(pyridyldithio) propionate being reacted with the antibody, followed by reaction with a reducing agent; the antibody being reacted with a reducing agent such as dithiothreitol, 2-mercaptoethanol, or tris(2-carboxyethyl) phosphine hydrochloride (TCEP) to reduce the interchain disulfide bond in the antibody, so as to form a sulfhydryl group.

Specifically, an antibody with interchain disulfide bonds partially or completely reduced can be obtained by using 0.3 to 3 molar equivalents of TCEP as a reducing agent per interchain disulfide bond in the antibody, and reacting the reducing agent with the antibody in a buffer solution containing a chelating agent. Examples of the chelating agent can include ethylenediaminetetraacetic acid (EDTA) and diethylenetriaminepentaacetic acid (DTPA). The chelating agent can be used at a concentration of 1 mM to 20 mM. A solution of sodium phosphate, sodium borate, sodium acetate, or the like can be used as the buffer solution. As a specific example, the antibody having partially or completely reduced sulfhydryl groups can be obtained by reacting the antibody with TCEP at 4° C. to 37° C. for 1 hour to 4 hours.

It is to be noted that by carrying out an addition reaction of a sulfhydryl group to a drug-linker moiety, the drug-linker moiety can be conjugated by a thioether bond.

Then, using 2 to 20 molar equivalents of the compound (2) per antibody having a sulfhydryl group, the antibody-drug conjugate (1) in which 2 to 8 drug molecules are conjugated per antibody can be produced. Specifically, a solution containing the compound (2) dissolved therein may be added to a buffer solution containing the antibody (3a) having a sulfhydryl group for the reaction. In this context, a sodium acetate solution, sodium phosphate, sodium borate, or the like can be used as the buffer solution. pH for the reaction is 5 to 9, and more preferably, the reaction may be performed near pH 7. An organic solvent such as dimethyl sulfoxide (DMSO), dimethylformamide (DMF), dimethylacetamide (DMA), or N-methyl-2-pyrrolidone (NMP) can be used as a solvent for dissolving the compound (2). The reaction may be performed by adding the solution containing the compound (2) dissolved in the organic solvent at 1 to 20% v/v to a buffer solution containing the antibody having a sulfhydryl group. The reaction temperature is 0° C. to 37° C., more preferably 10° C. to 25° C., and the reaction time is 0.5 hours to 2 hours. The reaction can be terminated by deactivating the reactivity of unreacted compound (2) with a thiol-containing reagent. The thiol-containing reagent is, for example, cysteine or N-acetyl-L-cysteine (NAC). More specifically, the reaction can be terminated by adding 1 to 2 molar equivalents of NAC to the compound (2) used, and incubating the obtained mixture at room temperature for 10 minutes to 30 minutes.

(4) Identification of Antibody-Drug Conjugate

The produced antibody-drug conjugate (1) can be subjected to concentration, buffer exchange, purification, and measurement of antibody concentration and the average number of conjugated drug molecules per antibody molecule according to common procedures described below, to identify the antibody-drug conjugate (1).

(4)-1 Common Procedure A: Concentration of Aqueous Solution of Antibody or Antibody-Drug Conjugate To an Amicon Ultra (50,000 MWCO, Millipore Corporation) container, a solution of an antibody or an antibody-drug conjugate was added, and the solution of the antibody or the antibody-drug conjugate was concentrated by centrifugation (centrifugation at 2000 G to 3800 G for 5 to 20 minutes) using a centrifuge (Allegra X-15R, Beckman Coulter, Inc.)

(4)-2 Common Procedure B: Measurement of Antibody Concentration

Using a UV detector (Nanodrop 1000, Thermo Fisher Scientific Inc.), measurement of the antibody concentration was carried out according to the method defined by the manufacturer. In this respect, 280 nm absorption coefficient differing among antibodies (1.3 mLmg$^{-1}$ cm$^{-1}$ to 1.8 mLmg$^{-1}$ cm$^{-1}$) was used.

(4)-3 Common Procedure C: Buffer Exchange for Antibody

A NAP-25 column (Cat. No. 17-0852-02, GE Healthcare Japan Corporation) using Sephadex G-25 carrier was equilibrated with a phosphate buffer (50 mM, pH 6.0) (referred to as PBS6.0/EDTA in the present description) containing sodium chloride (50 mM) and EDTA (2 mM) according to the method defined by the manufacturer. An aqueous solution of the antibody was applied in an amount of 2.5 mL per NAP-25 column, and thereafter, a fraction (3.5 mL) eluted with 3.5 mL of PBS6.0/EDTA was collected. This fraction was concentrated by common procedure A. After measurement of the concentration of the antibody using common procedure B, the antibody concentration was adjusted to 10 mg/mL using PBS6.0/EDTA.

(4)-4 Common Procedure D: Purification of Antibody-Drug Conjugate

A NAP-25 column was equilibrated with any commercially available buffer solution such as an acetate buffer containing sorbitol (5%) (10 mM, pH 5.5; referred to as ABS in the present description). An aqueous reaction solution of the antibody-drug conjugate (approximately 2.5 mL) was applied to the NAP-25 column, and thereafter, elution was carried out with the buffer solution in an amount defined by the manufacturer, so as to collect an antibody fraction. A gel filtration purification process, in which the collected fraction was applied again to the NAP-25 column, and elution was carried out with the buffer solution, was repeated a total of 2 or 3 times to obtain the antibody-drug conjugate excluding non-conjugated drug linker and low-molecular-weight compounds (tris(2-carboxyethyl) phosphine hydrochloride (TCEP), N-acetyl-L-cysteine (NAC), and dimethyl sulfoxide).

(4)-5 Common Procedure E: Measurement (1) of Antibody Concentration in Antibody-Drug Conjugate and Average Number of Conjugated Drug Molecules Per Antibody Molecule The conjugated drug concentration in the antibody-drug conjugate can be calculated by measuring UV absorbance of an aqueous solution of the antibody-drug conjugate at two wavelengths of 280 nm and 370 nm, and thereafter performing the calculation shown below.

The total absorbance at any given wavelength is equal to the sum of the absorbance of all light-absorbing chemical species that are present in a system [additivity of absorbance]. Therefore, based on the hypothesis that the molar absorption coefficients of the antibody and the drug do not vary between before and after conjugation between the antibody and the drug, the antibody concentration and the drug concentration in the antibody-drug conjugate are represented by the following equations.

$$A_{280} = A_{D,280} + A_{A,280} = \varepsilon_{D,280} C_D + \varepsilon_{A,280} C_A \quad \text{Equation (1)}$$

$$A_{370} = A_{D,370} + A_{A,370} = \varepsilon_{D,370} C_D + \varepsilon_{A,370} C_A \quad \text{Equation (2)}$$

In this context, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of the antibody at 280 nm, $A_{A,370}$ represents the absorbance of the antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of the antibody at 280 nm, $\varepsilon_{A,370}$ represents the molar absorption coefficient of the antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in the antibody-drug conjugate, and $C_D$ represents the drug concentration in the antibody-drug conjugate.

In this context, with regard to $\varepsilon_{A,280}$, $\varepsilon_{A,370}$, $\varepsilon_{D,280}$, and $\varepsilon_{D,370}$, preliminarily prepared values (estimated values based on calculation or measurement values obtained by UV measurement of the compound) are used. For example, $\varepsilon_{A,280}$ can be estimated from the amino acid sequence of the antibody by a known calculation method (Protein Science, 1995, vol. 4, 2411-2423). $\varepsilon_{A,370}$ is generally zero. $\varepsilon_{D,280}$ and $\varepsilon_{D,370}$ can be obtained according to Lambert-Beer's law (Absorbance=Molar concentration×Molar absorption coefficient×Cell path length) by measuring the absorbance of a solution in which the conjugate precursor used is dissolved at a certain molar concentration. $C_A$ and $C_D$ can be determined by measuring $A_{280}$ and $A_{370}$ of an aqueous solution of the antibody-drug conjugate, and then solving the simultaneous equations (1) and (2) by substitution of these values. Further, by dividing $C_D$ by $C_A$, the average number of conjugated drug molecules per antibody can be determined.

(4)-6 Common Procedure F: Measurement of Average Number of Conjugated Drug Molecules Per Antibody Molecule in Antibody-Drug Conjugate—(2)

The average number of conjugated drug molecules per antibody molecule in the antibody-drug conjugate can also be determined by high-performance liquid chromatography (HPLC) analysis using the following method, in addition to the aforementioned "(4)-5 Common procedure E". Hereinafter, the method for measuring the average number of conjugated drug molecules by HPLC when the antibody is conjugated to the drug linker by a disulfide bond will be described. A person skilled in the art is capable of appropriately measuring the average number of conjugated drug molecules by HPLC, depending on the connecting manner between the antibody and the drug linker, with reference to this method.

F-1. Preparation of Sample for HPLC Analysis (Reduction of Antibody-Drug Conjugate)

An antibody-drug conjugate solution (approximately 1 mg/mL, 60 μL) is mixed with an aqueous solution of dithiothreitol (DTT) (100 mM, 15 μL). By incubating the mixture at 37° C. for 30 minutes, the disulfide bond between the light chain and heavy chain of the antibody-drug conjugate is cleaved. The resulting sample is used in HPLC analysis.

F-2. HPLC Analysis

The HPLC analysis is carried out under the following measurement conditions.

HPLC system: Agilent 1290 HPLC system (Agilent Technologies, Inc.)

Detector: Ultraviolet absorption spectrometer (measurement wavelength: 280 nm)

Column: ACQUITY UPLC BEH Phenyl (2.1×50 mm, 1.7 μm, 130 angstroms; Waters Corp., P/N 186002884)

Column temperature: 80° C.

Mobile phase A: Aqueous solution containing 0.10% trifluoroacetic acid (TFA) and 15% 2-propanol Mobile phase B: Acetonitrile solution containing 0.075% TFA and 15% 2-propanol Gradient program: 14%-36% (0 min-15 min), 36%-80% (15 min-17 min), 80%-14% (17 min-17.01 min), and 14% (17.01 min-25 min)

Sample injection: 10 μL

F-3. Data Analysis

F-3-1. Compared with non-conjugated antibody light (L0) and heavy (H0) chains, a light chain bound to drug molecule(s) (light chain bound to i drug molecule(s): $L_i$) and a heavy chain bound to drug molecule(s) (heavy chain bound to i drug molecule(s): $H_i$) exhibit higher hydrophobicity in proportion to the number of conjugated drug molecules and thus have a larger retention time. These chains are therefore eluted in the order of, for example, L0 and L1 or H0, H1, H2, and H3. Detection peaks can be assigned to any of L0, L1, H0, H1, H2, and H3 by the comparison of retention times with L0 and H0. The number of conjugated drug molecules can be defined by a person skilled in the art, but is preferably L0, L1, H0, H1, H2, and H3.

F-3-2. Since the drug linker has UV absorption, peak area values are corrected in response to the number of conjugated drug linker molecules according to the following expression using the molar absorption coefficients of the light chain or heavy chain and the drug linker.

[Expression 2]

Corrected value of peak area of light chain bound to $i$ drug molecule(s)$(A_{Li})$ =

$$\text{Peak area} \times \frac{\text{Molar absorption coefficient of light chain}}{\begin{array}{c}\text{Molar absorption coefficient of light chain} + \\ \text{The number of conjugated drug molecules } (i) \times \\ \text{Molar absorption coefficient of drug linker}\end{array}}$$

[Expression 3]

Corrected value of peak area of heavy chain bound to $i$ drug molecule(s)$(A_{Hi})$ =

$$\text{Peak area} \times \frac{\text{Molar absorption coefficient of heavy chain}}{\begin{array}{c}\text{Molar absorption coefficient of heavy chain} + \\ \text{The number of conjugated drug molecules } (i) \times \\ \text{Molar absorption coefficient of drug linker}\end{array}}$$

In this context, a value estimated from the amino acid sequence of the light chain or heavy chain of each antibody by a known calculation method (Protein Science, 1995, vol. 4, 2411-2423) can be used as the molar absorption coefficient (280 nm) of the light chain or heavy chain of the antibody. In the case of H01L02, a molar absorption coefficient of 31710 and a molar absorption coefficient of 79990 were used as estimated values for the light chain and heavy chain, respectively, according to the amino acid sequence of the antibody. The actually measured molar absorption coefficient (280 nm) of a compound in which the maleimide group has been converted to succinimide thioether by the reaction of each drug linker with mercaptoethanol or N-acetylcysteine was used as the molar absorption coefficient (280 nm) of the drug linker. The wavelength for absorbance measurement can be appropriately set by a person skilled in the art, but is preferably a wavelength at which the peak of the antibody can be measured, and more preferably 280 nm.

F-3-3. The peak area ratio (%) of each chain is calculated for the total of the corrected values of peak areas according to the following expression.

[Expression 4]

Peak area ratio of light chain bound to $i$ drug molecule(s) =

$$\frac{A_{Li}}{A_{L0} + A_{L1}} \times 100$$

Peak area ratio of heavy chain bound to $i$ drug molecule(s) =

$$\frac{A_{Hi}}{A_{H0} + A_{H1} + A_{H2} + A_{H3}} \times 100$$

$A_{Li}$, $A_{Hi}$: Corrected values of peak areas of $Li$ and $Hi$, respectively F-3-4. The average number of conjugated drug molecules per antibody molecule in the antibody-drug conjugate is calculated according to the following expression.

Average number of conjugated drug molecules=($L_0$ peak area ratio×0+$L_1$ peak area ratio×1+$H_0$ peak area ratio×0+$H_1$ peak area ratio×1+$H_2$ peak area ratio×2+$H_3$ peak area ratio×3)/100×2

It is to be noted that, in order to secure the amount of the antibody-drug conjugate, a plurality of antibody-drug conjugates having almost the same average number of conjugated drug molecules (e.g., on the order of ±1), which have been produced under similar conditions, can be mixed to prepare a new lot. In this case, the average number of conjugated drug molecules of the new lot falls between the average numbers of conjugated drug molecules before the mixing.

One specific example of the antibody-drug conjugate of the present invention can include an antibody-drug conjugate having a structure represented by the following formula:

[Formula 9]

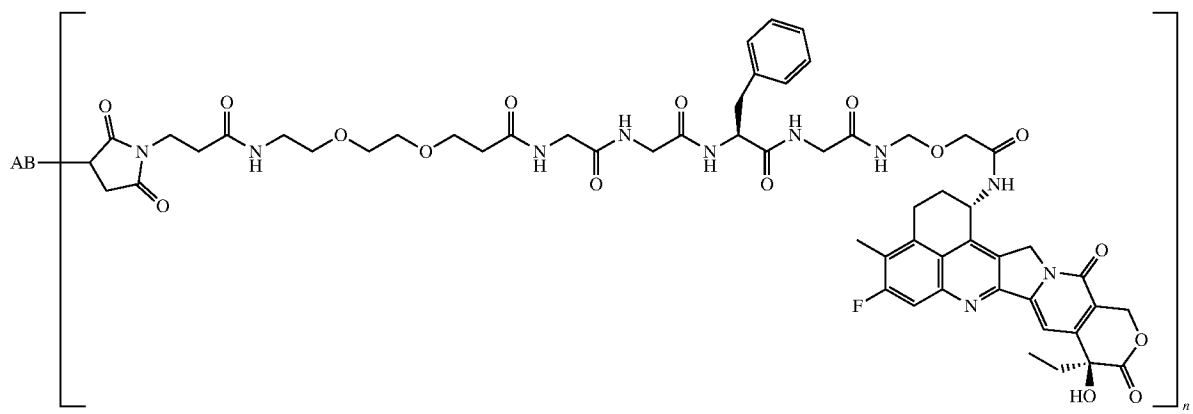

or the following formula:

[Formula 10]

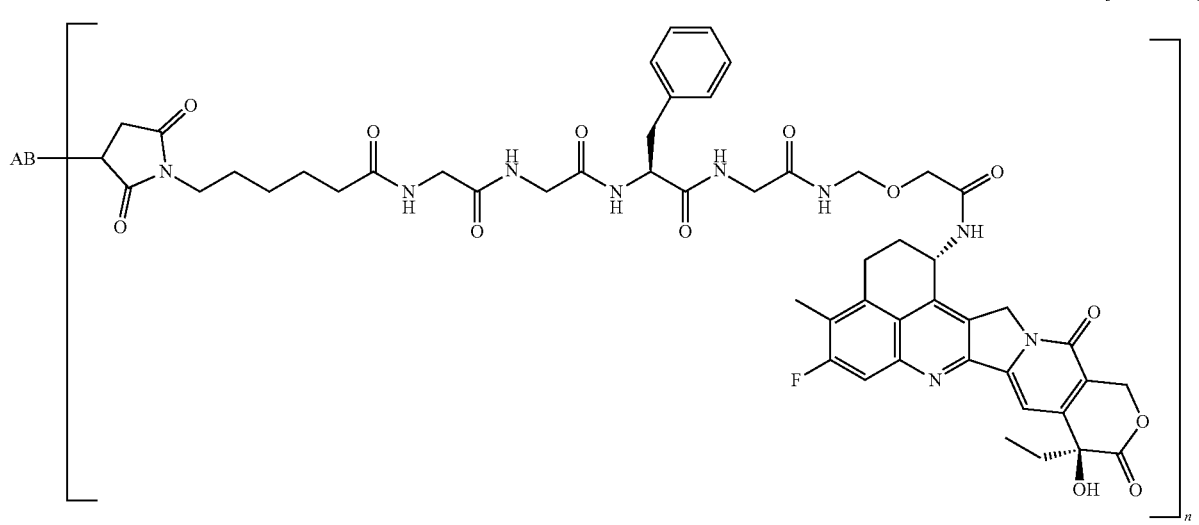

In this context, AB represents the anti-CD37 antibody disclosed in the present description, and the antibody is conjugated to the drug linker via a sulfhydryl group stemming from the antibody. In this context, n has the same meaning as that of the so-called DAR (drug-to-antibody Ratio), and represents a drug-to-antibody ratio per antibody. Specifically, n represents the number of conjugated drug molecules per antibody molecule, which is a numeric value defined and indicated as an average value, i.e., the average number of conjugated drug molecules. In the case of the antibody-drug conjugate represented by Formula 9 or Formula 10 of the present invention, n can be 2 to 8 and is preferably 5 to 8, more preferably 7 to 8, and still more preferably 8, in measurement by common procedure F.

One example of the antibody-drug conjugate of the present invention can include an antibody-drug conjugate having a structure represented by the above-described formula Formula 9 or Formula 10 wherein the antibody represented by AB comprises any one antibody consisting of heavy chain and light chain selected from the group consisting of the following antibodies (a) to (e), or a functional fragment of the antibody, or a pharmacologically acceptable salt of the antibody-drug conjugate:

(a) an antibody consisting of a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 4;

(b) an antibody consisting of a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;

(c) an antibody consisting of a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8;

(d) an antibody consisting of a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10; and (e) any one antibody selected from the group consisting of the antibodies (a) to (d), wherein the heavy chain or the light chain comprises one or two or more modifications selected from the group consisting of post-translational modifications typified by N-linked glycosylation, O-linked glycosylation, amino-terminal processing, carboxyl-terminal processing, deamidation, isomerization of aspartic acid, oxidation of methionine, oxidation of tryptophan, addition of a methionine residue to the amino terminus, amidation of a proline residue, and conversion of amino-terminal glutamine or amino-terminal glutamic acid to pyroglutamic acid, and a deletion of one or two amino acids from the carboxyl terminus.

4. Medicament

Since the anti-CD37 antibody of the present invention or the functional fragment of the antibody described in the above section "2. Production of anti-CD37 antibody" and the Examples binds to CD37 on the surface of tumor cells and has internalization activity, it can be used as a medicament, and in particular, as a therapeutic agent for B-cell non-Hodgkin's lymphoma (NHL) (e.g., diffuse large B-cell lymphoma (DLBCL), follicular lymphoma (FL), mantle cell lymphoma (MCL), marginal zone lymphoma (MZL), and Burkitt's lymphoma (BL)), chronic lymphocytic leukemia (CLL), T-cell lymphoma (TCL) such as peripheral T-cell lymphoma (PTCL) or cutaneous T-cell lymphoma (CTCL), and further, myelodysplastic syndrome (MDS) and acute myeloid leukemia (AML).

Furthermore, the anti-CD37 antibody of the present invention or the functional fragment of the antibody can be used in the detection of cells expressing CD37.

Moreover, since the anti-CD37 antibody of the present invention or the functional fragment of the antibody has internalization activity, it can be applied as the antibody in an antibody-drug conjugate.

When a drug having antitumor activity such as cytotoxic activity is used as the drug, the anti-CD37 antibody-drug conjugate of the present invention described in the above section "3. Anti-CD37 antibody-drug conjugate" and the Examples is a conjugate of the anti-CD37 antibody and/or the functional fragment of the antibody having internalization activity, and the drug having antitumor activity such as cytotoxic activity. Since this anti-CD37 antibody-drug conjugate exhibits antitumor activity against cancer cells expressing CD37, it can be used as a medicament, and in particular, as a therapeutic agent and/or a prophylactic agent for cancer.

The anti-CD37 antibody-drug conjugate of the present invention may absorb moisture or have adsorption water, for example, to turn into a hydrate when it is left in air or subjected to recrystallization or purification procedures. Such a compound or a pharmacologically acceptable salt containing water is also included in the present invention.

When the anti-CD37 antibody-drug conjugate of the present invention has a basic group such as an amino group, it can form a pharmacologically acceptable acid-addition salt, if desired. Examples of such an acid-addition salt can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as formate, acetate, trifluoroacetate, malate, fumarate, succinate, citrate, tartrate, oxalate, and maleate; and amino acid salts such as ornithine salt, glutamate, and aspartate.

When the anti-CD37 antibody-drug conjugate of the present invention has an acidic group such as a carboxy group, it can form a pharmacologically acceptable base-addition salt, if desired. Examples of such a base-addition salt can include: alkali metal salts such as a sodium salt, a potassium salt, and a lithium salt; alkaline earth metal salts such as a calcium salt and a magnesium salt; inorganic salts such as an ammonium salt; and organic amine salts such as a dibenzylamine salt, a morpholine salt, a phenylglycine alkyl ester salt, an ethylenediamine salt, an N-methylglucamine salt, a diethylamine salt, a triethylamine salt, a cyclohexylamine salt, a dicyclohexylamine salt, an N,N'-dibenzylethylenediamine salt, a diethanolamine salt, an N-benzyl-N-(2-phenylethoxy)amine salt, a piperazine salt, a tetramethylammonium salt, and a tris(hydroxymethyl)aminomethane salt.

The present invention can also include an anti-CD37 antibody-drug conjugate in which one or more atoms constituting the antibody-drug conjugate are replaced with isotopes of the atoms. There exist two types of isotopes: radioisotopes and stable isotopes. Examples of the isotope can include isotopes of hydrogen (2H and 3H), isotopes of carbon (11C, 13C and 14C), isotopes of nitrogen (13N and 15N), isotopes of oxygen (15O, 17O and 18O), and isotopes of fluorine (18F). A composition comprising the antibody-drug conjugate labeled with such an isotope is useful as, for example, a therapeutic agent, a prophylactic agent, a research reagent, an assay reagent, a diagnostic agent, and an in vivo diagnostic imaging agent. Each and every antibody-drug conjugate labeled with an isotope, and mixtures of antibody-drug conjugates labeled with an isotope at any given ratio are included in the present invention. The antibody-drug conjugate labeled with an isotope can be produced, for example, by using a starting material labeled with an isotope, instead of a starting material for the production method of the present invention mentioned later, according to a method known in the art.

In vitro cytotoxicity can be measured based on the activity of suppressing the proliferative responses of cells, for example. For example, a cancer cell line overexpressing CD37 is cultured, and the anti-CD37 antibody-drug conjugate is added at different concentrations to the culture system. Thereafter, its suppressive activity against focus formation, colony formation and spheroid growth can be measured. In this context, for example, by using a diffuse large B-cell lymphoma (DLBCL)-, follicular lymphoma (FL)-, or chronic lymphocytic leukemia (CLL)-derived cancer cell line, cell growth inhibition activity against diffuse large B-cell lymphoma (DLBCL), follicular lymphoma (FL), chronic lymphocytic leukemia (CLL), or the like can be examined.

In vivo therapeutic effects on cancer in an experimental animal can be measured, for example, by administering the anti-CD37 antibody-drug conjugate to a SCID mouse into which a tumor cell line highly expressing CD37 has been inoculated, and then measuring a change in the cancer cells. In this context, for example, by using an animal model derived from an immunodeficient mouse by the inoculation of cells derived from B-cell non-Hodgkin's lymphoma (NHL) such as diffuse large B-cell lymphoma (DLBCL), follicular lymphoma (FL), mantle cell lymphoma (MCL), marginal zone lymphoma (MZL), or Burkitt's lymphoma (BL), chronic lymphocytic leukemia (CLL), T-cell lymphoma (TCL) such as peripheral T-cell lymphoma (PTCL) or cutaneous T-cell lymphoma (CTCL), myelodysplastic syndrome (MDS), or acute myeloid leukemia (AML), therapeutic effects on diffuse large B-cell lymphoma (DLBCL), follicular lymphoma (FL), mantle cell lymphoma (MCL), marginal zone lymphoma (MZL), Burkitt's lymphoma (BL), chronic lymphocytic leukemia (CLL), peripheral T-cell lymphoma (PTCL), cutaneous T-cell lymphoma (CTCL), myelodysplastic syndrome (MDS), or acute myeloid leukemia (AML) can be measured.

The type of cancer to which the anti-CD37 antibody-drug conjugate of the present invention is applied is not particularly limited as long as the cancer expresses CD37 in cancer cells to be treated. Examples thereof can include cells derived from diffuse large B-cell lymphoma, follicular lymphoma, mantle cell lymphoma, marginal zone lymphoma, Burkitt's lymphoma, or chronic lymphocytic leukemia, though the cancer is not limited thereto as long as the cancer expresses CD37. More preferred examples of the type of the cancer to which the anti-CD37 antibody-drug conjugate of the present invention is applied can include diffuse large B-cell lymphoma, follicular lymphoma, mantle cell lymphoma, and chronic lymphocytic leukemia.

The anti-CD37 antibody-drug conjugate of the present invention can preferably be administered to a mammal, and more preferably to a human.

A substance used in a pharmaceutical composition comprising the anti-CD37 antibody-drug conjugate of the present invention can be appropriately selected from pharmaceutical additives and others usually used in this field, in terms of the applied dose or the applied concentration, and then used.

The anti-CD37 antibody-drug conjugate of the present invention can be administered as a pharmaceutical composition comprising one or more pharmaceutically compatible components. For example, the pharmaceutical composition typically comprises one or more pharmaceutical carriers (e.g., sterilized liquids (e.g., water and oil (including petroleum oil and oil of animal origin, plant origin, or synthetic origin (e.g., peanut oil, soybean oil, mineral oil, and sesame oil))). Water is a more typical carrier when the pharmaceutical composition is intravenously administered. An aqueous saline solution, an aqueous dextrose solution, and an aqueous glycerol solution can also be used as a liquid carrier, in particular, for an injection solution. Suitable pharmaceutical vehicles are known in the art. If desired, the composition may also comprise a trace amount of a moisturizing agent, an emulsifying agent, or a pH buffering agent. Examples of suitable pharmaceutical carriers are disclosed in "Remington's Pharmaceutical Sciences" by E. W. Martin. The prescription corresponds to an administration mode.

Various delivery systems are known, and they can be used for administering the anti-CD37 antibody-drug conjugate of the present invention. Examples of the administration route can include, but are not limited to, intradermal, intramuscular, intraperitoneal, intravenous, and subcutaneous routes. The administration can be made by injection or bolus injection, for example. According to a specific preferred embodiment, the administration of the above-described antibody-drug conjugate is performed by injection. Parenteral administration is a preferred administration route.

According to a representative embodiment, the pharmaceutical composition is prescribed, as a pharmaceutical composition suitable for intravenous administration to a human, according to conventional procedures. The composition for intravenous administration is typically a solution in a sterile and isotonic aqueous buffer solution. If necessary, the medicament may also contain a solubilizing agent and a local anesthetic to alleviate pain at an injection area (e.g., lignocaine). In general, the above-described ingredients are provided, either separately or together in a mixture in unit dosage form, as a freeze-dried powder or an anhydrous concentrate contained in a container which is obtained by sealing in, for example, an ampoule or a sachet indicating the amount of the active agent. When the medicament is to be administered by injection, it may be administered using, for example, an injection bottle containing water or saline of sterile pharmaceutical grade. When the medicament is to be administered by injection, an ampoule of sterile water or saline for injection may be provided such that the above-described ingredients are admixed with one another before administration. The saline can be, for example, physiological saline.

Such a pharmaceutical composition can be prepared as a formulation having a selected composition and a necessary purity in the form of a freeze-dried formulation or a liquid formulation. The pharmaceutical composition prepared as a freeze-dried formulation may be a formulation containing an appropriate pharmaceutical additive used in this field. Likewise, the liquid formulation can be prepared such that the liquid formulation contains various pharmaceutical additives used in this field.

The composition and concentration of the pharmaceutical composition also vary depending on the administration method. With regard to the affinity of the anti-CD37 antibody-drug conjugate comprised in the pharmaceutical composition of the present invention for the antigen, i.e., the dissociation constant (Kd value) of the anti-CD37 antibody-drug conjugate to the antigen, as the affinity increases (i.e., the Kd value is low), the pharmaceutical composition can exert medicinal effects, even if the applied dose thereof is decreased. Accordingly, the applied dose of the antibody-drug conjugate can also be determined by setting the applied dose based on the status of the affinity of the antibody-drug conjugate for the antigen. When the antibody-drug conjugate of the present invention is administered to a human, it may be administered at a dose of, for example, from approximately 0.001 to 100 mg/kg once or a plurality of times at intervals of 1 to 180 days. It can be administered preferably at a dose of from 0.1 to 50 mg/kg and more preferably 0.1 to 30 mg/kg a plurality of times at intervals of 1 to 4 weeks, preferably 2 to 3 weeks.

EXAMPLES

Example 1: Production of Humanized Anti-CD37 Antibody

1)-1 Design of Anti-CD37 Humanized Antibody
1)-1-1 Molecular Modeling of Variable Region of Anti-CD37 Antibody.

A known method (Methods in Enzymology, 203, 121-153, (1991)) was exploited as homology modeling. The commercially available protein three-dimensional structure analysis program DiscoveryStudio (manufactured by Dassault Systèmes S.E.) was employed to search for structures registered in the Protein Data Bank (Nuc. Acid Res. 35, D301-D303 (2007)) with a high sequence homology to variable regions. Three-dimensional model structures were produced using the identified heavy chain, light chain, and interfacial structure between the heavy chain and the light chain as templates.

1)-1-2 Design Method for Humanization

Construction of a humanized antibody of the anti-CD37 mouse monoclonal antibody HH1 (Smeland E, et al., Scand J Immunol, 21 (3), 205-214 (1985)) was performed by a method generally known as CDR grafting (Proc. Natl. Acad. Sci. USA 86, 10029-10033 (1989)). The consensus sequences of human κ chain subgroup 1 and human γ chain subgroup 1 determined by KABAT et al. (Sequences of Proteins of Immunological Interest, 5th Ed. Public Health Service National Institutes of Health, Bethesda, MD. (1991)) had a high homology to the framework regions of an anti-CD37 human chimeric antibody, and based on this, they were selected as acceptors for the light chain and the heavy chain of the anti-CD37 human chimeric antibody, respectively. Also, human γ chain IGHV1-2*02 and IGHJ6*01 determined by IMGT (registered trademark) (THE INTERNATIONAL IMMUNOGENETICS INFORMATION SYSTEM) were selected as acceptors for the heavy chain for the purpose of improving the physical properties of an anti-CD37 humanized antibody-drug conjugate. Donor residues to be grafted onto the acceptors were uniquely designed according to each sequence by analyzing three-dimensional models with reference to, for example, the criteria given by Queen et al. (Proc. Natl. Acad. Sci. USA 86, 10029-10033 (1989)).

1)-1-3 Humanization of Anti-CD37 Human Chimeric Antibody Light Chain

A humanized antibody light chain comprising a human IgG1 κ chain constant region connected to the variable region of the designed anti-CD37 humanized antibody light chain was designed and named hmAb-L11. The full-length amino acid sequence of hmAb-L11 is shown in SEQ ID NO: 2. A nucleotide sequence encoding the amino acid sequence of SEQ ID NO: 2 is shown in SEQ ID NO: 1.

1)-1-4 Humanization of Anti-CD37 Human Chimeric Antibody Heavy Chain hmAb-H11

A humanized antibody heavy chain comprising a human IgG1 γ chain constant region connected to the variable region of the anti-CD37 humanized antibody heavy chain designed by grafting into the consensus sequence of human γ chain subgroup 1 having the highest homology to the anti-CD37 human chimeric antibody was designed and named hmAb-H11. The full-length amino acid sequence of hmAb-H11 is shown in SEQ ID NO: 4. A nucleotide sequence encoding the amino acid sequence of SEQ ID NO: 4 is shown in SEQ ID NO: 3.

1)-1-5 Humanization of Anti-CD37 Human Chimeric Antibody Heavy Chain hmAb-H541, hmAb-H551, hmAb-H11a Humanized antibody heavy chains comprising a human IgG1 γ chain constant region connected to the variable regions of the anti-CD37 humanized antibody heavy chains designed for the purpose of improving the physical properties of an anti-CD37 humanized antibody-drug conjugate were named hmAb-H541, hmAb-H551, and hmAb-H11a, respectively. The full-length amino acid sequence of hmAb-H541 is shown in SEQ ID NO: 6. A nucleotide sequence encoding the amino acid sequence of SEQ ID NO: 6 is shown in SEQ ID NO: 5. The full-length amino acid sequence of hmAb-H551 is shown in SEQ ID NO: 8. A nucleotide sequence encoding the amino acid sequence of SEQ ID NO: 8 is shown in SEQ ID NO: 7. The full-length amino acid sequence of hmAb-H11a is shown in SEQ ID NO: 10. A nucleotide sequence encoding the amino acid sequence of SEQ ID NO: 10 is shown in SEQ ID NO: 9.

1)-2 Construction of Anti-CD37 Humanized Antibody Expression Vector and Preparation of Antibody 1)-2-1 Construction of Light Chain Expression Vector pCMA-LK An approx. 5.4-kb fragment, which had been obtained by digesting plasmid pcDNA3.3-TOPO/LacZ (manufactured by Thermo Fisher Scientific Inc.) with the restriction enzymes XbaI and PmeI, was ligated to a DNA fragment comprising a nucleotide sequence (SEQ ID NO: 11) encoding a human light chain signal sequence and a human κ chain constant region, using an In-Fusion HD PCR cloning kit (manufactured by Takara Bio USA), to produce pcDNA3.3/LK.

A neomycin resistance gene was removed from pcDNA3.3/LK to construct pCMA-LK.

1)-2-1-1 Construction of hmAb-L11 Expression Vector

A DNA having the nucleotide sequence of the hmAb-L11 variable region shown in SEQ ID NO: 12 was synthesized (manufactured by Thermo Fisher Scientific Inc.). Using an In-Fusion HD PCR cloning kit, the synthesized DNA fragment was inserted into a site of pCMA-LK constructed in Example 1)-2-1 that had been cleaved with the restriction enzyme BsiWI, so as to construct a hmAb-L11 expression vector.

1)-2-2 Construction of Heavy Chain Expression Vector pCMA-G1

A DNA fragment comprising a nucleotide sequence (SEQ ID NO: 13) encoding a heavy chain signal sequence and a human heavy chain G1 constant region was synthesized (manufactured by Eurofins Genomics K.K.). This DNA fragment was cleaved with the restriction enzymes XbaI and PmeI, and a 1.1-kb DNA fragment was then excised by agarose gel electrophoresis and purified using Wizard SV Gel and PCR Clean-Up System (manufactured by Promega Corp.). An approx. 3.4-kb fragment, which had been obtained by digesting pCMA-LK constructed in Example 1)-2-1 with the restriction enzymes XbaI and PmeI, was ligated to the 1.1-kb DNA fragment, using Ligation High (manufactured by Toyobo Co., Ltd.), to construct pCMA-G1.

1)-2-2-1 Construction of hmAb-H11 Expression Vector

A DNA having the nucleotide sequence of hmAb-H11 shown in SEQ ID NO: 14 was synthesized. Using an In-Fusion HD PCR cloning kit, the synthesized DNA fragment was inserted into a site of pCMA-G1 constructed in Example 1)-2-1 that had been cleaved with the restriction enzyme BlpI, so as to construct a hmAb-H11 expression vector.

1)-2-2-2 Construction of hmAb-H541 Expression Vector

A DNA having the nucleotide sequence of hmAb-H541 shown in SEQ ID NO: 15 was synthesized. Using an In-Fusion HD PCR cloning kit, the synthesized DNA fragment was inserted into a site of pCMA-G1 constructed in Example 1)-2-1 that had been cleaved with the restriction enzyme BlpI, so as to construct a hmAb-H541 expression vector.

1)-2-2-3 Construction of hmAb-H551 Expression Vector

A DNA having the nucleotide sequence of hmAb-H551 shown in SEQ ID NO: 16 was synthesized. Using an In-Fusion HD PCR cloning kit, the synthesized DNA fragment was inserted into a site of pCMA-G1 constructed in Example 1)-2-1 that had been cleaved with the restriction enzyme BlpI, so as to construct a hmAb-H551 expression vector.

1-2-2-4 Construction of hmAb-H11a Expression Vector

A DNA having the nucleotide sequence of hmAb-H11a shown in SEQ ID NO: 17 was synthesized. Using an In-Fusion HD PCR cloning kit, the synthesized DNA fragment was inserted into a site of pCMA-G1 constructed in Example 1)-2-1 that had been cleaved with the restriction enzyme BlpI, so as to construct a hmAb-H11a expression vector.

1)-2-2-5 Combination of Heavy Chain Expression Vector and Light Chain Expression Vector of Anti-CD37 Humanized Antibody An anti-CD37 humanized antibody having hmAb-H11 as a heavy chain and hmAb-L11 as a light chain was named hmAb-H11L11. An anti-CD37 humanized antibody having hmAb-H541 as a heavy chain and hmAb-L11 as a light chain was named hmAb-H541L11. An anti-CD37 humanized antibody having hmAb-H551 as a heavy chain and hmAb-L11 as a light chain was named hmAb-H551L11. An anti-CD37 humanized antibody having hmAb-H11a as a heavy chain and hmAb-L11 as a light chain was named hmAb-H11aL11.

1)-2-3 Production of Anti-CD37 Humanized Antibody

In accordance with the manual, FreeStyle 293F cells (manufactured by Thermo Fisher Scientific Inc.) were cultured and passaged. FreeStyle 293F cells in the logarithmic growth phase were adjusted to $2.0 \times 10^6$ cells/mL by dilution with FreeStyle 293 expression medium (manufactured by Thermo Fisher Scientific Inc.), and 600 mL of the dilution was seeded on a 3-L Fernbach Erlenmeyer Flask (manufactured by Corning Inc.). To 20 mL of Opti-Pro SFM medium (manufactured by Thermo Fisher Scientific Inc.), 1.8 mg of Polyethyleneimine (manufactured by Polysciences Inc.) was added. Next, to 20 mL of Opti-Pro SFM medium, 300 μg of the heavy chain expression vector and 300 μg of the light chain expression vector were added. To the Polyethyleneimine/Opti-Pro SFM mixed solution, the expression vector/Opti-Pro SFM mixed solution was added, and the obtained mixture was gently stirred, further left standing for 5 minutes, and then added to the FreeStyle 293F cells. The cells were shake-cultured at 95 rpm in an 8% $CO_2$ incubator at 37° C. for 4 hours, and thereafter, 600 mL of EX-CELL VPRO medium (manufactured by SAFC Biosciences Inc.), and 30 mL of 43.4 g/L BD Recharge CD (manufactured by BD Biosciences) were added to the culture. The cells were further shake-cultured at 95 rpm in an 8% $CO_2$ incubator at 37° C. for 6 days. The obtained culture supernatant was filtered through a bottle top filter having a pore size of 0.2 µm (manufactured by Thermo Fisher Scientific Inc.).

1)-2-4 Purification of Anti-CD37 Humanized Antibody

The antibody was purified from the culture supernatant obtained in Example 1)-2-3, by a two-step process, namely, by rProtein A affinity chromatography and ceramic hydroxyapatite. The culture supernatant was equilibrated with PBS and applied to a column that had been packed with Mab-SelectSuRe (manufactured by Cytiva Corp.), and thereafter, the column was washed with PBS in an amount of two or more times the volume of the column. Subsequently, the antibody was eluted using a 2 M arginine hydrochloride solution (pH 4.0). A fraction containing the antibody was dialyzed using Slide-A-Lyzer Dialysis Cassette (manufactured by Thermo Fisher Scientific Inc.), so that the buffer was replaced with PBS. The antibody solution was 5-fold diluted with a buffer of 5 mM sodium phosphate/50 mM MES/pH 7.0, and then applied to a ceramic hydroxyapatite column (manufactured by Bio-Rad Laboratories, Inc.) that had been equilibrated with a buffer of 5 mM NaPi/50 mM MES/30 mM NaCl/pH 7.0. Elution was carried out on a linear concentration gradient of sodium chloride, so that a fraction containing an antibody was collected. This fraction was dialyzed using Dialysis Cassettes, so that the buffer was replaced with HBSor (25 mM histidine/5% sorbitol, pH 6.0). The antibody was concentrated with VIVASPIN20 (molecular weight cutoff: UF10K, manufactured by Sartorius Stedim Biotech Inc.), thereby adjusting the IgG concentration to 20 to 25 mg/ml. Finally, the antibody was filtered through a Minisart Plus (manufactured by Sartorius Stedim Biotech Inc.) to obtain a purified sample.

Example 2: Production of Anti-CD37 Antibody-Drug Conjugate-1

2)-1 Production of Antibody-Drug Conjugate—(1) hmAb-H11L11-DXd hmAb-H11L11-DXd was synthesized by the following step.

[Formula 11]

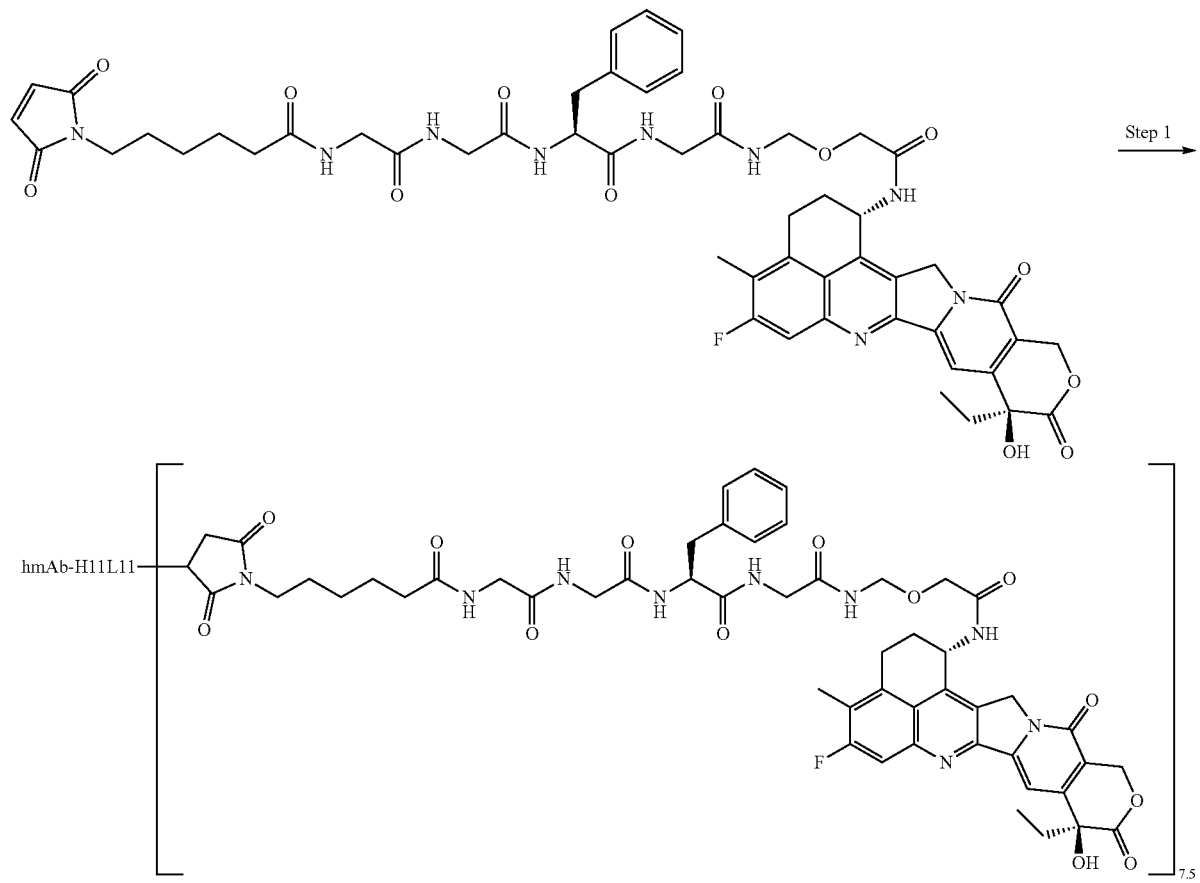

Reduction of antibody: hmAb-H11L11 prepared in Example 1)-2 was adjusted to 10.67 mg/mL with PBS6.0/EDTA by using common procedures B (using 1.50 mLmg$^{-1}$ cm$^{-1}$ as 280 nm absorption coefficient) and C described in production method 1. To this solution (0.5 mL), a 1 M aqueous dipotassium hydrogen phosphate solution (Nacalai Tesque, Inc.; 0.0075 mL) and an aqueous solution of 10 mM TCEP (Tokyo Chemical Industry Co., Ltd.) (0.022 mL; 6.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.0367 mL; 10.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0037 mL; 10.0 equivalents per antibody molecule) was added thereto, and the obtained mixture was stirred and then further left standing at room temperature for 20 minutes to terminate the reaction of the drug linker.

Purification: The above-described solution was purified by common procedure D described in production method 1 to obtain 3.5 mL of a solution containing the title antibody-drug conjugate "hmAb-H11L11-ADC".

Characterization: Using common procedures E and F (using $\varepsilon_{D,280}=5440$ and $\varepsilon_{D,370}=21800$) described in production method 1, the following characteristic values were obtained.

Antibody concentration: 1.30 mg/mL, antibody yield: 4.57 mg (86%), average number of conjugated drug molecules (n) per antibody molecule measured by common procedure E: 5.6, and average number of conjugated drug molecules (n) per antibody molecule measured by common procedure F: 7.5.

2)-2 Production of Antibody-Drug Conjugate—(2) hmAb-H11L11-DXd hmAb-H11L11-DXd was synthesized by the following step.

[Formula 12]

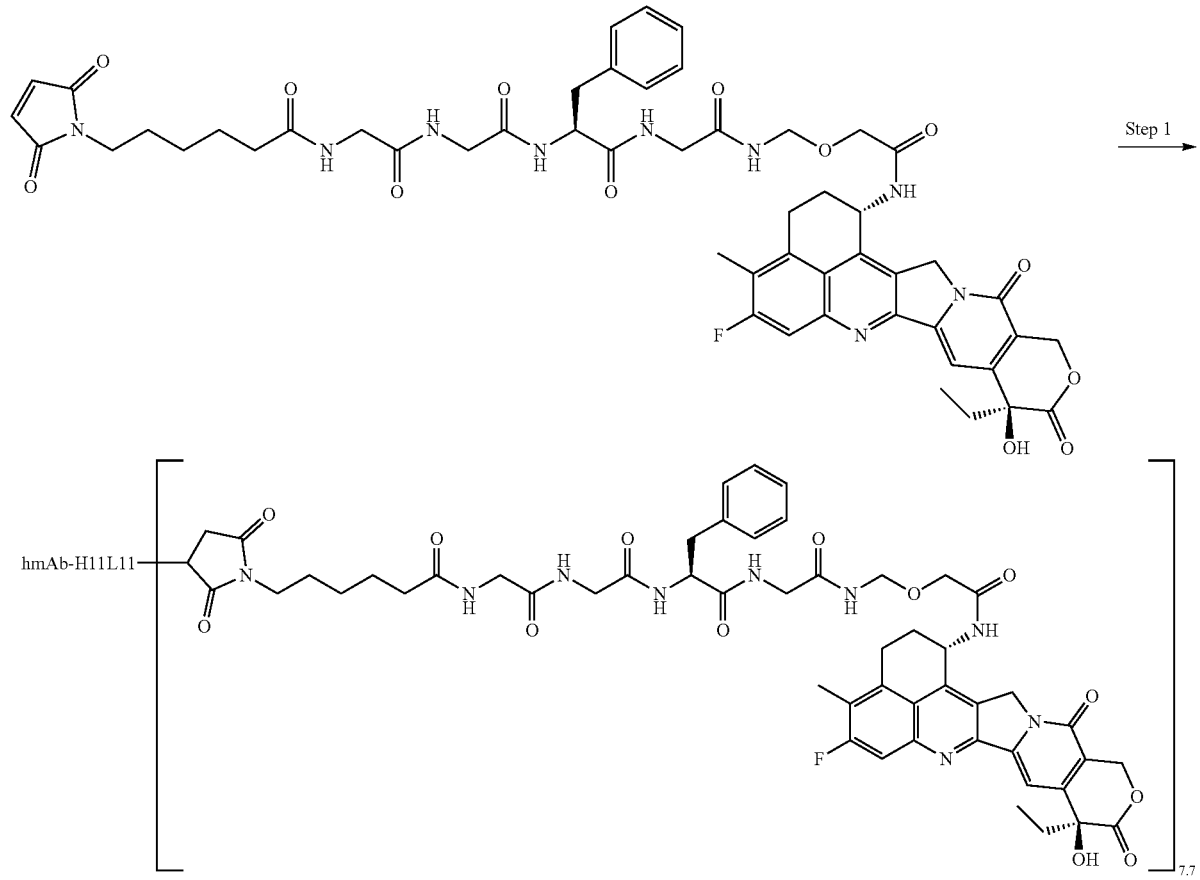

Reduction of antibody: hmAb-H11L11 prepared in Example 1)-2 was adjusted to 10.67 mg/mL with PBS6.0/EDTA by using common procedures B (using 1.50 mLmg$^{-1}$ cm$^{-1}$ as 280 nm absorption coefficient) and C described in production method 1. To this solution (0.5 mL), a 1 M aqueous dipotassium hydrogen phosphate solution (Nacalai Tesque, Inc.; 0.0075 mL) and an aqueous solution of 10 mM TCEP (Tokyo Chemical Industry Co., Ltd.) (0.0294 mL; 8.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.0441 mL; 12.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0044 mL; 12.0 equivalents per antibody molecule) was added thereto and stirred, and thereafter, the obtained mixture was further left standing at room temperature for 20 minutes to terminate the reaction of the drug linker.

Purification: The above-described solution was purified by common procedure D described in production method 1 to obtain 3.5 mL of a solution containing the title antibody-drug conjugate "hmAb-H11L11-ADC".

Characterization: Using common procedures E and F (using $\varepsilon_{D,280}$=5440 and $\varepsilon_{D,370}$=21800) described in production method 1, the following characteristic values were obtained.

Antibody concentration: 1.34 mg/mL, antibody yield: 4.69 mg (88%), average number of conjugated drug molecules (n) per antibody molecule measured by common procedure E: 5.9, and average number of conjugated drug molecules (n) per antibody molecule measured by common procedure F: 7.7.

2)-3 Production of Antibody-Drug Conjugate—(3) hmAb-H11L11-DXd hmAb-H11L11-DXd was synthesized by the following step.

Reduction of antibody: hmAb-H11L11 prepared in Example 1)-2 was adjusted to 10.67 mg/mL with PBS6.0/EDTA by using common procedures B (using 1.50 mLmg$^{-1}$ cm$^{-1}$ as 280 nm absorption coefficient) and C described in production method 1. To this solution (8.3 mL), a 1 M aqueous dipotassium hydrogen phosphate solution (Nacalai Tesque, Inc.; 0.124 mL) and an aqueous solution of 10 mM TCEP (Tokyo Chemical Industry Co., Ltd.) (0.486 mL; 8.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.728 mL; 12.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.073 mL; 12.0 equivalents per antibody molecule) was added thereto and

[Formula 13]

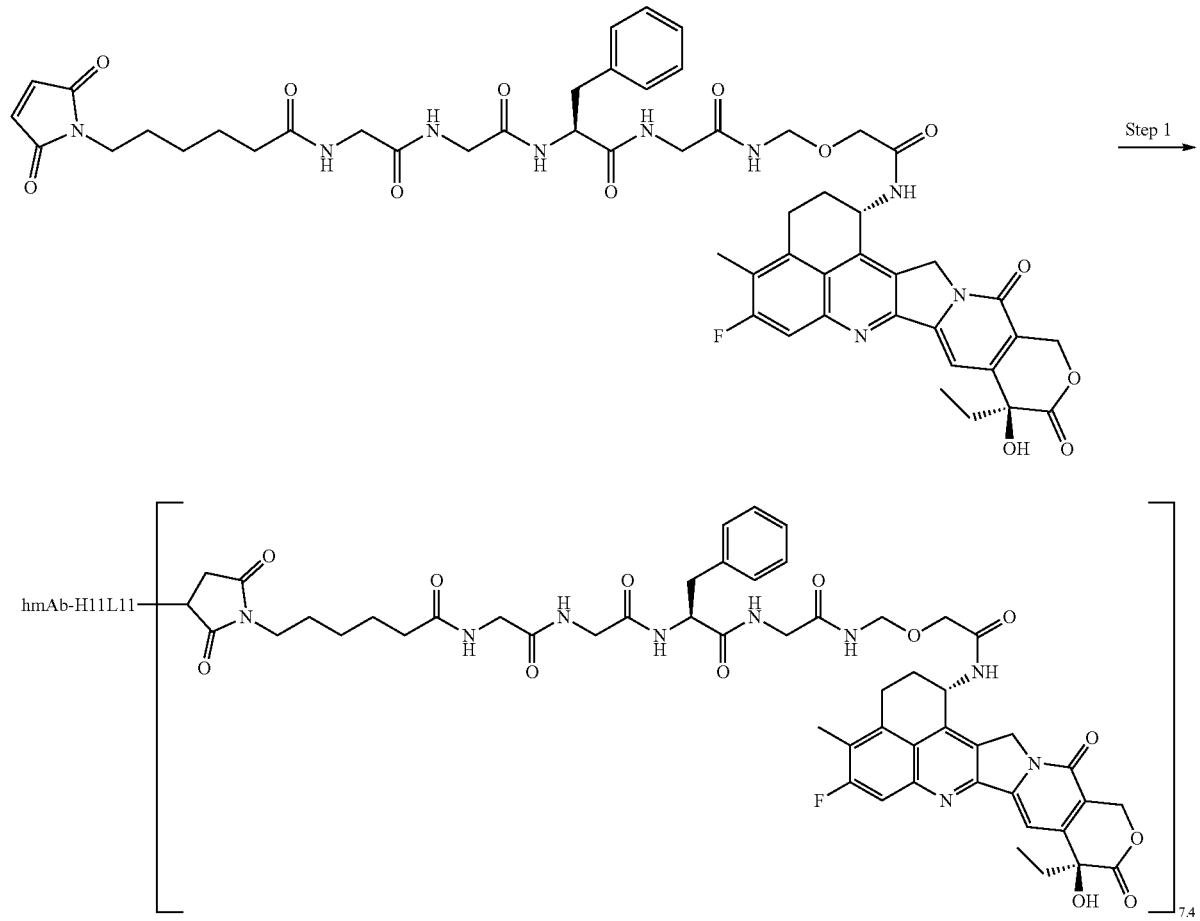

stirred, and thereafter, the obtained mixture was further left standing at room temperature for 20 minutes to terminate the reaction of the drug linker.

Purification: The above-described solution was purified by common procedure D described in production method 1 to obtain 31.5 mL of a solution containing the title antibody-drug conjugate "hmAb-H11L11-ADC".

Characterization: Using common procedures E and F (using $\varepsilon_{D,280}$=5440 and $\varepsilon_{D,370}$=21800) described in production method 1, the following characteristic values were obtained.

Antibody concentration: 2.23 mg/mL, antibody yield: 70.29 mg (80%), average number of conjugated drug molecules (n) per antibody molecule measured by common procedure E: 5.6, and average number of conjugated drug molecules (n) per antibody molecule measured by common procedure F: 7.4.

2)-4 Production of Antibody-Drug Conjugate—(4) hmAb-H541L11-DXd hmAb-H541L11-DXd was synthesized by the following step.

Reduction of antibody: hmAb-H541L11 prepared in Example 1)-2 was adjusted to 10.63 mg/mL with PBS6.0/EDTA by using common procedures B (using 1.50 mLmg$^{-1}$ cm$^{-1}$ as 280 nm absorption coefficient) and C described in production method 1. To this solution (8.9 mL), a 1 M aqueous dipotassium hydrogen phosphate solution (Nacalai Tesque, Inc.; 0.133 mL) and an aqueous solution of 10 mM TCEP (Tokyo Chemical Industry Co., Ltd.) (0.389 mL; 6.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.649 mL; 10.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.065 mL; 10.0 equivalents per antibody molecule) was added thereto stirred, and thereafter, the obtained mixture was further left standing at room temperature for 20 minutes to terminate the reaction of the drug linker.

[Formula 14]

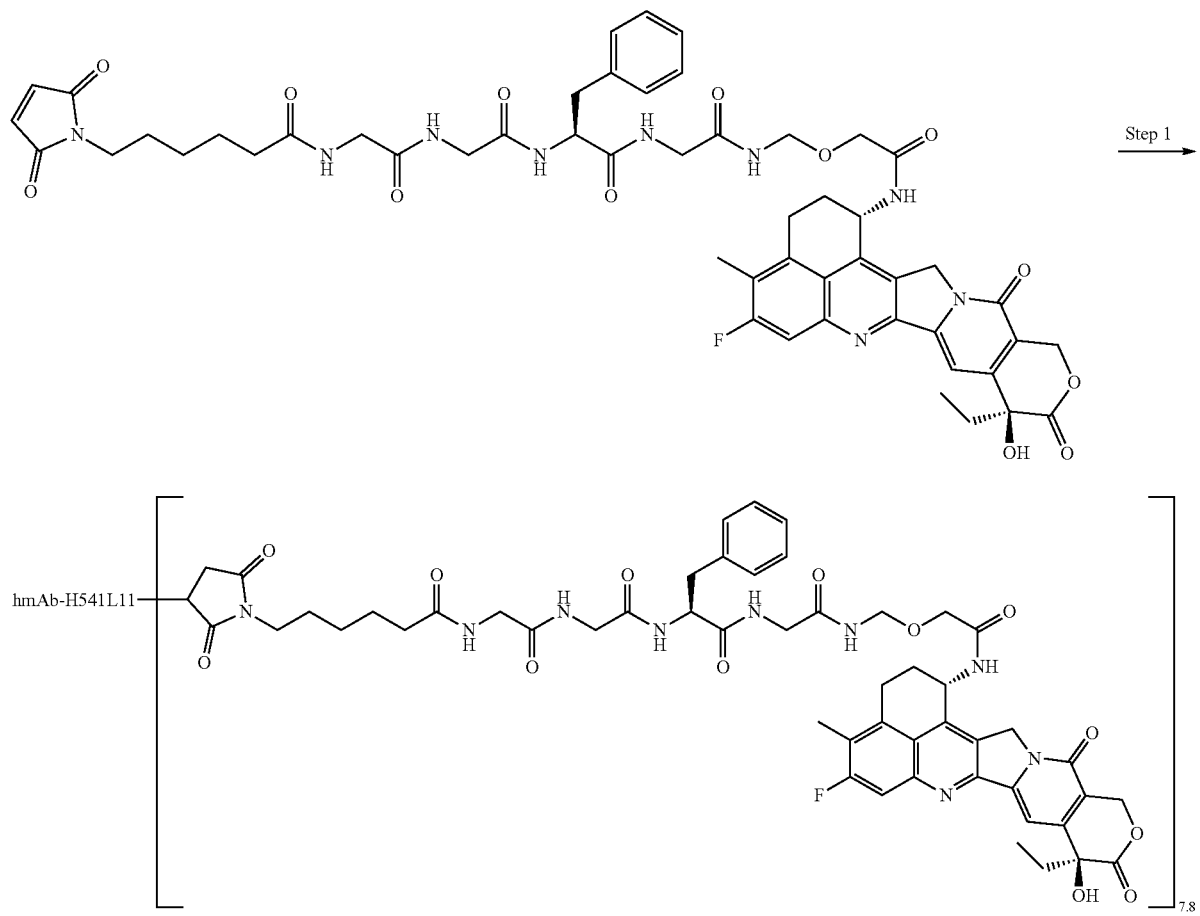

Purification: The above-described solution was purified by common procedure D described in production method 1 to obtain 31.5 mL of a solution containing the title antibody-drug conjugate "hmAb-H541L11-ADC".

Characterization: Using common procedures E and F ((using $\varepsilon_{D,280}$=5440 and $\varepsilon_{D,370}$=21800) described in production method 1, the following characteristic values were obtained.

Antibody concentration: 2.68 mg/mL, antibody yield: 84.26 mg (89%), average number of conjugated drug molecules (n) per antibody molecule measured by common procedure E: 5.9, and average number of conjugated drug molecules (n) per antibody molecule measured by common procedure F: 7.8.

2)-5 Production of Antibody-Drug Conjugate—(5) hmAb-H551L11-DXd hmAb-H551L11-DXd was synthesized by the following step.

Reduction of antibody: hmAb-H551L11 prepared in Example 1)-2 was adjusted to 10.62 mg/mL with PBS6.0/EDTA by using common procedures B (using 1.50 mLmg$^{-1}$ cm$^{-1}$ as 280 nm absorption coefficient) and C described in production method 1. To this solution (9.4 mL), a 1 M aqueous dipotassium hydrogen phosphate solution (Nacalai Tesque, Inc.; 0.141 mL) and an aqueous solution of 10 mM TCEP (Tokyo Chemical Industry Co., Ltd.) (0.411 mL; 6.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.686 mL; 10.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.069 mL; 10.0 equivalents per antibody molecule) was added thereto and stirred, and thereafter, the obtained mixture was further left standing at room temperature for 20 minutes to terminate the reaction of the drug linker.

Purification: The above-described solution was purified by common procedure D described in production method 1 to obtain 35.0 mL of a solution containing the title antibody-drug conjugate "hmAb-H551L11-ADC".

Characterization: Using common procedures E and F (using $\varepsilon_{D,280}$=5440 and $\varepsilon_{D,370}$=21800) described in production method 1, the following characteristic values were obtained.

Antibody concentration: 2.43 mg/mL, antibody yield: 85.08 mg (85%), average number of conjugated drug molecules (n) per antibody molecule measured by common

[Formula 15]

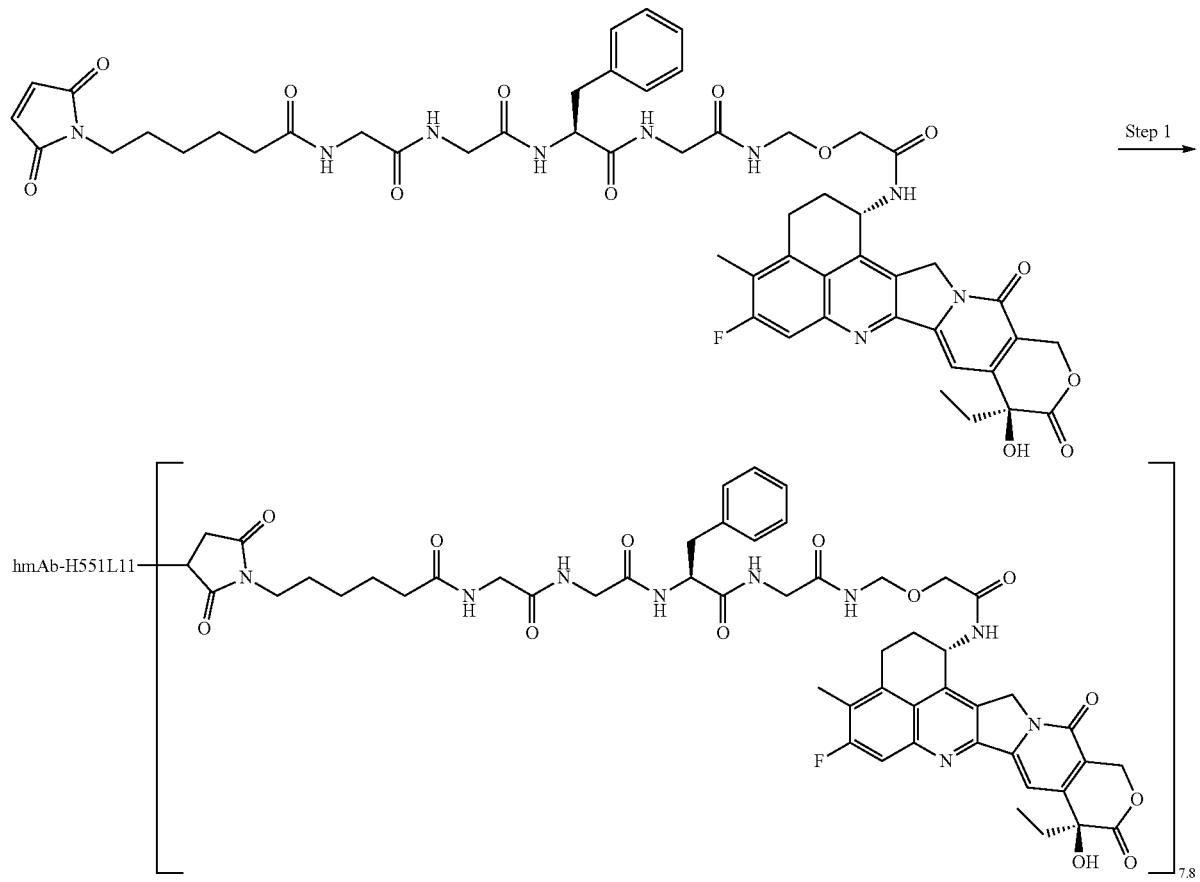

procedure E: 5.7, and average number of conjugated drug molecules (n) per antibody molecule measured by common procedure F: 7.8.

2)-6 Production of Antibody-Drug Conjugate—(6) hmAb-H11aL11-DXd hmAb-H11aL11-DXd was synthesized by the following step.

Reduction of antibody: hmAb-H11aL11 prepared in Example 1)-2 was adjusted to 10.59 mg/mL with PBS6.0/EDTA by using common procedures B (using 1.50 mLmg$^{-1}$ cm$^{-1}$ as 280 nm absorption coefficient) and C described in production method 1. To this solution (10.0 mL), a 1 M aqueous dipotassium hydrogen phosphate solution (Nacalai Tesque, Inc.; 0.150 mL) and an aqueous solution of 10 mM TCEP (Tokyo Chemical Industry Co., Ltd.) (0.510 mL; 7.0 equivalents per antibody molecule) were added. After confirming that the solution had a pH within 7.0±0.1, the interchain disulfide bond in the antibody was reduced by incubating the solution at 37° C. for 2 hours.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.801 mL; 11.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.080 mL; 11.0 equivalents per antibody molecule) was added thereto and

[Formula 16]

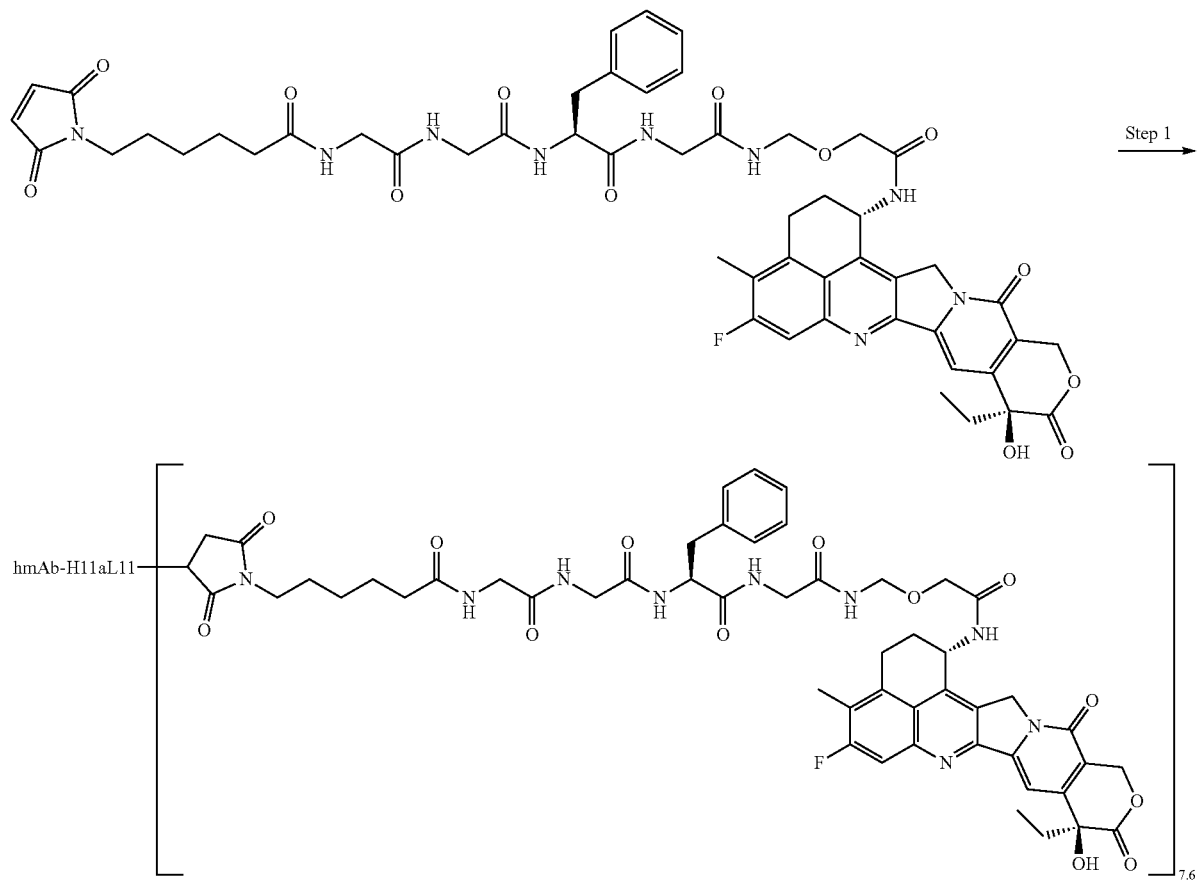

stirred, and thereafter, the obtained mixture was further left standing at room temperature for 20 minutes to terminate the reaction of the drug linker.

Purification: The above-described solution was purified by common procedure D described in production method 1 to obtain 35.0 mL of a solution containing the title antibody-drug conjugate "hmAb-H11aL11-ADC".

Characterization: Using common procedures E and F (using $\varepsilon_{D,280}$=5440 and $\varepsilon_{D,370}$=21800) described in production method 1, the following characteristic values were obtained.

Antibody concentration: 2.62 mg/mL, antibody yield: 91.57 mg (86%), average number of conjugated drug molecules (n) per antibody molecule measured by common procedure E: 5.7, and average number of conjugated drug molecules (n) per antibody molecule measured by common procedure F: 7.6.

In the production of hmAb-H11L11-DXd on the scale of 5 mg, the average number of conjugated drug molecules was 7.5 when 6.0 equivalents of an aqueous solution of 10 mM TCEP were used per antibody molecule. Accordingly, as a result of increasing the amount of the aqueous solution of 10 mM TCEP to 8.0 equivalents per antibody molecule, the average number of conjugated drug molecules was improved to 7.7. Nonetheless, in the production on the scale of 100 mg, the average number of conjugated drug molecules was 7.4 even when 8.0 equivalents of the aqueous solution of 10 mM TCEP were used per antibody molecule. The production on the scale of 100 mg presumably requires a larger amount of the aqueous solution of 10 mM TCEP for elevating the average number of conjugated drug molecules in hmAb-H11L11-DXd. By contrast, in the production of the other conjugates hmAb-H541L11-DXd, hmAb-H551L11-DXd, and hmAb-H11aL11-DXd on the scale of 100 mg, the average number of conjugated drug molecules reached 7.6 to 7.8 using 6.0 to 7.0 equivalents of the aqueous solution of 10 mM TCEP per antibody molecule.

Example 3: Evaluation of Recovery Rate of Anti-CD37 Humanized Antibody-Drug Conjugate into Physiological Saline Each anti-CD37 humanized antibody-drug conjugate dissolved at 20 mg/mL in ABSor (manufactured by Nacalai Tesque, Inc.) was diluted into 2 mg/mL with Otsuka physiological saline (manufactured by Otsuka Pharmaceutical Factory, Inc.) and left standing at room temperature or 4° C. for 5 hours. 10 μL of this supernatant was injected to YMC-Pack Diol-300 SEC, 30 nm, S-2 μm, 300×4.6 mm (manufactured by YMC Co., Ltd.) using Prominence (manufactured by Shimadzu Corp.), and analyzed by size exclusion chromatography using 3×PBS and 8% isopropanol (a solution of three PBS tablets (manufactured by Takara Bio Inc.) dissolved in 920 mL of ultrapure water and supplemented with 80 mL isopropanol) as a mobile phase. The recovery rate of the anti-CD37 humanized antibody-drug conjugate was calculated according to the following expression.

Recovery rate (%)=(Recovery rate of the sample left standing at 4° C./Recovery rate of the sample left standing at room temperature)×100

As shown in Table 1, the antibody-drug conjugate comprising the antibody, the amino acid sequence of which had been designed in Example 1)-1-5 for the purpose of improving the physical properties of the anti-CD37 humanized antibody-drug conjugate, had a better recovery rate in physiological saline at 4° C. than that of the antibody-drug conjugate comprising the antibody, the amino acid sequence of which had been designed in Example 1)-1-4. From the better recovery rate in physiological saline at 4° C., it was demonstrated that the aforementioned anti-CD37 humanized antibody-drug conjugate could be handled in physiological saline. On the other hand, hmAb-H11L11-DXd was found difficult to handle in physiological saline. In this case, although use of a glucose solution may be discussed, the solution is known to be responsible for the glycation of antibodies (MAbs, v.9 (4), 586-594, (2017)) and might lead to reduced medicinal effects of antibody-drug conjugates.

Furthermore, some antibody drugs have been reported to undergo protein aggregation by mixing with the glucose solution. Thus, options of diluents are desirable. Moreover, use of the glucose solution requires careful administration to patients with diabetes mellitus, diabetes insipidus, or renal failure due to the risk of loss of electrolytes. hmAb-H11L11 was judged and selected as a highly reasonable humanized antibody because the human consensus sequence having the highest homology to the anti-CD37 mouse monoclonal antibody HH1 was used as an acceptor for humanization and this antibody maintained its antigen-binding activity. However, it was considered for the above-described reasons that the antibody needed to be modified. Thus, the amino acid sequences shown in Example 1)-1-5 were designed.

TABLE 1

| Name | Recovery rate (%) |
|---|---|
| hmAb-H11L11-DXd | 79.7 |
| hmAb-H541L11-DXd | 98.6 |
| hmAb-H551L11-DXd | 96.6 |
| hmAb-H11aL11-DXd | 100 |

Example 4: In Vitro Activity Evaluation of Antibody-Drug Conjugate

4)-1 Evaluation of Binding Activity of Humanized Anti-CD37 Antibody-Drug Conjugate The binding activity of the four antibody-drug conjugates (clone names: hmAb-H11L11-DXd, hmAb-H541L11-DXd, hmAb-H551L11-DXd, and hmAb-H11aL11-DXd) produced in Example 2 was evaluated by flow cytometry. CD37-positive human diffuse large B-cell lymphoma cell line OCI-LY7 (DSMZ) cultured in IMDM medium supplemented with 20% FBS under conditions of 37° C. and 5% $CO_2$ were recovered and centrifuged. After removal of the supernatant, the cells were suspended by the addition of each of the four antibody-drug conjugates or a negative control antibody-drug conjugate (hmAb-IgG1-DXd) produced using human IgG at each concentration. The cells were left standing at 4° C. for 1 hour. The cells were washed twice with PBS supplemented with 5% FBS, and then suspended by the addition of FLUORESCEIN (FITC)-AffiniPure F(ab')2 Fragment Goat Anti-Human IgG, Fcγ Fragment Specific (Jackson ImmunoResearch Laboratories, Inc.) that had been 100-fold diluted with PBS supplemented with 5% FBS. The cells were left standing at 4° C. for 30 minutes. The cells were washed twice with PBS supplemented with 5% FBS, followed by detection using a flow cytometer (BD LSRFortessa TM X-20, BD Biosciences). The data was analyzed using FlowJo (Tree Star, Inc.). The results are shown in FIG. 6. In FIG. 6, the abscissa depicts antibody concentration (μg/ml), and the ordinate depicts the amount of the antibody bound by MFI (mean fluorescence intensity). As shown in FIG. 6, concentration-dependent increase in the amount of the antibody bound in the CD37-positive human diffuse large B-cell lymphoma cell line OCI-LY7 was observed for the humanized anti-CD37 antibodies and the antibody-drug conjugates.

4)-2 Evaluation of Cell Growth Inhibition Activity of Humanized Anti-CD37 Antibody-Drug Conjugate CD37-positive human diffuse large B-cell lymphoma cell line OCI-LY7 (DSMZ) was seeded over a 96-well plate at $5\times10^2$ cells/100 µL/well in IMDM medium supplemented with 20% FBS, and each of the 4 antibody-drug conjugates (clone names: hmAb-H11L11-DXd, hmAb-H541L11-DXd, hmAb-H551L11-DXd, and hmAb-H11aL11-DXd) produced in Example 2 were added to the cells such that the final concentrations were from 0.0064 nM to 20 nM. The cells were cultured under conditions of 37° C. and 5% $CO_2$ for 6 days, and thereafter, the number of live cells was measured by the quantification of ATP using CellTiter-Glo™ Luminescent Cell Viability Assay (Promega Corp.). A cell survival rate was quantified with the number of live cells in a vehicle group defined as 100%. FIG. 7 shows concentration-dependent cell growth inhibition activity when each antibody-drug conjugate was added to the cells. hmAb-IgG-DXd in the experiment was an antibody-drug conjugate prepared from human IgG1 which recognized an antigen unrelated to CD37, and was used as a negative control.

Example 5: In Vivo Antitumor Effect of Antibody-Drug Conjugate-1

The antitumor effects of the antibody-drug conjugates were evaluated using animal models derived from immunodeficient mice by the inoculation of CD37-positive human tumor cell line cells. Five-week-old SCID mice (CB17/Icr-Prkdc[scid]/CrlCrlj, Charles River Laboratories Japan Inc.) were acclimatized for 3 days or longer under SPF conditions before use in the experiment. The mice were fed with a sterilized solid diet (FR-2, Funabashi Farms Co., Ltd) and given sterilized tap water (which had been prepared by adding a 5 to 15 ppm sodium hypochlorite solution to tap water). The long diameter and short diameter of the inoculated tumor were measured twice a week using electronic digital calipers ($C_D$-15CX, Mitutoyo Corp.), and the volume of the tumor was then calculated according to the following expression.

Tumor volume (mm³)=½×Long diameter (mm)× [Short diameter (mm)]²

Each antibody-drug conjugate was diluted with ABS buffer (10 mM acetate buffer, 5% sorbitol, pH 5.5) (Nacalai Tesque, Inc.), and the dilution was intravenously administered at a dose shown in each Example to the tail of each mouse. ABS buffer was administered in the same manner as above to a control group (vehicle group). Six mice per group were used in the experiment.

5)-1 Antitumor Effect—(1)

CD37-positive human diffuse large B-cell lymphoma cell line OCI-LY7 (DSMZ) was suspended in 50% Matrigel (Corning Inc., diluted with physiological saline), and the cell suspension was subcutaneously inoculated at a dose of $1\times10^7$ cells to the right flank region of each female SCID mouse (Day 0). On Day 9, the mice were randomly grouped. On the day of grouping, each of the 4 antibody-drug conjugates (clone names: hmAb-H11L11-DXd, hmAb-H541L11-DXd, hmAb-H551L11-DXd, and hmAb-H11aL11-DXd) produced in Example 2 was intravenously administered at a dose of 1 mg/kg or 3 mg/kg to the tail of each mouse. An antibody-drug conjugate (hmAb-IgG1-DXd) produced using human IgG was administered as a negative control at a dose of 3 mg/kg in the same manner as above. The results are shown in FIG. 8. The abscissa depicts the number of days, and the ordinate depicts tumor volume. The error range depicts a SE value.

All the 4 antibody-drug conjugates produced in Example 2 significantly decreased tumor volume in a dose-dependent manner, and completely inhibited tumor growth at the dose of 3 mg/kg.

5)-2 Antitumor Effect—(2)

In the same manner as in Example 5)-1, CD37-positive human diffuse large B-cell lymphoma cell line WSU-DLCL2 (DSMZ) was subcutaneously inoculated at a dose of $1\times10^7$ cells to the right flank region of each female SCID mouse (Day 0). On Day 11, the mice were randomly grouped. On the day of grouping, each of the 4 antibody-drug conjugates produced in Example 2, or hmAb-IgG1-DXd (negative control) was intravenously administered at a dose of 1 mg/kg or 3 mg/kg to the tail of each mouse. The results are shown in FIG. 9. The abscissa depicts the number of days, and the ordinate depicts tumor volume. The error range depicts a SE value.

All the 4 antibody-drug conjugates produced in Example 2 significantly decreased tumor volume in a dose-dependent manner, and exhibited a tumor regression effect at the dose of 3 mg/kg.

5)-3 Antitumor Effect—(3)

In the same manner as in Example 5)-1, CD37-positive human diffuse large B-cell lymphoma cell line SU-DHL-8 (ATCC) was subcutaneously inoculated at a dose of $5\times10^6$ cells to the right flank region of each female SCID mouse (Day 0). On Day 7, the mice were randomly grouped. On the day of grouping, each of the 4 antibody-drug conjugates produced in Example 2, or hmAb-IgG1-DXd (negative control) was intravenously administered at a dose of 1 mg/kg or 3 mg/kg to the tail of each mouse. The results are shown in FIG. 10. The abscissa depicts the number of days, and the ordinate depicts tumor volume. The error range depicts a SE value.

All the 4 antibody-drug conjugates produced in Example 2 significantly decreased tumor volume in a dose-dependent manner, and completely inhibited tumor growth at the dose of 3 mg/kg.

Example 6: Production of Anti-CD37 Antibody-Drug Conjugate-2

IMGN529 was synthesized by the following step.

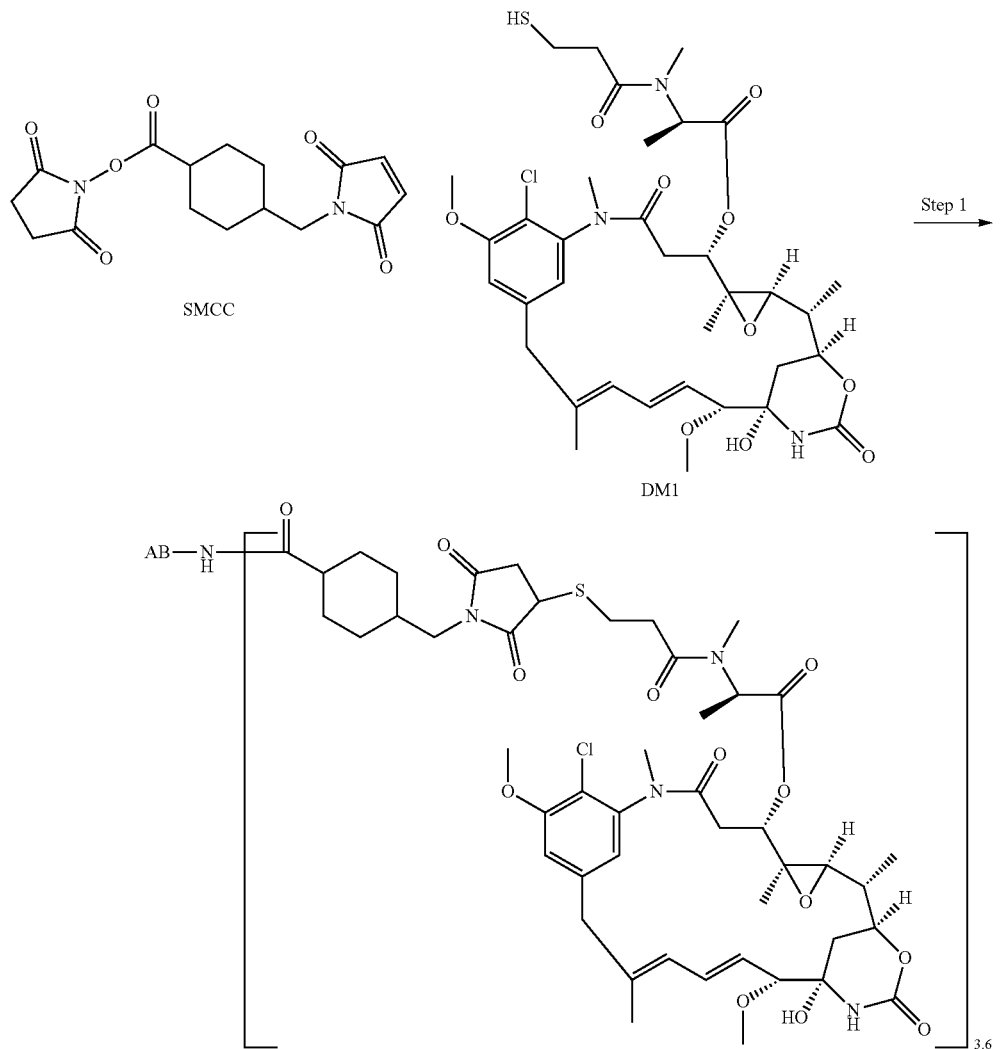

[Formula 17]

Preparation of antibody: Naratuximab (anti-CD37 antibody, IMGT/2D structure-DB card for INN 10239) was adjusted to 12.12 mg/mL with PBS6.0/EDTA by using common procedures B (using 1.531 mLmg$^{-1}$ cm$^{-1}$ as 280 nm absorption coefficient) and C described in production method 1.

Conjugation between antibody and drug linker: To 0.4 mL of the above-described antibody solution, a 10 mM solution of succinimidyl 4-(N-maleimidomethyl) cyclohexane-1-carboxylate (SMCC) in N, N-dimethylacetamide (0.0338 mL; 10.0 equivalents per antibody molecule) and a 10 mM solution of a maytansine derivative (DM1) in N, N-dimethylacetamide (0.0507 mL; 15.0 equivalents per antibody molecule) were added, and the mixture was stirred and then rotated at room temperature for 16 hours.

Purification: The above-described solution was purified by common procedure D described in production method 1 to obtain 2.5 mL of a solution containing the title antibody-drug conjugate "IMGN529".

This reaction on the scale of 0.4 mL was repeated six times, and the resulting solutions were combined.

Characterization: Using common procedure E (using $\varepsilon_{D,280}$=5700 and $\varepsilon_{D,252}$=26790) described in production method 1, the following characteristic values were obtained.

Antibody concentration: 1.29 mg/mL, antibody yield: 15.61 mg (54%), and average number of conjugated drug molecules (n) per antibody molecule measured by common procedure E: 3.6.

Example 7: In Vivo Antitumor Effect of Antibody-Drug Conjugate-2

The antitumor effects of the antibody-drug conjugates were evaluated using animal models derived from immunodeficient mice by the inoculation of CD37-positive human tumor cell line cells. 4- to 6-week-old SCID mice (CB17/Icr-Prkdc[scid]/CrlCrlj: Charles River Laboratories Japan Inc., and CB17/IcrJcl-Prkdc[scid]: CLEA Japan, Inc.) were acclimatized for 3 days or longer under SPF conditions before use in the experiment. The mice were fed with a sterilized solid diet (FR-2, Funabashi Farms Co., Ltd) and given sterilized tap water (which had been prepared by adding a 5 to 15 ppm sodium hypochlorite solution to tap water). The long diameter and short diameter of the inoculated tumor were measured twice a week using electronic digital calipers (CD-15CX, Mitutoyo Corp.), and the volume of the tumor was then calculated according to the following expression.

Tumor volume (mm$^3$)=½×Long diameter (mm)× [Short diameter (mm)]$^2$

Each antibody-drug conjugate was diluted with ABS buffer (10 mM acetate buffer, 5% sorbitol, pH 5.5) (Nacalai Tesque, Inc.), and the dilution was intravenously administered at a dose shown in each Example to the tail of each mouse. ABS buffer was administered in the same manner as above to a control group (vehicle group). For control groups, POLIVY (manufactured by Genentech Inc.), IMGN529, or RITUXAN (manufactured by Zenyaku Kogyo Co., Ltd.) was intravenously administered to the tail of each mouse; ibrutinib (synthesized by a method well known to those skilled in the art) or venetoclax (synthesized by a method well known to those skilled in the art) was orally administered once a day; and TREAKISYM (manufactured by SymBio Pharmaceuticals Ltd.) was intraperitoneally administered once a day for 2 days. Five or six mice per group were used in the experiment.

7)-1 Antitumor Effect—(1)

CD37-positive human diffuse large B-cell lymphoma cell line OCI-LY7 (DSMZ) was suspended in 50% Matrigel (Corning Inc., diluted with physiological saline), and the cell suspension was subcutaneously inoculated at a dose of 1×10$^7$ cells to the right flank region of each female SCID mouse (Day 0). On Day 10, the mice were randomly grouped. On the day of grouping, each antibody-drug conjugate was intravenously administered to the tail of each mouse. The results are shown in FIG. 11. The abscissa depicts the number of days, and the ordinate depicts tumor volume. The error range depicts a SE value.

No tumor regression was found in the groups given POLIVY, IMGN529, or hmAb-IgG1-DXd (negative control). By contrast, in the group given hmAb-H541L11-DXd produced in Example 2)-4, the administration at a dose of 1 mg/kg significantly inhibited tumor growth, and the administration at a dose of 3 mg/kg resulted in complete tumor regression.

7)-2 Antitumor Effect—(2)

In the same manner as in Example 7)-1, CD37-positive human diffuse large B-cell lymphoma cell line SU-DHL-8 (ATCC) was subcutaneously inoculated at a dose of 1×10$^7$ cells to the right flank region of each female SCID mouse (Day 0). On Day 8, the mice were randomly grouped. On the day of grouping, each antibody-drug conjugate was intravenously administered to the tail of each mouse. The results are shown in FIG. 12. The abscissa depicts the number of days, and the ordinate depicts tumor volume. The error range depicts a SE value.

No tumor regression was found in the groups given POLIVY, IMGN529, or hmAb-IgG1-DXd (negative control). By contrast, in the group given hmAb-H541L11-DXd produced in Example 2)-4, the administration at a dose of 3 mg/kg resulted in complete tumor regression.

7)-3 Antitumor Effect—(3)

In the same manner as in Example 7)-1, CD37-positive human diffuse large B-cell lymphoma cell line NU-DUL-1 (DSMZ) was subcutaneously inoculated at a dose of 1×10$^7$ cells to the right flank region of each female SCID mouse (Day 0). On Day 14, the mice were randomly grouped. On the day of grouping, each antibody-drug conjugate was intravenously administered to the tail of each mouse. The results are shown in FIG. 13. The abscissa depicts the number of days, and the ordinate depicts tumor volume. The error range depicts a SE value.

No tumor regression was found or tumor regrowth after regression was found in the groups given POLIVY, IMGN529, or hmAb-IgG1-DXd (negative control). By contrast, in the group given hmAb-H541L11-DXd produced in Example 2)-4, the administration at a dose of 1 mg/kg significantly inhibited tumor growth, and the administration at a dose of 3 mg/kg resulted in complete tumor regression.

7)-4 Antitumor Effect—(4)

In the same manner as in Example 7)-1, CD37-positive human diffuse large B-cell lymphoma cell line SU-DHL-4 (DSMZ) was subcutaneously inoculated at a dose of 1×10$^7$ cells to the right flank region of each female SCID mouse (Day 0). On Day 16, the mice were randomly grouped. On the day of grouping, each antibody-drug conjugate was intravenously administered to the tail of each mouse. The results are shown in FIG. 14. The abscissa depicts the number of days, and the ordinate depicts tumor volume. The error range depicts a SE value.

The group given 3 mg/kg of hmAb-H541L11-DXd produced in Example 2)-4 exhibited an antitumor effect equivalent to or higher than that in the group given 10 mg/kg of IMGN529.

7)-5 Antitumor Effect—(5)

In the same manner as in Example 7)-1, CD37-positive human chronic lymphocytic leukemia cell line JVM-3 (DSMZ) was subcutaneously inoculated at a dose of 3×10$^6$ cells to the right flank region of each female SCID mouse (Day 0). On Day 13, the mice were randomly grouped. On the day of grouping, each antibody-drug conjugate was intravenously administered to the tail of each mouse. RITUXAN was intravenously administered to the tail of each mouse; ibrutinib or venetoclax was orally administered once a day; and TREAKISYM was intraperitoneally administered once a day for 2 days. The results are shown in FIG. 15. The abscissa depicts the number of days, and the ordinate depicts tumor volume. The error range depicts a SE value.

No tumor regression was found in the groups given the control drug. By contrast, in the group given hmAb-H541L11-DXd produced in Example 2)-4, the administration at a dose of 1 mg/kg significantly inhibited tumor growth, and the administration at a dose of 3 mg/kg resulted in complete tumor regression.

7)-6 Antitumor Effect—(6)

In the same manner as in Example 7)-1, CD37-positive human follicular lymphoma cell line DOHH-2 (DSMZ) was subcutaneously inoculated at a dose of 1×10$^6$ cells to the right flank region of each female SCID mouse (Day 0). On Day 21, the mice were randomly grouped. On the day of grouping, hmAb-H541L11-DXd was intravenously administered to the tail of each mouse. The results are shown in FIG. 16. The abscissa depicts the number of days, and the ordinate depicts tumor volume. The error range depicts a SE value.

No tumor regression was found in the groups given IMGN529 or hmAb-IgG1-DXd (negative control). By contrast, in the group given hmAb-H541L11-DXd produced in Example 2)-4, the administration at a dose of 1 mg/kg resulted in tumor regression, and the administration at a dose of 3 mg/kg resulted in complete tumor regression, as in the group given POLIVY.

INDUSTRIAL APPLICABILITY

The present invention provides an anti-CD37 antibody having internalization activity and an antibody-drug conjugate comprising the antibody. The antibody-drug conjugate can be used, for example, as a therapeutic drug for malignant B-cell lymphoma and the like.

Sequence Listing Free Text

SEQ ID NO: 1: Nucleotide sequence encoding a hmAb-L11 light chain
SEQ ID NO: 2: Amino acid sequence of the hmAb-L11 light chain
SEQ ID NO: 3: Nucleotide sequence encoding a hmAb-H11 heavy chain
SEQ ID NO: 4: Amino acid sequence of the hmAb-H11 heavy chain
SEQ ID NO: 5: Nucleotide sequence encoding a hmAb-H541 heavy chain
SEQ ID NO: 6: Amino acid sequence of the hmAb-H541 heavy chain
SEQ ID NO: 7: Nucleotide sequence encoding a hmAb-H551 heavy chain
SEQ ID NO: 8: Amino acid sequence of the hmAb-H551 heavy chain
SEQ ID NO: 9: Nucleotide sequence encoding a hmAb-H11a heavy chain
SEQ ID NO: 10: Amino acid sequence of the hmAb-H11a heavy chain
SEQ ID NO: 11: Nucleotide fragment comprising a nucleotide sequence encoding a light chain signal sequence and a human κ light chain constant region
SEQ ID NO: 12: Nucleotide sequence encoding the variable region of the hmAb-L11 light chain
SEQ ID NO: 13: Nucleotide fragment comprising a nucleotide sequence encoding a heavy chain signal sequence and a human G1 heavy chain constant region
SEQ ID NO: 14: Nucleotide sequence encoding the variable region of the hmAb-H11 heavy chain
SEQ ID NO: 15: Nucleotide sequence encoding the variable region of the hmAb-H541 heavy chain
SEQ ID NO: 16: Nucleotide sequence encoding the variable region of the hmAb-H551 heavy chain
SEQ ID NO: 17: Nucleotide sequence encoding the variable region of the hmAb-H11a heavy chain
SEQ ID NO: 18: Amino acid sequence of human CD37
SEQ ID NO: 19: CDRL1 sequence of a humanized anti-CD37 antibody
SEQ ID NO: 20: CDRL2 sequence of the humanized anti-CD37 antibody
SEQ ID NO: 21: CDRL3 sequence of the humanized anti-CD37 antibody
SEQ ID NO: 22: CDRH1 sequence of the humanized anti-CD37 antibody
SEQ ID NO: 23: CDRH2 sequence of the humanized anti-CD37 antibody
SEQ ID NO: 24: CDRH3 sequence of the humanized anti-CD37 antibody

---

The invention claimed is:

1. An antibody-drug conjugate wherein an anti-CD37 antibody is conjugated to a drug-linker structure represented by any one formula selected from the group consisting of the following formulas (a) to (f):

-(Succinimid-3-yl-N)—CH$_2$CH$_2$—C(=O)-GGFG-NH—CH$_2$CH$_2$CH$_2$—C(=O)—(NH-DX),  (a)

-(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX),  (b)

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX),  (c)

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX),  (d)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX), and  (e)

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX),  (f)

wherein
-(Succinimid-3-yl-N)— has a structure represented by the following formula:

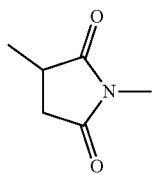

[Formula 1]

which is connected to the antibody at position 3 thereof and is connected to a methylene group in the linker structure containing this structure on the nitrogen atom at position 1, GGFG represents an amino acid sequence consisting of glycine-glycine-phenylalanine-glycine linked through peptide bonds, —(NH-DX) is a group represented by the following formula:

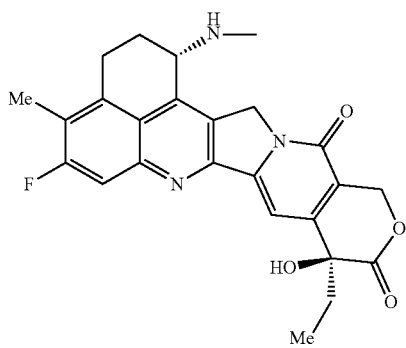

[Formula 2]

with the nitrogen atom of the amino group at position 1 as a connecting position, and the anti-CD37 antibody comprises
- a light chain variable region comprising the amino acid sequence at positions 21 to 128 in the light chain full-length amino acid sequence shown in SEQ ID NO: 2 and
- a heavy chain variable region comprising the CDRH1 consisting of SEQ ID NO: 22; the CDRH2 consisting of SEQ ID NO: 23; and the CDRH3 consisting of SEQ ID NO: 24.

2. The antibody-drug conjugate according to claim 1, wherein the anti-CD37 antibody is an antibody comprising a heavy chain variable region and a light chain variable region in any one combination selected from the group consisting of the following combinations (g) to (j):

(g) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 4;

(h) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6;

(i) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8; and (j) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

3. The antibody-drug conjugate according to claim 1, wherein the anti-CD37 antibody is an antibody comprising a heavy chain variable region and a light chain variable region in any one combination selected from the group consisting of the following combinations (h) to (j):

(h) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6;

(i) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8; and (j) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

4. The antibody-drug conjugate according to claim 1, wherein the anti-CD37 antibody is an antibody comprising a heavy chain and a light chain in any one combination selected from the group consisting of the following combinations (k) to (n):

(k) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 4;

(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;

(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and (n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

5. The antibody-drug conjugate according to claim 1, wherein the anti-CD37 antibody is an antibody comprising a heavy chain and a light chain in any one combination selected from the group consisting of the following combinations (l) to (n):

(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;

(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and (n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

6. The antibody-drug conjugate according to claim 1, wherein the drug-linker structure is represented by any one formula selected from the group consisting of the following formulas (c), (d), and (e):

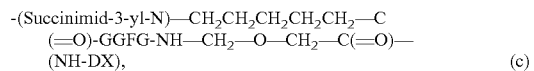

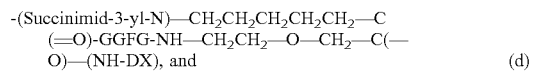

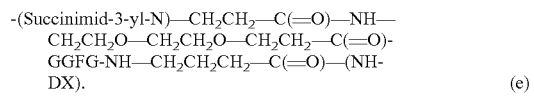

7. The antibody-drug conjugate according to claim 1, wherein the
drug-linker structure is represented by the following formula (c) or (e):

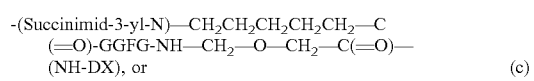

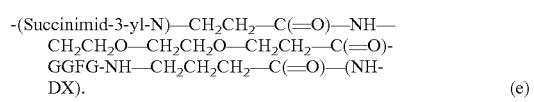

8. The antibody-drug conjugate according to claim 1, which is represented by the following formula (wherein A represents a connecting position to the antibody):

[Formula 3]

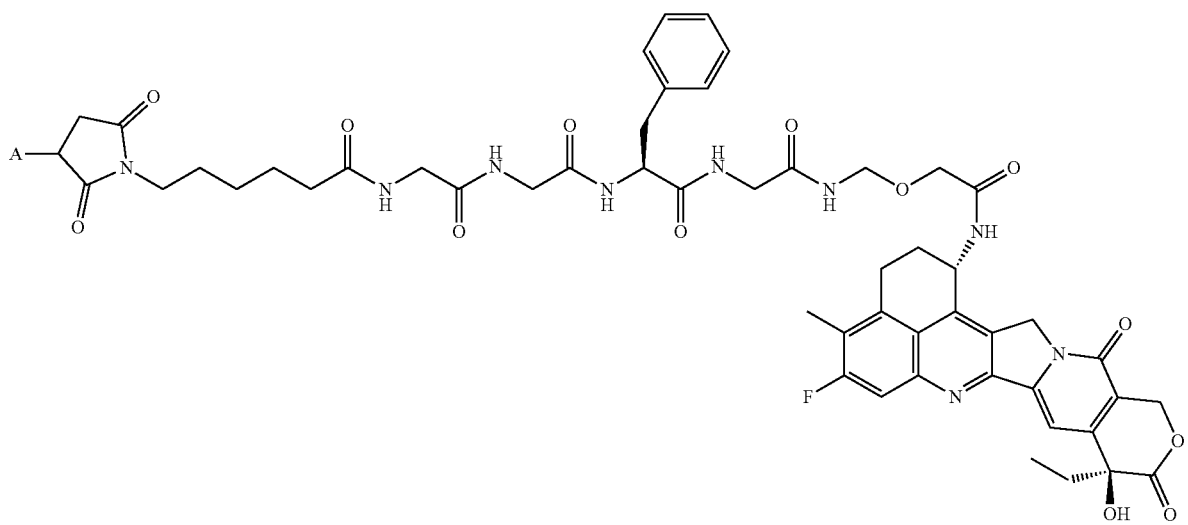

wherein the antibody is conjugated to the drug-linker by a thioether bond.

9. The antibody-drug conjugate according to claim 1, which is represented by the following formula:

[Formula 4]

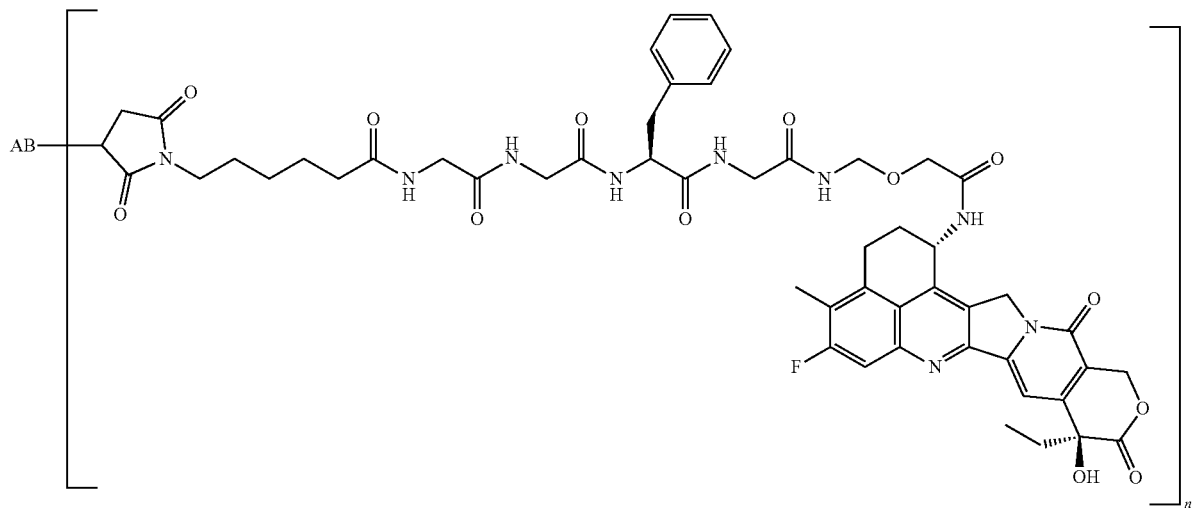

wherein AB represents the antibody, n represents the average number of units of the drug-linker structure conjugated to the antibody per antibody, and the antibody is connected to the drug-linker via a sulfhydryl group derived from the antibody.

10. The antibody-drug conjugate according to claim 1, wherein the antibody heavy chain has undergone one or two or more modifications selected from the group consisting of N-linked glycosylation, O-linked glycosylation, amino-terminal processing, carboxylterminal processing, deamidation, isomerization of aspartic acid, oxidation of methionine, oxidation of tryptophan, addition of a methionine residue to the amino terminus, amidation of a proline residue, and a deletion of one or two amino acids from the carboxyl terminus.

11. The antibody-drug conjugate according to claim 10, wherein one or two amino acids are deleted from the carboxyl terminus of the antibody heavy chain.

12. The antibody-drug conjugate according to claim 10, wherein one amino acid is deleted from each of the carboxyl termini of both of the antibody heavy chains.

13. The antibody-drug conjugate according to claim 10, wherein a proline residue at the carboxyl terminus of the antibody heavy chain is further amidated.

14. The antibody-drug conjugate according to claim 1, wherein the average number of units of the drug-linker structure conjugated per antibody is in the range of from 1 to 10.

15. The antibody-drug conjugate according to claim 1, wherein the average number of units of the drug-linker structure conjugated per antibody is in the range of from 2 to 8.

16. The antibody-drug conjugate according to claim 1, wherein the average number of units of the drug-linker structure conjugated per antibody is in the range of from 3 to 8.

17. The antibody-drug conjugate according to claim 1, wherein the average number of units of the drug-linker structure conjugated per antibody is in the range of from 7 to 8.

18. The antibody-drug conjugate according to claim 1, wherein the average number of units of the drug-linker structure conjugated per antibody is 8.

19. A pharmaceutical composition comprising the antibody-drug conjugate according to claim 1, a pharmacologically acceptable salt thereof, or a hydrate of the conjugate or the salt.

20. A method for treating a tumor, which comprises the step of administering the antibody-drug conjugate according to claim 1, a pharmacologically acceptable salt thereof, or a hydrate of the conjugate or the salt to an individual.

21. The treatment method according to claim 20, wherein the tumor is a tumor expressing CD37.

22. The treatment method according to claim 20, wherein the tumor is any one tumor selected from the group consisting of diffuse large B-cell lymphoma, follicular lymphoma, mantle cell lymphoma, marginal zone lymphoma, Burkitt's lymphoma and chronic lymphocytic leukemia.

23. The treatment method according to claim 20, wherein the tumor is any one tumor selected from the group consisting of T-cell lymphoma such as peripheral Tcell lymphoma or cutaneous T-cell lymphoma, myelodysplastic syndrome and acute myeloid leukemia.

24. A therapeutic agent for a tumor comprising the antibody-drug conjugate according to claim 1, a pharmacologically acceptable salt thereof, or a hydrate of the conjugate or the salt.

25. A physiological saline solution formulation comprising 0.001 to 100 mg/kg of the antibody-drug conjugate according to claim 1, a pharmacologically acceptable salt thereof, or a hydrate of the conjugate or the salt.

26. The antibody-drug conjugate according to claim 1, wherein the anti-CD37 antibody is an antibody comprising a heavy chain variable region and a light chain variable region of the following combination: (g) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 4.

27. The antibody-drug conjugate according to claim 1, wherein the anti-CD37 antibody is an antibody comprising a heavy chain variable region and a light chain variable region of the following combination:

(h) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 6.

28. The antibody-drug conjugate according to claim 1, wherein the anti-CD37 antibody is an antibody comprising a heavy chain variable region and a light chain variable region of the following combination:
(i) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 8.

29. The antibody-drug conjugate according to claim 1, wherein the anti-CD37 antibody is an antibody comprising a heavy chain variable region and a light chain variable region of the following combination:
(j) a light chain variable region consisting of the amino acid sequence at positions 21 to 128 in the light chain full-length amino acid sequence shown in SEQ ID NO: 2 and a heavy chain variable region consisting of the amino acid sequence at positions 20 to 138 in the heavy chain full-length amino acid sequence shown in SEQ ID NO: 10.

30. The antibody-drug conjugate according to claim 26, wherein the anti-CD37 antibody is an antibody comprising a heavy chain and a light chain of the following combination:
(k) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 4.

31. The antibody-drug conjugate according to claim 27, wherein the anti-CD37 antibody is an antibody comprising a heavy chain and a light chain of the following combination:
(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6.

32. The antibody-drug conjugate according to claim 28, wherein the anti-CD37 antibody is an antibody comprising a heavy chain and a light chain of the following combination:
(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8.

33. The antibody-drug conjugate according to claim 29, wherein the anti-CD37 antibody is an antibody comprising a heavy chain and a light chain of the following combination:
(n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

34. An antibody-drug conjugate, which is represented by the following formula:

[Formula 5]

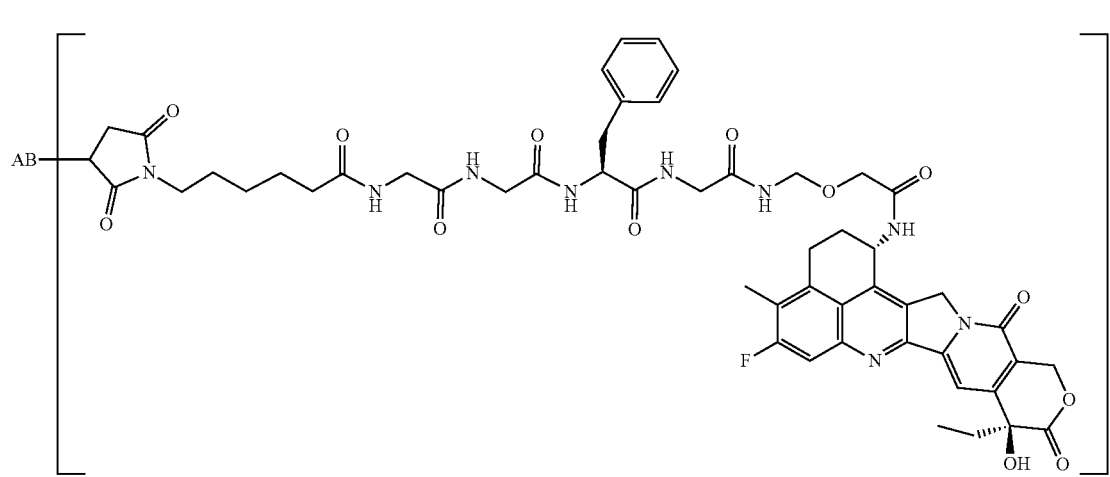

wherein AB represents an anti-CD37 antibody, wherein the anti-CD37 antibody is an antibody comprising a heavy chain and a light chain in any one combination selected from the group consisting of the following combinations (l) to (n):
(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6;
(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8; and (n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10 or one amino acid is deleted from each of the carboxyl termini of both of the antibody heavy chains, the structure in parentheses represents the drug-linker structure, n represents an average number of units of the drug-linker structure conjugated to the anti-CD37 antibody per antibody, wherein the average number of units is in the range of from 7 to 8, and the anti-CD37 antibody is connected to the linker via a sulfhydryl group derived from the antibody.

35. The antibody-drug conjugate according to claim 34, wherein the anti-CD37 antibody is an antibody comprising a heavy chain and a light chain of the following combination:

(l) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 6.

36. The antibody-drug conjugate according to claim 35, wherein the average number of units is 8.

37. The antibody-drug conjugate according to claim 34, wherein the anti-CD37 antibody is an antibody comprising a heavy chain and a light chain of the following combination:

(m) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 8.

38. The antibody-drug conjugate according to claim 37, wherein the average number of units is 8.

39. The antibody-drug conjugate according to claim 34, wherein the anti-CD37 antibody is an antibody comprising a heavy chain and a light chain of the following combination:

(n) a light chain consisting of the amino acid sequence at positions 21 to 234 in the light chain full-length amino acid sequence shown in SEQ ID NO: 2 and a heavy chain consisting of the amino acid sequence at positions 20 to 468 in the heavy chain full-length amino acid sequence shown in SEQ ID NO: 10.

40. The antibody-drug conjugate according to claim 39, wherein the average number of units is 8.

41. A pharmaceutical composition comprising the antibody-drug conjugate according to claim 34, a pharmacologically acceptable salt thereof, or a hydrate of the conjugate or the salt.

42. A method for treating a tumor, which comprises the step of administering the antibody-drug conjugate according to claim 34, a pharmacologically acceptable salt thereof, or a hydrate of the conjugate or the salt to an individual in need thereof.

43. The treatment method according to claim 42, wherein the tumor is a tumor expressing CD37.

44. The treatment method according to claim 42, wherein the tumor is any one tumor selected from the group consisting of diffuse large B-cell lymphoma, follicular lymphoma, mantle cell lymphoma, marginal zone lymphoma, Burkitt's lymphoma and chronic lymphocytic leukemia.

45. The treatment method according to claim 42, wherein the tumor is any one tumor selected from the group consisting of T-cell lymphoma such as peripheral T-cell lymphoma or cutaneous T-cell lymphoma, myelodysplastic syndrome and acute myeloid leukemia.

46. A physiological saline solution formulation comprising 0.001 to 100 mg/kg of the antibody-drug conjugate according to claim 34, a pharmacologically acceptable salt thereof, or a hydrate of the conjugate or the salt.

\* \* \* \* \*